(12) United States Patent
Gasson et al.

(10) Patent No.: US 6,448,034 B1
(45) Date of Patent: Sep. 10, 2002

(54) PRODUCTION OF VARIANT NISIN

(75) Inventors: Michael John Gasson, Norfolk; Helen Mair Dodd, Norwich, both of (GB)

(73) Assignee: Institute of Food Research (GB)

( * ) Notice: Subject to any disclaimer, the term of this patent is extended or adjusted under 35 U.S.C. 154(b) by 0 days.

(21) Appl. No.: 08/836,687

(22) PCT Filed: Nov. 20, 1995

(86) PCT No.: PCT/GB95/02699

§ 371 (c)(1),
(2), (4) Date: Oct. 17, 1997

(87) PCT Pub. No.: WO96/16180

PCT Pub. Date: May 30, 1996

(30) Foreign Application Priority Data

Nov. 19, 1994 (GB) ................................. 9423404

(51) Int. Cl.[7] ........................... C12P 21/04; C12N 1/21; C12N 15/74; C07K 14/195
(52) U.S. Cl. ................... 435/69.1; 435/252.3; 435/473; 435/476; 435/477; 530/300; 530/324
(58) Field of Search ............................ 435/69.1, 252.3, 435/427, 473, 476; 530/300, 324

(56) References Cited

FOREIGN PATENT DOCUMENTS

EP      0 137 869 A2  *  4/1985
WO      WO 93/20213   * 10/1993

OTHER PUBLICATIONS

Leenhouts et al. (1989) Applied and Enviromental Microbiology, vol. 55, pp. 394–400.*
Engelke, G., et al., "Regulation of Nisin Biosynthesis and Immunity in *Lactococcus lactis* 6F3," *Applied and Environmental Microbiology*, 60(3):814–25 (1994).
Kuipers, O.P., et al., "Characterization of the Nisin Gene Cluster nisABTCIPR of *Lactococcus lactis* Requirement of Expression of the nisA and nnisI Genes for Development of Immunity," *Eur. J. Biochem.*, 216:281–91 (1993).
Dodd, H.M., et al., "A Cassette Vector for Protein Engineering the Lantibiotic Nisin," *Gene*, 162:163–64 (1995).
Old et al., *Principles of Gene Manipulation, Studies in Microbiology*, vol. 2, pp. 272–274 (1989).

* cited by examiner

*Primary Examiner*—Elizabeth Slobodyansky
(74) *Attorney, Agent, or Firm*—Nixon Peabody LLP

(57) ABSTRACT

The invention provides a method for making a cell which does not contain a natural nisA gene but expresses a variant nisA gene, said method comprising the steps of providing a cell that contains a natural, chromosomal nisA gene and substituting the natural nisA gene or part thereof with a variant nisA gene at the chromosomal location of the natural nisA gene or part thereof. The invention further provided a process for producing variant nisin and cells for use in the same.

16 Claims, 20 Drawing Sheets

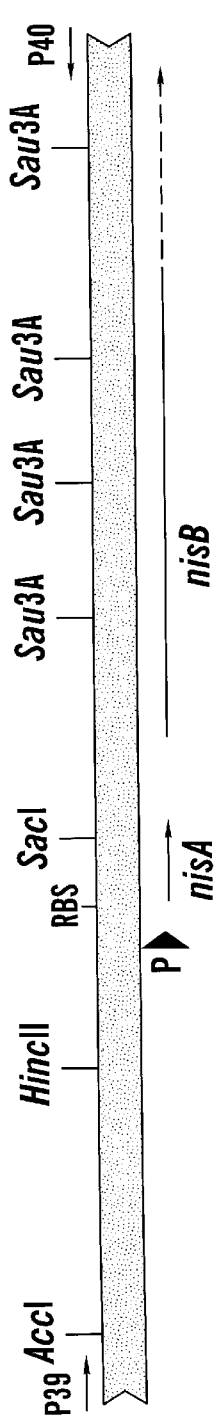
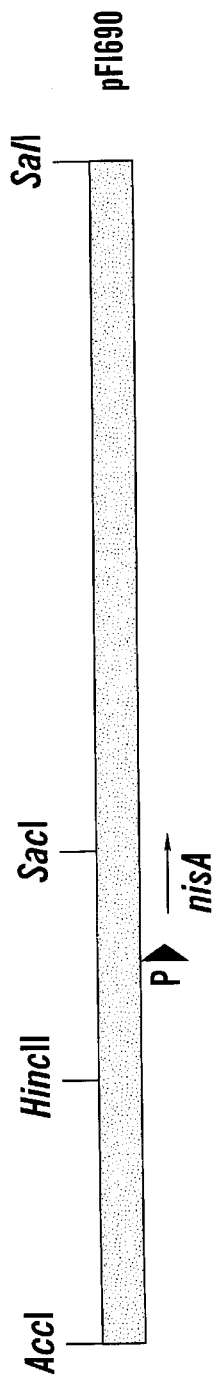
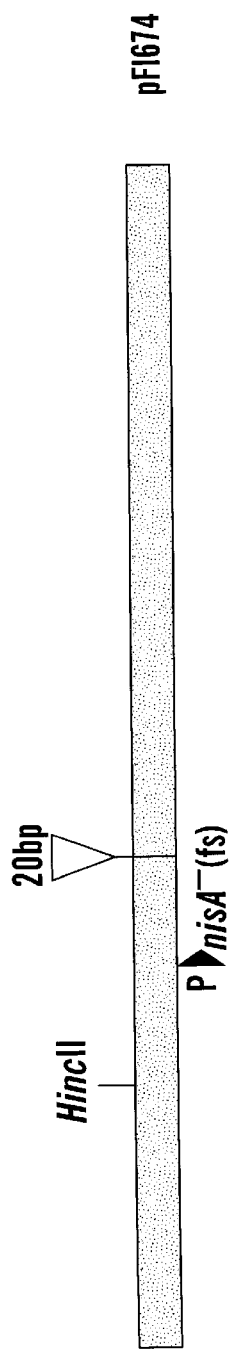
FIG. 2a
FIG. 2b
FIG. 2c

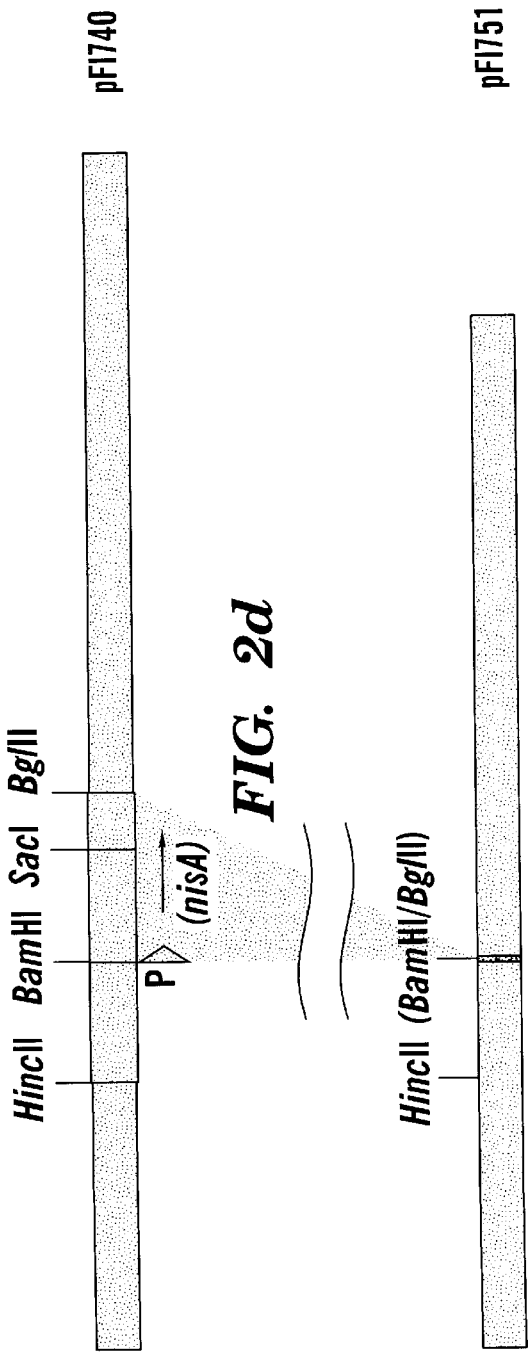
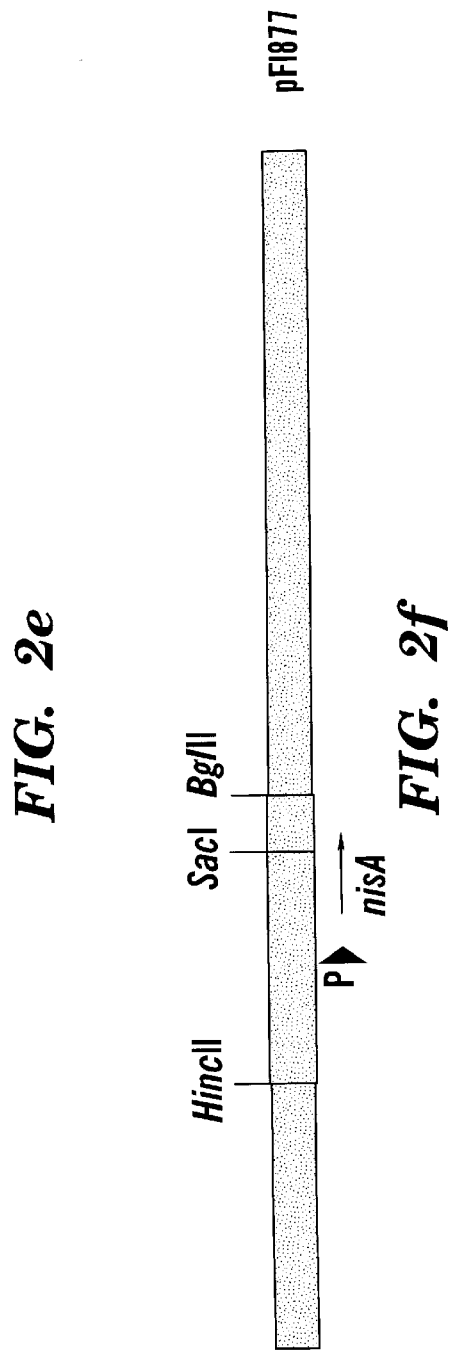
FIG. 2d
FIG. 2e
FIG. 2f

```
                  -35                      -10              *
AATAAAC GGCTCT GATTAAATTCTGAAGTTTGTTAGATACAATGATTTCGTTCGAAGGAA    60
        A    C
       BamHI
              RBS          nisA
CTACAAAATAAATTATAAGGAGGCACTCAAAATGAGTACAAAAGATTTTAACTTGGATTT   120
                                M  S  T  K  D  F  N  L  D  L (CTG)
GGTATCTGTTTCGAAGAAAGATTCAGGTGCATCACCACGCATTACAAGTATTTCGCTATG   180
 V  S  V  S  K  K  D  S  G  A  S  P  R  I  T  S  I  S  L  C
                                                        (A)

SacI
TACACCCGGTTGTAAAACAG GAGCTC TGATGGGTTGTAACATGAAAACAGCAACTTGTCA   240
 T  P  G  C  K  T  G  A  L  M  G  C  N  M  K  T  A  T  C  H (CTG)
TTGTAGTATTCACGTAAGCAAATAACCAAATCAAAGGATAGTATTTGTT AGTTCA GACA   300
 C  S  I  H  V  S  K  *                            A  T
            (A)                                    BgIII
```

```
   1 AATGACTAGTCTATAACTATCTGACAATAGAAACATTAACAAATCTAAACAGTCTTAATTCTATCTTGAGAAGATTATTGGTATAATATATTATTGTC    100
                                                                                      <----- --
                         p1 -35              p1 -10        ◊ transcription start        RBS
 101 GATAACGCGAGCATAATAAACGGCTTGATTAAATTCTGAAGTTTGTTAGATACATGATTCGTTCGAAGGACTACAAATAAATTATAAGGAGGAC    200
     >            <-----                          <-----
 201 TCAAAATGAGTACAAAAGATTTAACTTGGATTTGCTATCTGTTTCGAAGAAAGATTCAGGTGCATCGACCATCAAGTATTCGCTATGTACACC    300
 nisA-> M  S  T  K  D  F  N  L  D  L  V  S  V  S  K  K  D  S  G  A  S  P  R  I  T  S  I  S  L  C  T  P
 301 CGGTTGTAAAACAGGAGCTCTGATGGGTTGTAACATGAAAACAGCAACTTGTCATTGTAGTATTCACGTAAGCAAATCAAACGATACTATTT    400
      G  C  K  T  G  A  L  M  G  C  N  M  K  T  A  T  C  H  C  S  I  H  V  S  K  *
                                                                                     RBS
 401 TGTTAGTTCAGACAATGATACTATCCTATTTTTATAAGTTATTAGGGTTGCTAAATACTTATAAAATAGCTTATAAAAATAAAGAGGAAAAAACATGATAAAGGTTC    500
                                                                                        nisB-> M  I  K  S  S
 501 ATTTAAAGCTCAACCGTTTTTAGTAAGAAATACAATTTATATCCTCAAACGATAAACGGAGTTTACTGATATACTCAAGTCATTGAGACTGTAAGACTAAA    600
      F  K  A  Q  P  F  L  V  R  N  T  I  L  S  P  N  D  K  R  S  F  T  E  Y  T  Q  V  I  E  T  V  S  K
 601 AATAAAGTTTTTTTGAACAGTTACTACTAGCTAATCCAAACTCTATGATGTTCAGAAGATATGCAAATGCTGGTCTGTTAAAGAAGAAAGGTTAAAA    700
      N  K  V  F  L  E  Q  L  L  L  A  N  P  K  L  Y  D  V  M  Q  K  Y  N  A  G  L  L  K  K  R  V  K  K
 701 AATTATTGAATCTATTTACAAGTACTATTTTACAAGAGAAGTTATTACGATCCATTGGATTATTAGTGAAACTTCAATTGGTGTTTTTTTCGAAAAG    800
      L  F  E  S  I  Y  K  Y  Y  K  R  S  Y  L  R  S  T  P  F  F  G  L  F  S  E  T  S  I  G  V  F  S  K  S
 801 TTCACAGTACAAGTTAATGGAAAGACTAATGGTATAAGACTTGAGATCGAGTTTTCAAGTTTATACATAAATAGTAGTGACTTGAAGAAGTAAATATTA    900
      S  Q  Y  K  L  M  G  K  T  T  K  G  I  R  L  D  T  Q  W  L  I  R  L  V  H  K  M  E  V  D  F  S  K
 901 AAGTTATCATTTACTAGAATGAAATTCTTCGAATTTGTGAGAATGACTTATCAAAAATATGAAACTGTAACGCTTGTCATGGAGACGA    1000
      K  L  S  F  T  R  N  N  A  N  Y  K  F  G  D  R  V  F  Q  V  Y  T  I  N  S  S  E  L  E  E  V  N  I  K
1001 AATATACGAATGTTTATCAAATGTTATTTCTGAATTTTGTGAGAATGACTATAGTTAATCATTATTTGATCTCTAATTTACAAAAGATTTGTCTCAGATTTTCTTGAAC    1100
      Y  T  N  V  Y  Q  I  I  S  E  F  C  E  N  D  Y  Q  K  Y  E  D  I  C  E  T  V  T  L  C  Y  G  D  E
1101 ATATAGAGAACTATCGGAACAATATCTTGGAGTCGATAGTAATCATTATTTGAGATCATTAATTATTTACAAAAGATTTGTTCAGATTTCTTGAAC    1200
      Y  R  E  L  S  E  Q  Y  L  G  S  L  I  V  N  H  Y  L  I  S  N  L  Q  K  D  L  L  S  D  F  S  W  N
1201 ACTTTTTGACTAAAGTTGAAGCTATAGATGAAGATAAAAAAGTTTATATCAGGAAATGTACAAATTCTGAGAATGATATTCAAATTGATTAATTAGTGATAGTGA    1300
      T  F  L  T  K  V  E  A  I  D  E  D  K  K  V  Y  I  I  P  L  K  K  V  Q  K  F  I  Q  E  Y  S  E  I  E  I
1301 TTGGTGAAGGTATTGAGAAAGCTGAAAGATATCAGAACATTTAGCTGAGTTTTTAGGAAATACGAAAATCGTAAGAAGAACATATTGATGACTAT    1400
      G  E  I  E  K  L  K  E  I  Y  Q  E  M  S  Q  I  L  E  N  D  N  Y  I  Q  D  L  I  S  D  S  E
1401 AATAAATTTGATGTTAAACAAAAGCAACAATTAGCTGAACATTTAGCTGAGTTTTTAGGAAATACGAAAATCGTAAGAAGAACATATTGATGACTAT    1500
      I  N  F  D  V  K  Q  K  Q  Q  L  E  H  L  A  E  F  L  G  N  T  T  K  S  V  R  R  T  Y  L  D  D  Y
1501 AAGGATAAATTTATCGAAAAATATGGTGTAGATCAAGAAGTACAAATAACAGAATTATTTGATTCTACATTTGGCATAGGAGCTCCATATAAATTATATATC    1600
      K  D  K  F  I  E  K  Y  G  V  D  Q  E  V  Q  I  T  E  L  F  D  S  T  F  G  I  G  A  P  Y  N  Y  N  H
```

FIG. 7 (continued)

```
1601 ATCCTGAAATGACTTTTATGAGTCCGAACCGAGTACTACTGTCATATATTCAGAGAGGAGAGAAAGTACCTCAGCATGTATGTAGAGCCGTAAAAA    1700
     P  R  N  D  F  Y  E  S  E  P  S  T  L  Y  Y  S  E  E  E  R  E  K  Y  L  S  M  Y  V  E  A  V  K  N
1701 TCATAATGTAATTAATCTTGACGACTAGAGTCCATTATCAAAAAAATGACTTAGAAAAGAAAGTGAACTTCAAGGGTTAGAATTATTTTTGAATTTG    1800
     H  N  V  I  N  L  D  D  L  E  S  H  Y  Q  K  M  D  L  E  K  K  S  E  L  Q  G  L  E  L  F  L  N  L
1801 GCAAAGGAGTATGAAAAAGATATTTTATTTTAGGGGATATCGTTGGAGAAATAATTTGGAGGGCATCAGGTAGATTTCTGCACTCTCCGGAGT       1900
     A  K  E  Y  E  K  D  I  F  I  L  G  D  I  V  G  N  N  N  L  G  G  A  S  G  R  F  S  A  L  S  P  E  L
1901 TAACAAGTTATCATAGAACGATAGTAGATTCTGTCGAAAGAGAAATGAGAATAAAGAAATTACATCGTGTGAAATAGTATTTCTTCCAGAAATATCAG   2000
     T  S  Y  H  R  T  I  V  D  S  V  E  R  E  N  E  N  K  E  I  T  S  C  E  I  V  F  L  P  E  N  I  R
2001 ACATGCTAACGTTATGCATACATAATTATGAGGAGGAAAGTACTTCCATTTTTACAAGTACAAGTCACAATGAAGTTCTGTTAACTAATATCTATATT   2100
     H  A  N  V  M  H  T  S  I  M  R  R  K  V  L  P  F  F  T  S  T  S  H  N  E  V  L  L  T  N  I  Y  I
2101 GGAATAGACGAAAAAGAAAAATTTATGCGAGACATTTCAACTCAAGAGGTATGAAATTCTACATTACAAGCATGTAATAAAACGTTATTCAGTA      2200
     G  I  D  E  K  E  K  F  Y  A  R  D  I  S  T  Q  E  V  L  K  F  Y  I  T  S  M  Y  N  K  T  L  F  S  N
2201 ATGAGCTAAGATTCTTTTACGAAATTCATTAGATGACAAGTTGCTAATTACCTTGGAACTTATTACAGAGACTTTGATTATATTCCACGTTTAGT    2300
     E  L  R  F  L  Y  E  I  S  L  D  D  K  F  G  N  L  P  W  E  L  I  Y  R  D  F  D  Y  I  P  R  L  V
2301 ATTTGACGAAATAGTAATATCTCCTGCTAAATGAGATAATAAGTTTATTATCACAGGAAAAACCCATTGGATATGAAAATTTAGAGTCGGCCGATAAAGAAGCT  2400
     F  D  E  I  V  I  S  P  A  K  W  K  I  W  G  R  D  V  N  S  K  M  T  I  R  E  L  I  Q  S  K  E  I
2401 CCCAAAGAGTTTTATATTGTCAATGGAGATAATAAAGTTTATTTTGAAGATGAAAATATCATAAATAAGGGAGAGTTGCCGATGTTGTAGTGCCTTT   2500
     P  K  E  F  Y  I  V  N  G  D  N  K  V  Y  L  S  Q  E  N  P  L  D  M  E  I  L  E  S  A  I  K  K  S
2501 CAAAAGAAAAGATTTTAGAGCTACAAGAATTATTTGAAGATGAAAATATCATAAATAAGGGAGAGTTGCCGATGTTGTAGTGCCTTT             2600
     K  R  K  D  F  I  E  L  Q  E  Y  F  E  D  E  N  I  I  N  K  G  E  K  G  R  V  A  D  V  V  P  F
2601 TATTAGAACGAGAGCATTAGGTAATGAAGGAGAGCATTATAAGAGGAGCATTTTACTGTCGATATTCCAGATATTAGTAGCAAACCTGGGTGAAATCTAT  2700
     I  R  T  R  A  L  G  N  E  G  R  A  F  I  R  E  K  R  V  S  V  E  R  E  K  L  P  F  N  E  W  L
2701 TATCTAAAGTTGTACATTCTAATATAAATCGTCAAAATGAATTTTTACTGTCGTATCTTCCAGATATTCAGAAATATTCCAGATATTAGTAGCAAATCTAT   2800
     Y  L  K  L  Y  I  S  I  N  R  Q  N  E  F  L  L  S  Y  L  P  D  D  I  Q  K  I  V  A  N  L  G  G  N  L  F
2801 TCTTCCTAAGATATACTGATCCTAACCTAAGATGTCAACTTAGATTAGATGCGTATAAAATGTTCAGATTTTTAGCTTACGGATCTATTCTTGAAATCTTAAAAAG  2900
     F  L  R  Y  T  D  P  K  P  H  I  R  L  R  I  K  C  S  D  L  F  L  A  Y  G  S  I  L  E  I  L  K  R
2901 GAGTCGGAAAATAGGATAATGTCTAAAATTACTCAACTTTCTATTTGATATTCTATTTGATATCAAGAAGATATAATGATTGGAAGTCATCCGAACGA   3000
     S  R  K  N  R  I  M  S  T  F  D  I  S  I  Y  D  Q  E  V  E  R  Y  G  G  F  D  T  L  E  L  S  E  A
3001 ATATTTGTGCCGATTCTAAAATTATTCCAAATTTGCTTACATTGATAAAAGATACTAATAATGATTGGAAGTTATCATCTTGTGAATT              3100
     I  F  C  A  D  S  K  I  I  P  N  L  L  T  L  I  K  D  T  N  N  D  W  K  V  D  D  V  S  I  L  V  N  Y
3101 ATTTATATCTGAAATGCTTCTTCAGAATGATAATAAACAAAAGATTCTAATTTTTGAATTTAGTAGTCCTAAAAAGGTTAAGAAGTTAAAATGTCAATGAAAA 3200
     L  Y  L  K  C  F  F  Q  N  D  N  K  K  I  L  N  F  L  N  L  V  S  P  K  K  V  K  E  N  V  N  E  K
```

```
      TAAATACAAAAAGTTGATTCATACATGGAAGAATTAATGTAGTGAGCAAATTCTTGAAGAATACGGAGAAGTGGCACGGGTTTCTTGA                          6400
       N  T  K  K  F  D  S  Y  M  E  E  F  N  V  N  S  E  Q  I  L  E  E  Y  G  D  E  S  G  T  G  F  L  E
                                                                                                   RBS
6401  AGGAATAAGTGGCTGTATACTGGTAGAAATGAGAAGATATTTAATACTTATTGTGGCCTTAATAATCGTAATATCAATTTACTTTGAAATTCAATATTTAGACGATTTTTGAAA  6500
       G  I  S  G  C  I  L  V  L  S  K  F  E  Y  S  I  N  F  T  Y  W  R  Q  A  L  L  F  D  D  F  L  K
6501  GGAGGAAGAGAAATGAGAAGATATTTAATACTTATTGTGGCCTTAATAATCGTAATATCAATTTACTTTGAAATCAAACAAGTCATAAAAGGTGAG                    6600
         nisI ->  M  R  R  Y  L  I  L  I  V  A  L  I  G  I  T  G  L  S  G  C  Y  Q  T  S  H  K  K  V  R
       G  G  K  R  K  *
6601  GTTTGACGACGAAGGAAGTTATACTAATTTTATTTATGATAATAAATCGTATTCGTAACTGATAAGGAGAATTCCTCAGGAGAACGTTAACAATTCCAAAGTA             6700
       F  D  E  G  S  Y  T  N  F  I  Y  D  N  K  S  Y  F  V  T  D  K  E  I  P  Q  E  N  V  N  N  S  K  V
6701  AAATTTTATAAGCTGTTGATTGTTGACATGAAAAGTGAGAAAACTTTATCAAGTAGCAACAAAAAACTTTTGTGACTTTGTCTTAAATAATATTATGAGG                6800
       K  F  Y  K  L  L  I  V  D  M  K  S  E  K  L  L  S  S  N  K  N  S  V  T  L  V  L  N  N  I  Y  E  A
6801  CTTCTGACAAGTCGCTATGTATGGGTATTAACGACAGATATTAAGATACTTCCAGAAAGTGATAAGGGGCCGTCAAAGCTTTGAGATTACAAAACTT                   6900
       S  D  K  S  L  C  M  G  I  N  D  R  Y  Y  K  I  L  P  E  S  D  K  G  A  V  K  A  L  R  L  Q  N  F
6901  TGATGTGACAAGCGATATTTCTGATGATAATTTTGTTATTGATAAAAATGATTCAGTAAGTACGATATGGGAAATATTACAGTATATCGGACACC                    7000
       D  V  T  S  D  I  S  D  D  N  F  V  I  D  K  N  D  S  R  K  I  D  Y  M  G  N  I  Y  S  I  S  D  T
7001  ACCGTATCTGATGAAGAATTGGGAGAATATCAGGATGTTTTAGCTGAATATCAGGATGTTTTGATTGTTGATTCAGTTAGTGGCAAAAGTATCCCGAGTCTGAATGGG         7100
       T  V  S  D  E  E  L  G  E  Y  Q  D  V  L  A  E  V  R  V  F  D  S  V  S  G  K  S  I  P  R  S  E  W  G
7101  GGAGAATTGATAAGGATGGTTCAAATTCCAAACGAGTACGGATTATGGCGAAATCTCTTATTAGAGAAAATCTCTATTAGAGGAAAATCTCTTACTGAAGCATT            7200
       R  I  D  K  D  G  S  N  S  K  Q  S  R  T  E  W  D  Y  G  E  I  H  S  I  R  G  K  S  L  T  E  A  F
7201  TGCCCGTTGAGATAAATGATGATTTAAGCTTGCAACGAAGGTAGGAGAAACTAGAGTGAAAAAATACTAGGTTTCCTTTTATCGTTTGTTCGTTGGGTTT               7300
       A  V  E  I  N  D  D  F  K  L  A  T  K  V  G  N  *
                                                                  RBS
                                                              nisP ->  V  K  K  I  L  G  F  L  F  I  V  C  S  L  G  L
7301  ATCAGCAACTGTCATGGGAGACAACAAATTCACAACAGTTACTCCAAATAATAACGGAATTAATCATAATTCTAATGCAATTTATCT                            7400
       L  A  T  V  H  G  E  T  T  N  S  Q  Q  L  L  S  N  N  I  N  T  E  L  I  N  H  N  S  N  A  I  L  S
7401  TCAACAGAGGATCAACGACTGATTCGATTAATCTAGGGGCGCAGTCACCTGCA    -->                                                       7554
       S  T  E  G  S  T  T  D  S  I  N  L  G  A  Q  S  P  A    etc
```

```
  1 CAATTTTACTTATTGGAGACAAGCACTGTTACTTTTTGACGATTTTTTGAAAGGAGGAAGAGAAATATTAATACTTATTGTGGCCTTAA         100
                                            RBS
      N F T Y W R Q A L L L F D D F L K G G K R K *
                                              nisI -> M R R Y L I L I V A L I 101 TAGGGATAACAGGTTTATCAGGGTGTTATCAAACAAGTTGAAGGTTGAGCAAGGAAGTTATACTAATTTTATTTATGATAATAAATCGTA         200
      G I T G L S G C Y Q T S H K K V R F D E G S Y T N F I Y D N K S Y 201 TTTCGTAACTGATAAGGAGATTCCTCAGGAGAATGTTAACAATTCCAAAGTAAAATTTATAAGCTGTGTGATTGTTGACATGAAAAGTGAGAAACTTTTA     300
      F V T D K E I P Q E N V N N S K V K F Y K L L I V D M K S E K L L 301 TCAAGTAGCAACAAAAATAGTGTGACTTTGGTCTTAAATAATATTTATGAAGCTTCTGACAAGTCGCTATGTATGGGTATTAACGACAGATACTATAAGA    400
      S S S N K N S V T L V L N N I Y E A S D K S L C M G I N D R Y Y K I
                                              HindIII 401 TACTTCCAGAAAGTGATAAGGGGCGCGTCAAAGCTTTGAGATTACAAACTTGATGACAACCGATATTTCTGATGATAATTTTGTTATTGATAAAAA    500
      L P E S D K G A V K A L R L Q N F D V T S D I S D D N F V I D K N 501 TGATTCACGAAAAATTGACTATATGGGAAATATTTACAGTATATCCGACACCACCGTATCTGATGAAGAATTGGGAGAATATCAGGATGTTTAGCTGAA    600
      D S R K I D Y M G N I Y S I S D T T V S D E E L G E Y Q D V L A E 601 GTACGTGTGTTGATTCAGTTAGTGGCAAAGTCTATCCCGAGGTCTGAATGGGGAGAATTGATAGGATGGTTCAAATTCCAAACAGAGTAGGACGGAAT    700
      V R V F D S V S G K S I P R S E W G R I D K D G S N S K Q S R T E W
                                                                   RBS 701 GGGATTATGGCGAAATCCATTCATTACTAGGAGAAATCTCTTACTGAAGCATCTCTGAAAGCATTGATTTAAGCTTGCAACGAAGGTAGGAAA        800
      D Y G E I H S I R G K S L T E A F A V E I N D D F K L A T K V G N
                                                              HindIII 801 CTAGAGTCTGAAAAAAATACTAGGTTTCCTTTTATCGTTTGTTCGTTGGGTTTATCAGCAACTGTCATGGGGACAACAAATTCACACAGTACTCTC        900
      *
      nisP -> V K K I L G F L F I V C S L G L S A T V H G E T T N S Q Q L L S 901 AAATAATATTAATACGGAATTAATTAATCATAATTCTAATGCAATTTATCTTCAATTGATTGATTAATCTAGGGGCGCAGTCA                      1000
      N N I N T E L I N H N S N A I L S S T E G S T T D S I N L G A Q S 1001 CCTGCAGTAAAATCGACAACAAGGACTTGAATTGGATGTAACTGCTAAACTTTATTACAGACATCAGCTGTTCAAAAAGAAATGAAAGTTCGT        1100
       PstI
      P A V K S T T R T E L D V T G A A K T L L Q T S A V Q K E M K V S L 1101 TGCAAGAAACTCAAGTTAGTTCTGAATTCAGTGAGTTCAGTGAGAGAATAGCGTTACAAATAAGAAGACAGTTCCAGTATCTAAGGATGACTACTTGAGCAAAGTGA     1200
                 EcoRI
      Q E T Q V S S E F S K R D S V T N K E A V P V S K D E L L E Q S E 1201 AGTAGTCGTTCAACATCATCGATTCAAAAAATAAATCCTGATAATAAGAAGAAAAGCTAACTTCGTTACTTCCTCCGCTTATTAAGGAAAAA            1300
      V V V S T S S I Q K N K I L D N K K K R A N F V T S S P L I K E K 1301 CCATCAAATTCTAAAGATGCATCTGGTGTAATTGATAATTCTGCTCCTCTATCTATCGTAAGCTAAGAAGTGTATCTCTTAGACAACCTTTAA        1400
      P S N S K D A S G V I D N S A S P L S Y R K A K E V V S L R Q P L K
```

FIG. 8 (continued)

```
                        RBS
2901 CTAAACAATCGGAGGTAAAGTGGTGTATAAAATTTAAATAATGAAGACACCATTAGAAATGAGAAACTAT  3000
             nisR -> V V Y K I L I V D D D Q E I L K L M K T A L E M R N Y
                                                                EcoRV
3001 GAAGTTGCGACGCATCAAAACATTTCACTTCCCTTGATATATCTGATTTCAGGGATTTGATTTGTTAGATATCATGATGTCAAATATTGAAG 3100
     E V A T H Q N I S L P L D I T D F Q G F D L I L L D I M M S N I E G
3101 GGACAGAAATTTGTAAAGGATTCGCAGAGAAATATCAACTCCAATATCTTGTTAGTGCGAAAGATACAGAAGGATATTATAAACGGCTTAGGTAT 3200
     T E I C K R I R R E I S T P I I F V S A K D T E E D I I N G L G I
3201 TGGTGGGGATGACTATATTACTAAGCCTTTTAGCCTTAAACAGTTGGTTGCAAAAGTTGAAGCAAATATAAAGCGAGAACGCAATAAACATGCAGTT 3300
     G G D D Y I T K P F S L K Q L V A K V E A N I K R E E R N K H A V
3301 CATGTTTTTCAGAGAATTCGTAGAGATTTAGGACCAATTACATTTTATTTAGAAGAAAGGCGAGTCTGTCAATGGTCAAACAATTCCACTGACTTGTC 3400
     H V F S E I R R D L G P I T F Y L E E R R V C V N G Q T I P L T C R
3401 GTGAATACGATATATTCTTGAATTACTATCACAACGAACTTCTAAAGTTTATACGAGAGATATTTATGACGTATATGATGATGAATATTCAATGCACT 3500
     E Y D I L E L L S Q R T S K V Y T R E D I Y D D V Y D E Y S N A L
                                                                RBS
3501 TTTTCGGTCAATCTCGAGATATATTTATCAGATTAGGAGTAAGTTTGCATCCAAGCTGTCATTGAAATTATCATAGGTACTGTCTACTTATCCGTTGTGTTGTACTCAGTGG 3600
     F R S I S E Y I Y Q I R S K F A P Y D I N P I K T V R G L G Y Q W
3601 CATGGGTAAAAAATATTCAATGCGTCGACGATATGCCAAGCTGATATGGGCTTGACT 3700
     H G * -> M G K K Y S M R R R I W Q A V I E I I I G T C L L I L L L G L T
3701 TTCTTTCTACGACACAAATTGGACAAATCAGTGGTTCAGAAAACTATTCGTTTAGATTCAGATAATTTAACTATTTCTGATATCGAACGTGATATGA 3800
     F F L R Q I G Q I S G S E T I R L S D N L T I S D I E R D M K
3801 AACACTACCATATGATTATTTTTGACAATGATACAAGTAAAATTTTGGGAGGACATTATGTCAAGTCGGATGTACCTAGTTTTGTAGCTTCAAAA 3900
     H Y P Y D Y I I F D N D T S K I L G G H Y V K S D V P S F V A S K
3901 ACAGTCTTCACATAATATTACAGAAGAGAAATTACTTATACTTATTCAGTTGTTTTAAGACAAATAAGCATTTTCAGTTGTTTTAAGACAAATAAGCATTTTCAGTTGTTTTCAGTTGCCTGAATTT 4000
     Q S S H N I T E G E I T Y T Y S S N K H F S V V L R Q N S M P E F
```

PRODUCTION OF VARIANT NISIN

FIELD OF THE INVENTION

The present invention relates to improved methods and bacterial strains for the production of nisin, in particular protein-engineered nisins.

BACKGROUND OF THE INVENTION

Nisin is a highly modified peptide antibiotic produced, for example, by certain strains of *Lactococcus lactis*. It is of great interest to the food industry because of its efficient antimicrobial activity against a wide range of gram-positive organisms including many spoilage bacteria and food pathogens, for example, Listeria, Clostridia and Bacillus species (see Fowler & Gasson (1990) in *Food Preservatives* (eds N. J. Russell & G. W. Goulds) pages 135–152, Blackie and Sons, Glasgow, UK).

The chemical structure of nisin is well established (FIG. 1). It is a member of the family of antibiotics termed lantibiotics. These unusual polycyclic peptides share the structural features of dehydro-residues and intrachain sulphide bridges forming lanthionine and β-methyllanthionine rings. The atypical residues are introduced by post-translational modification of amino acids serine, threonine and cysteine in the primary sequence of a precursor peptide (lantibiotics are the subject of a recent extensive review by Jung (1991) in *Nisins and novel lantibiotics* (eds Jury, G. & Sahl, H.-S.) pages 1–34, ESCOM, Leiden, Netherlands). Biosynthesis of nisin thus involves genes for both the inactive precursor of nisin, known as prenisin, (nisA) and also the modifying enzymes responsible for nisin maturation. The mature nisin molecule is based on a sequence of 34 amino acids. The protein encoded by nisA includes a 23 amino acid N terminal signal sequence which is cleaved off during secretion of nisin. The conversion of prenisin, encoded by nisA, into mature nisin involves cleavage of the leader and the modification of individual amino acids. A nisA gene has been cloned and characterised and shown to have a chromosomal location (see Dodd et al (1990) *J. Gen. Microbiol.* 136, 555–566). A number of additional genes involved in the enzymatic modification of prenisin, translocation and immunity are encoded by nisin producing strains (Kuipers et al (1993) *Eur. J. Biochem.* 216, 281–291; Engelke et al (1994) *Appl. Environ. Microbiol.* 60, 814–825).

Established protein engineering techniques can be used to introduce changes to the amino acid sequence of nisin. This involves modifying the coding region of the nisin structural gene, nisA, for example by site-directed or random mutagenesis. Expression of these changes is complicated by the fact that nisin is post-translationally modified.

Variant nisins may be constructed by the expression of variant nisA genes in a host strain which encodes the necessary maturation machinery, and thus can process the modified precursor peptide. One approach is to transform a nisin producing strain with a recombinant plasmid encoding variant nisA gene. In this background the host's maturation enzymes are available to process both the resident prenisin and its plasmid-encoded variant. A strategy of this type has been reported for a strain that carries the wild-type nisin transposon (Kuipers et al (1991) in *Nisins and novel lantibiotics* (eds Jung, G. & Sahl, H.-S.), pages 250–259, ESCOM, Leiden, Netherlands). However, the disadvantage of this system is that both the host's nisin and the engineered variant are synthesised together, making complex chemical separation procedures necessary prior to analysis of the properties of the novel peptide. Such a procedure would be particularly undesirable for industrial scale production of a variant nisin.

WO 93/20213 describes a process for producing a variant nisin from Lactococcus in the absence of natural nisin in which a plasmid-borne variant nisA gene (which encodes the variant nisin) is introduced into a strain of Lactococcus which does not secrete its natural nisA nisin (because the nisA gene has been inactivated) but is capable of expressing genes for nisin modification, immunity and translocation out of the cell.

WO 92/18633 discloses plasmid-based systems for the expression of variant nisins from the nisZ gene (or mutants thereof) in Lactococcus strains that do not produce natural nisA nisin.

Unexpectedly we have found that by replacing the natural, chromosomal copy of the nisA gene (or at least a part thereof) with a variant nisA gene (or part thereof) we can produce surprisingly high levels of nisin, particularly variant nisins, from Lactococcus. Thus, the present invention provides improved methods and organisms for producing variant nisins with greater efficiency.

SUMMARY OF THE INVENTION

One aspect of the invention provides a method for making a cell which does not contain a natural nisA gene but expresses a nisin comprising the step of providing a cell with a variant nisA gene and genes for nisin modification, secretion and immunity wherein the variant nisA gene has the same relationship as the natural nisA gene to the gene cluster containing the natural nisA gene and the genes for nisin modification, secretion and immunity.

A second aspect of the invention provides a cell which does not contain a natural nisA gene but expresses a nisin comprising a variant nisA gene wherein the variant nisA gene has the same relationship as the natural nisA gene to a gene cluster containing the natural nisA gene and the genes for nisin modification, secretion and immunity.

A third aspect of the invention provides a process for producing nisin comprising culturing a cell as described in the second aspect of the invention and obtaining the nisin produced thereby.

A fourth aspect of the invention provides a nisin produced by the process of the invention.

A fifth aspect of the invention provides the use of a nisin produced according to the process of the invention as an antimicrobial agent. The ability of nisin to inhibit growth of spoilage bacteria and food pathogens has resulted in the extensive use of nisin as a natural preservative in certain food products, particularly dairy products such as soft cheeses. Variant nisins are also used.

BRIEF DESCRIPTION OF THE DRAWINGS

FIG. 2 shows diagramatically some of the recombinant plasmids constructed and used in this work.

FIG. 4 shows the nucleotide sequence (SEQ. ID. No. 19) and corresponding amino acid sequence (SEQ. ID. No. 20) of at least part of the natural nisA gene and expression signals showing changes introduced by PCR-mediated site-specific mutagenesis. BamHI and BglII sites flanking nisA were engineered into plasmid pFI740 (SEQ. ID. No. 21) (FIG. 2d). A BglII site flanking nisA was engineered into FI690 to create plasmid FI877 (SEQ. ID. No. 22). The substitution of Ser5 and Ser33 codons for alanine codons in variant nisA genes (nisA/S5A, strain FI8070, SEQ. ID. No. 23; nisA/S33A, strain FI8198, SEQ. ID. No. 25; and nisA/S5A,S33A, strain FI8199, SEQ. ID. No. 27) (Table 1) is shown above the sequence. The corresponding amino acid sequences are: nisA/S5A (SEQ. ID. No. 24); nisA/S33A (SEQ. ID. No. 26); and nisA/S5A,S33A (SEQ. ID. No. 28).

FIG. 7 shows the nucleotide sequence of the gene cluster (SEQ. ID. No. 29) containing the sequences of the nisA, nisB, nisT, nisC and nisI genes, as well as a portion of the nisP gene of Tn5276 of *L. lactis* NIZO R5, and is taken from Kuipers et al (1993) *Eur. J. Biochem.* 216, 281–291. The corresponding amino acid sequences of the nisA (SEQ. ID. No. 20), nisB (SEQ. ID. No. 30), nisT (SEQ. ID. No. 31), nisC (SEQ. ID. No. 32), nisI (SEQ. ID. No. 33), and a partial nisP protein (SEQ. ID. No. 34) are also shown. Putative ribosome-binding sites (RBS) and inverted repeats (→) are indicated, as is the transcription-initiation site of the nisA gene and its preceding canonical sequences. Positions of restriction sites used are as follows: AccI, 6383–6388; BclI, 2914–2919; EcoRI, 3461–3466; EcoRV, 1805–1810; HaeIII, 6509–6512; NcoI, 6218–6223; NdeI, 4518–4523; PstI, 7418–7423; SstI, 283–288, 1547–1552 and 2463–2468.

FIG. 8 shows a nucleotide sequence of cloned 5.0-kb region (SEQ. ID. No. 35) downstream from nisC with open reading frames nisI, nisP, nisR, and nisK, and is taken from Engelke et al (1994) *Appl. Environ. Microbiol.* 60,814–825. Possible ribosome-binding sites (RBS), restriction sites, and inverted repeats are underlined. The first 22 amino acids (SEQ. ID. No. 36) shown are the last 22 amino acids in the nisC protein (SEQ. ID. No. 32, shown in FIG. 7). Open reading frames for the corresponding amino acid sequences of nisI (SEQ. ID. No. 33), nisP (SEQ. ID. No. 37), nisR (SEQ. ID. No. 38), and nisK (SEQ. ID. No. 39) are designated by a one-letter code. Arrows indicate the putative signal peptide cleavage sites of NisI and NisP; the putative membrane anchor sequence of NisP is underlined. Conserved, functional, and active-site amino acids are written in boldface letters and marked by asterisks.

DETAILED DESCRIPTION OF THE INVENTION

One aspect of the invention provides a method for making a cell which does not contain a natural nisA gene but expresses a nisin comprising the step of providing a cell with a variant nisA gene and genes for nisin modification, secretion and immunity wherein the variant nisA gene has the same relationship as the natural nisA gene to the gene cluster containing the natural nisA gene and the genes for nisin modification, secretion and immunity.

By "providing a cell with a variant nisA gene and genes for nisin modification, secretion and immunity" we include inserting a variant nisA gene into a cell that already contains genes for nisin modification, secretion and immunity as well as inserting into a cell at the same time a variant nisA gene plus genes for nisin modification, secretion and immunity.

The gene cluster containing the genes encoding pre-nisin A (which is processed to form nisin A) and the genes for nisin modification, secretion and immunity from *Lactococcus lactis* (nisABTCIPRK) are described in Kuipers et al (1993) *Eur. J. Biochem.* 216, 281–291 and Engelke et al (1994) *Appl. Environ. Microbiol.* 60, 814–825 incorporated herein by reference.

Figure 7:
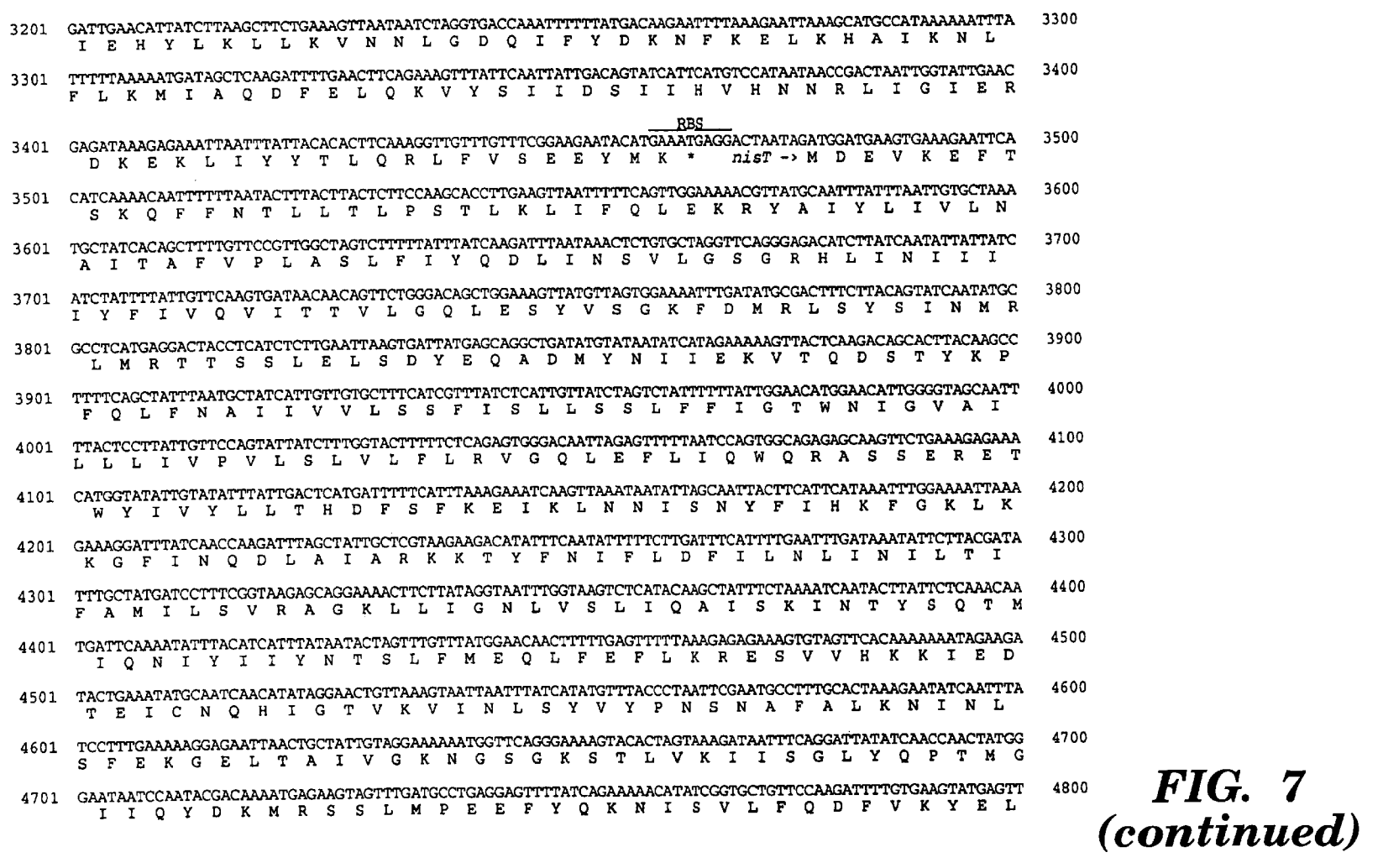
Figure 7:
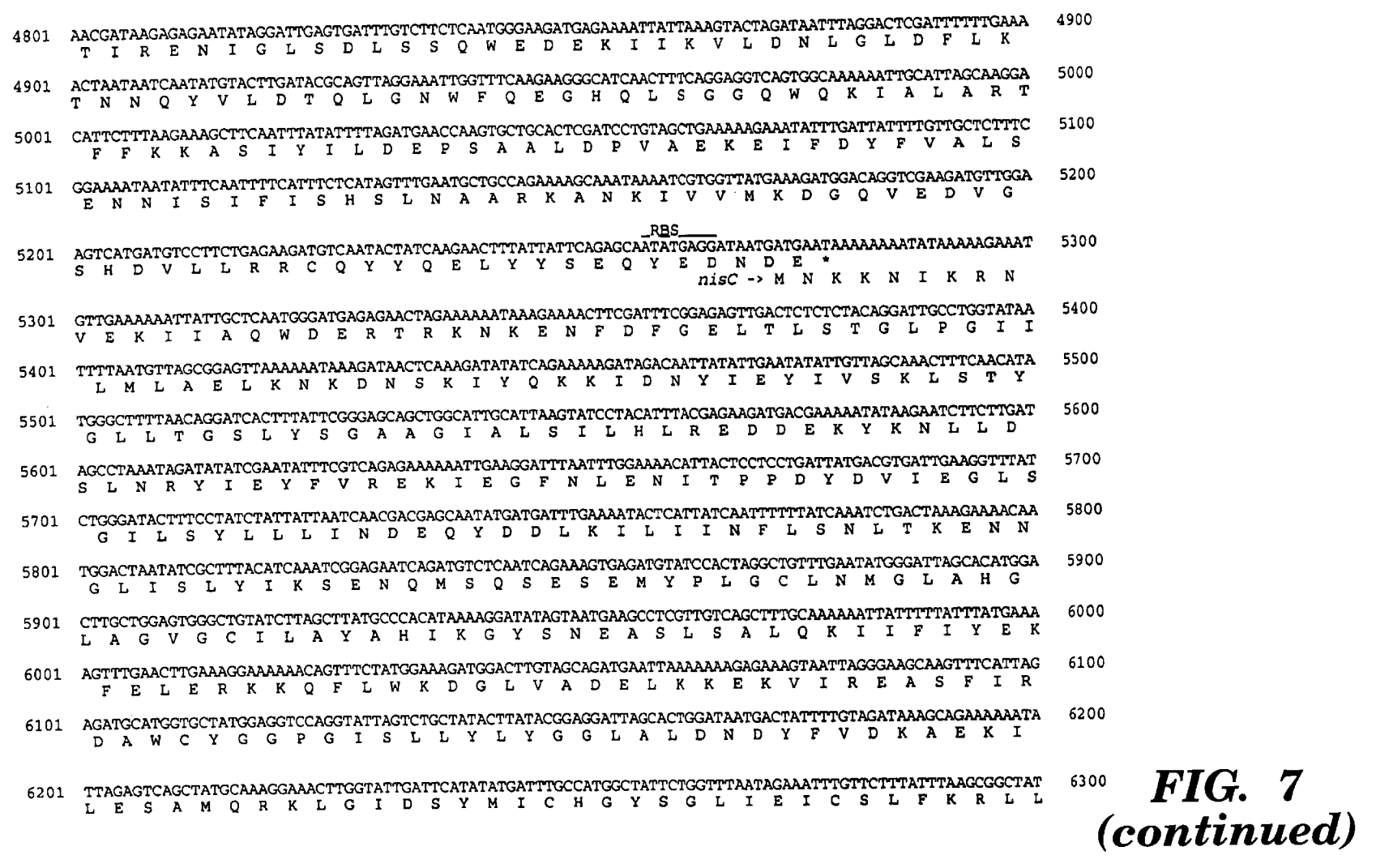
Figure 8:
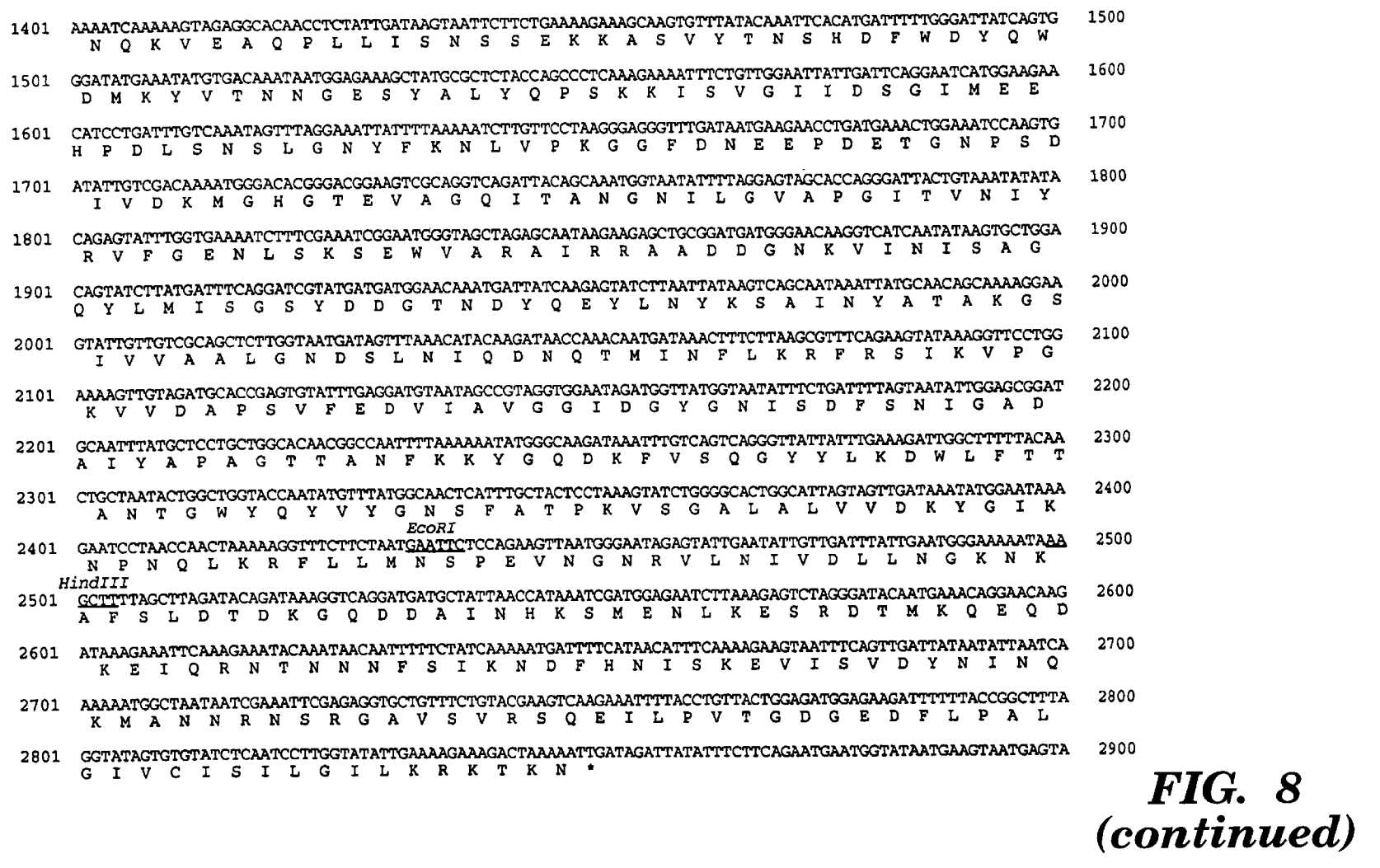
Figure 8:
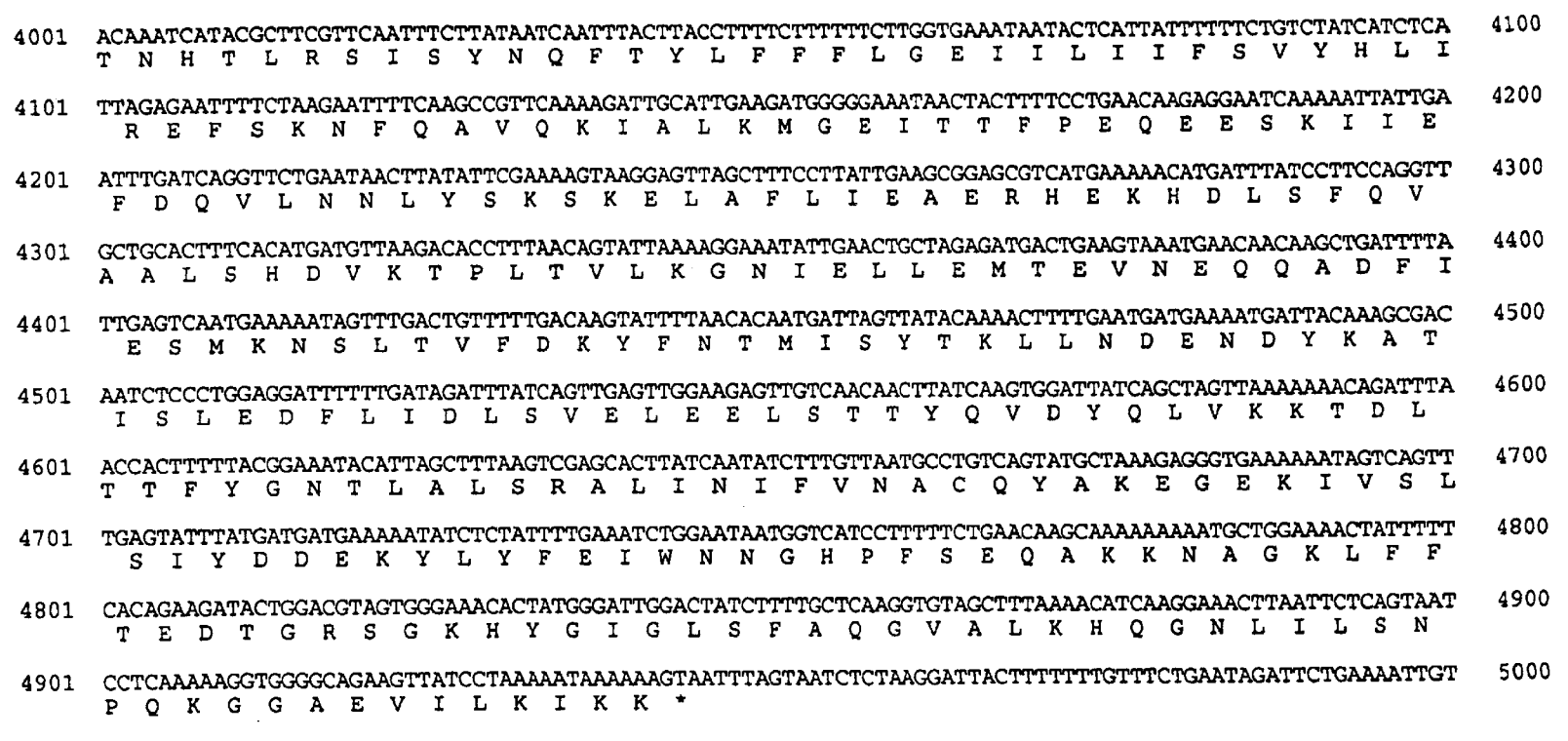

The nisA gene is the gene that encodes pre-nisin (pre-nisin includes a 23 amino acid N terminal signal sequence which is cleaved off during secretion); nisB and C are believed to be involved in reactions which modify the pre-nisin formed directly from expression of the nisA gene; nisT is similar to a transport ATPase and is involved in translocation of nisin out of the cell; nisP is involved in the extracellular processing of a fully matured precursor nisin; nisR and K encode regulatory proteins involved in gene expression and nisI is involved in immunity to nisin. The nucleotide sequence of the nisABTCIPRK gene cluster is shown in FIGS. 7 and 8.

Preferably the variant nisA gene occupies the same position as the natural nisA gene in the gene cluster. It is preferred if the cell is a lactococcal cell, most preferably the cell is a *Lactococcus lactis* cell. Suitable cells, especially Lactococcus cells, are readily available to the skilled person. Clearly it is required that they are a nisin producing cell, preferably a nisin producing, maturing and secreting cell but any such cells can be used. For example, the naturally-occurring nisin-producing strain NCFB894 as deposited in the National Collection of Food Bacteria at the Institute of Food Research, Norwich Laboratory, Norwich Research Park, Colney, Norwich NR4 7UA, UK (and as described in Gasson (1984) *FEMS Microbiol. Lett.* 21, 7–10) is a suitable Lactococcal cell for use in the methods of the invention.

Figure 1:
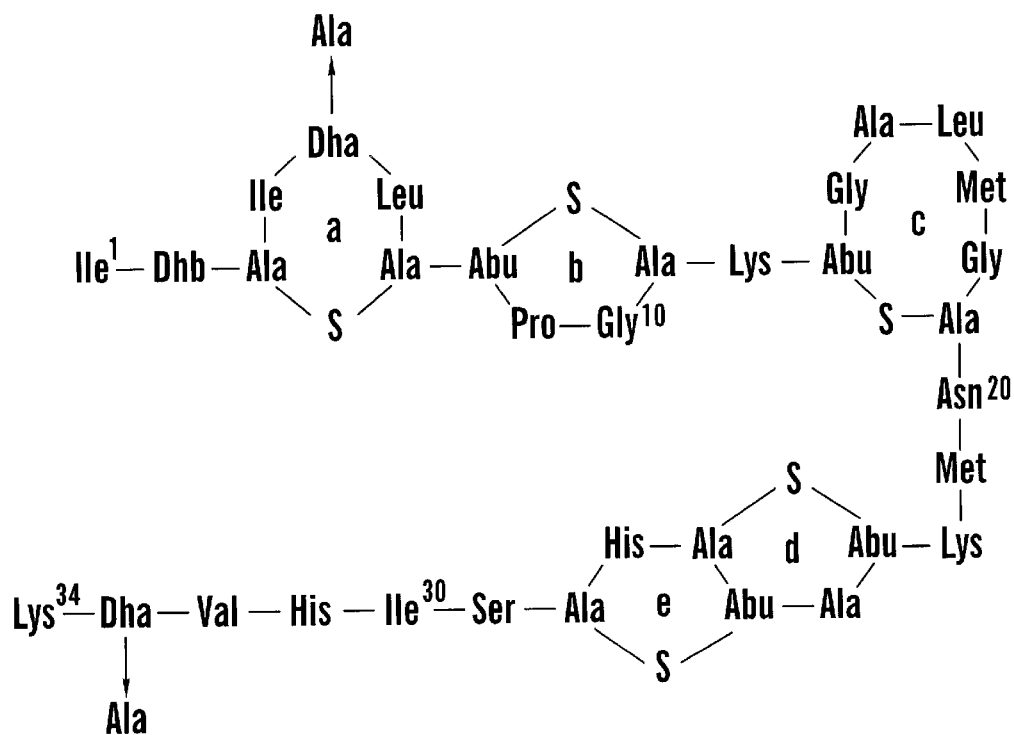
FIG. 1 shows the molecular structure of natural nisinA (SEQ. ID. No. 48). Changes that have been made to the sequence as a result of protein engineering are indicated by arrows: nisinA/Dha5A,Dha33A (SEQ. ID. No. 49); nisinA/Dha33A (SEQ. ID. No. 50); nisinA/Dha5A (SEQ. ID. No. 51).

By "natural nisA nisin" we include a peptide antibiotic produced by some naturally occurring nisin-producing strains of bacteria. The mature molecule is based on a sequence of amino acids encoded by a gene, nisA. The chemical structure of a natural nisA nisin is shown in FIG. 1. We also include in the term "natural nisA nisin" other naturally-occurring nisins that are based on, but vary from, the nisA nisin shown in FIG. 1. For example, we include nisin Z which has the same chemical structure as the nisA nisin shown in FIG. 1 except histidine in position 27 has been replaced by asparagine. The gene which encodes nisin Z was found to contain only one nucleotide substitution in comparison with the nisA gene which encodes the nisin A shown in FIG. 1.

By "elevated level of its natural nisA nisin compared to the natural level" we include a cell modified according to the method which produces at least 5% more, preferably 10% more, more preferably 50% more and most preferably >100% more natural nisA nisin than an unmodified cell when grown under the same culture conditions.

By "variant nisin" we include a protein-engineered variant of a natural nisA nisin in which changes to the amino acid sequence have been made as a result of site-directed or random mutagenesis of a nisA gene. Conveniently, one or more missense mutations are introduced into the protein coding region which result in one or more amino acids being substituted for another. Alternatively, a nonsense mutation can be introduced such that a truncated nisin is produced. In this case, the nisin still retains antibiotic activity. As a further alternative, deletions and/or insertions of the nisA gene can be made so long as the resulting nisin still retains antibiotic activity.

Site-directed mutations of the nisA gene may be made, for example, by the oligonucleotide-directed mutagenesis technique of Zoller & Smith (1983) *Meth. Enzymol.* 100, 468–500 and Zoller & Smith (1984) DNA 3, 479–480 which uses mismatched oligonucleotide primers to introduce the mutation. It is convenient to use a method for improving the yield of mutants, for example, the dut-ung method described by Kunkel (1985) *Proc. Natl. Acad. Sci. USA* 82, 488–492. Alternatively, the polymerase chain reaction (PCR) may be used to generate mutants using mismatched oligonucleotides (Saiki et al (1988) *Science* 239, 487–491). Random mutants of the nisA gene can be made chemically using, for example, sodium bisulphite or hydroxylamine as the mutagen. Alternatively, random mutations can be introduced into the nisA gene using enzymatic misincorporation using a DNA polymerase with relatively low fidelity, for example AMV reverse transcriptase or Taq DNA polymerase or by using mixtures of oligonucleotides, spiked during synthesis, to incorporate a small amount of each different bases at each position. These methods are well known in the art.

By "variant nisA gene" we include fragments of a nisA gene wherein the said fragments vary when compared to the equivalent part of the natural nisA gene.

By "variant nisA gene" we do specifically include genes in which the promoter region of the natural nisA gene is replaced by another (heterologous) promoter, preferably one which is known to be a more powerful promoter than the natural nisA gene promoter. Examples of suitable promoters are the inducible lacA promoter (van Rooijen et al (1992) *J. Bacteriol.* 179, 2273–2280) and the T7 promoter (Wells et al (1993) *Mol. Microbiol.* 5, 1155–1162), both papers being incorporated herein by reference.

We also include in the term "variant nisA gene" genes in which the ribosome binding region of the natural nisA gene is modified, preferably to improve the efficiency of initiation of translation of the nisA coding region.

Also included in the term "variant nisA gene" are genes which have silent mutations in the coding region, that is genes in which one or more codons are changed for their synonym, but that the natural nisA nisin is encoded thereby. Efficiency of translation may be improved by using such variant nisin coding regions. We also include genes which comprise a heterologous promoter to drive transcription of a variant coding region, that is, a promoter other than the natural nisA gene promoter.

In all cases, it is preferred that the combination of promoter, ribosome binding site and coding region gives optimal expression of the nisin encoded by the coding region.

Variant nisins which have improved properties compared with natural nisA nisin are preferred, for example those variant nisins which have more potent antimicrobial activity or that have greater resistance to hydrolysis or degradation when added to foodstuffs. Variant nisins are described in WO 93/20213 and WO 92/18633 (incorporated herein by reference), and in the Examples that illustrate the present invention.

A preferred embodiment of the invention provides a method for making a cell which either (a) does not express its natural nisA nisin but expresses a variant nisin or (b) expresses an elevated level of its natural nisA nisin compared to the natural level and, in either case, is capable of expressing genes for nisin modification and immunity comprising the step of substituting a variant nisA gene or part thereof for the natural, chromosomal nisA gene or part thereof at the chromosomal location of the said natural nisA gene.

The variant nisA gene or part thereof can be substituted for the natural, chromosomal nisA gene or part thereof at the chromosomal location of the said natural nisA gene in one step by gene replacement. Conveniently, a plasmid containing the variant nisA gene or part thereof is introduced into a host cell containing a chromosomal copy of the natural nisA gene (and preferably the genes for nisin modification, immunity and translocation of nisin out of the cell). A double cross-over recombination event can lead to the natural nisA gene or part thereof being replaced by the variant nisA gene or part thereof. The resulting cell will contain a chromosomal copy of the variant nisA gene and hence produce variant nisin provided that the variant nisA gene comprises a coding region which has been modified.

It is not necessary that the whole of the nisA gene is replaced. Rather, it is convenient that a or the part of the nisA gene that encodes the amino acid changes present in the variant nisin or contains the heterologous promoter is replaced.

The nisA gene, and other genes necessary for nisin biosynthesis, maturation and secretion are, in nature, located on a transposon which is part of the chromosome. Thus, chromosomal location refers to the presence of the nisA gene in the chromosomal DNA within the nisin gene cluster (nisABTCIPRK) rather than the position of the gene cluster relative to other genetic markers on the chromosome.

It is well known that homologous recombination occurs very inefficiently and unpredictably in Lactococcus and, although the above described direct, one-step method is feasible, it is more preferred if the gene replacement is carried out in an indirect, two step process in which it is possible to select for the desired recombinants as now described:

A further preferred method comprises the steps of (1) substituting a counter-selectable nisA gene or part thereof for the natural, chromosomal nisA gene or part thereof at the chromosomal location of the said natural nisA gene and (2) substituting a variant nisA gene or part thereof for the counter-selectable nisA gene or part thereof at the chromosomal location of the said natural nisA gene.

By "counter-selectable nisA gene" we include a nisA gene modified so that it is readily distinguishable from either the natural nisA gene or from a variant nisA gene.

Conveniently, the counter-selectable nisA gene is a nisA gene in which an antibiotic resistance gene (such as that for erythromycin resistance) has been inserted or is a nisA gene in which some or all of the coding region has been deleted. It is preferred, but not necessary, that the counter-selectable nisA gene does not express nisin.

It is not necessary that the whole of the nisA gene is replaced. Rather, it is convenient that a or the part of the nisA gene containing the counter-selectable marker is replaced.

In these examples the counter-selectable nisA gene can be distinguished from the natural or variant nisA gene by resistance to antibiotic of the counter-selectable gene and/or by size differences.

Thus, it is relatively straightforward to determine whether step 1 of the preferred method has been achieved because the resulting cell will, for example, have gained antibiotic resistance or, if the counter-selectable nisA gene has a deletion, specific fragments of the cell's chromosomal DNA will be missing or reduced in size.

Whether a specific fragment of a cell's chromosomal DNA is missing or reduced in size can readily be determined using well known molecular techniques such as Southern blotting, polymerase chain reaction (PCR) analysis or restriction fragment length polymorphism (RFLP) analysis.

Similarly, it is relatively straightforward to determine whether step 2 of the preferred method has been achieved because the resulting cell will, for example have lost antibiotic resistance or gained a fragment of chromosomal DNA.

Conveniently, in this preferred embodiment, there is a selection associated with step 2. For example, it is preferred if the counter-selectable gene in step 1 comprises a deletion of all or part of the nisA coding region ($\Delta$nisA) and that in step 2 the correct replacement of the variant nisA gene is selected for. Thus, in a preferred method, a *Lactococcus lactis* strain, containing a $\Delta$nisA gene (made using step 1) is used in step 2. A thermosensitive shuttle vector (replication-permissive at low temperature but not at high temperature) is used to introduce the variant nisA gene into the chromosome of the $\Delta$nisA strain. For example, the $\Delta$nisA strain is transformed with a plasmid containing the variant nisA gene and a gene for antibiotic resistance, and the cell is incubated at the permissive temperature in the presence of antibiotic. The cell is then transferred to the non-permissive temperature in the presence of antibiotic and a single cross-over event results in the integration of the plasmid in the chromosome at the site of plasmid/chromosome homology (ie at the common regions of the $\Delta$nisA and variant nisA gene).

The cell is then transferred to the permissive temperature to allow plasmid replication. Recombination between homologous sequences flanking the integrated plasmid results in its excision from the chromosome. A second cross-over event occurs resulting in either sequences originating from the integrated plasmid (ie the variant nisA gene) or the original sequences (ie the counter-selectable nisA gene) being retained on the chromosome. As discussed above, the variant nisA gene and counter-selectable nisA gene can be distinguished, and cells containing the variant nisA gene are chosen.

Cells are cured of plasmid by culturing in the absence of antibiotic.

Figure 10:
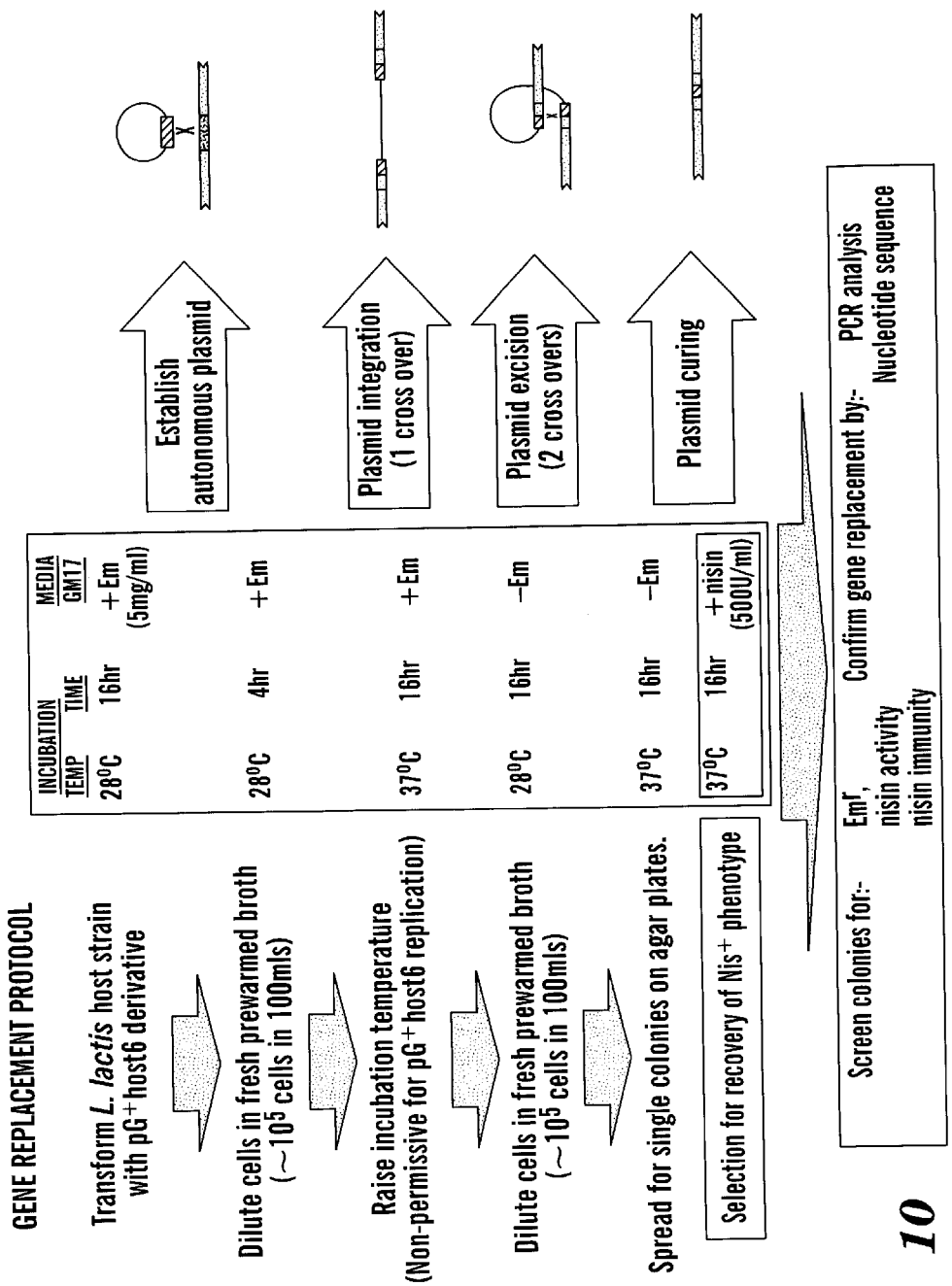
FIG. 10 describes diagramatically a gene replacement protocol.

In this preferred method the entire nisA gene and flanking sequences are effectively replaced with the identical sequences, with the exception of the specifically incorporated mutation. The size of the plasmid DNA fragment, containing the variant nisA gene is limited by the requirement for homologous sequences (on both the plasmid and chromosome) across which recombination can take place to bring about plasmid integration and subsequently, gene replacement. It is preferred for vector construction that there is approximately 1 kb of homology flanking the site of any sequence alteration. As an example our gene replacement vector has approximately 800 bp on one side of the nisA gene and 1,200 bp on the other. A reduction in this size would be expected to reduce the incidence of homologous recombination and therefore the chances of detecting the desired gene replacement. FIG. 10 illustrates the recombination events which occur during the preferred method.

The method of the invention results in cells which produce a variant nisin from a chromosomal copy of a variant nisA gene or a natural nisA nisin from a chromosomal copy of a variant nisA gene. As has been discussed above, it is most preferred if variant nisins have antibiotic activity. Thus, the cells will exhibit a Nis$^+$ phenotype because the cells produce a nisin (either natural or variant).

We have determined that these nisin-producing cells must necessarily also be immune to the nisin at the level at which they produce this antimicrobial peptide. Thus, a further preferred embodiment of the method comprises a further step of selecting those cells which are immune to nisin, at least to a level of 1000 U/ml.

Although it is preferred that the cells produced by the method express a variant nisin, the method also encompasses the making of a cell which can express natural nisA at a high level from a powerful, heterologous promoter.

In a less preferred embodiment, the gene cluster comprises a variant nisA gene and the genes for nisin modification and immunity and this gene cluster is carried on an autonomously replicating DNA element. Conveniently, the autonomously replicating DNA element is a plasmid. The host cell for the plasmid is a cell that does not express a natural nisA nisin. For example, a Lactococcal cell in which the natural nisin genes are absent or the natural nisA gene is inactivated.

Cloning the entire nisin gene cluster on a plasmid involves the integration of a large segment (~11 kb) of DNA. A strategy of this type has the advantage of enabling the copy number and therefore gene dosage to be altered and also may facilitate the transfer of nisin determinants to a range of alternative host backgrounds. There are two preferred types of replicons (which use different modes of replication) which can be employed as suitable vectors: the rolling circle plasmids (for example pTG262, Dodd et al (1990) *J. Gen. Microbiol.* 136, 555–566) or the theta type plasmids (for example, pIL253, high copy number, and pIL277, low copy number, Simon & Chopin (1988) *Biochimie* 70, 559–566). Both papers are incorporated herein by reference. When the method of the invention uses a lactococcal cell it is preferred if the plasmid is a shuttle plasmid, that is a plasmid that can replicate in the lactococcal cell and can also replicate in another host cell such as *Escherichia coli*.

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'–5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

A second aspect of the invention provides a cell which does not contain a natural nisA gene but expresses a nisin comprising a variant nisA gene wherein the variant nisA gene has the same relationship as the natural nisA gene to a gene cluster containing the natural nisA gene and the genes for nisin modification, secretion and immunity.

The cell of the second aspect of the invention is obtainable by the methods described in the first aspect of the invention.

In the most preferred embodiment the natural, chromosomal nisA gene or part thereof is absent and the cell comprises a variant nisA gene or part thereof at the chromosomal location of the said natural nisA gene.

Preferably the cell is a Lactococcus, most preferably *Lactococcus lactis*.

It is preferred that the cell expresses a variant nisin, although a cell that expresses an elevated level of natural nisA nisin also forms part of the invention.

Conveniently the variant nisA gene contains transcriptional or translational control sequences which enable the cell to either express a variant nisin or, in the case of natural nisA nisin, enable the cell to express it at an elevated level. Thus, in one embodiment the cell comprises a variant nisA gene consisting of a heterologous promoter which drives the expression of a nisin coding region (which may express a natural nisA nisin or a variant nisin).

In a less preferred embodiment the cell comprises an autonomously replicating DNA element carrying a variant nisA gene and the genes for nisin modification and immunity. In this case, the cell does not have an active chromosomal nisA gene and preferably no chromosomal nisin genes.

A third aspect of the invention provides a process for producing nisin comprising culturing a cell as described in the third aspect of the invention and obtaining the nisin produced thereby.

Conveniently, the nisin is a variant nisin.

It is preferred if the cells are those of the most preferred embodiment.

We have found that using the cells of the most preferred embodiment in the process we can produce an unexpectedly high yield of nisin particularly in comparison to the known processes which rely on plasmid-borne nisA genes to express the nisin (in the absence of plasmid-borne nisin immunity, modification and secretion genes). Further details of this surprising effect are given in the Examples. However, it is worth noting at this point that, in the case of a nisin variant in which both dehydroalanine 5 was replaced by alanine and dehydroalanine 33 was replaced by alanine (known as nisinA/Dha5A, Dha33A), the cell of the present invention in which the natural nisA gene is replaced by the variant nisA gene produces more than 100 times the nisin compared with a prior art cell in which the same variant nisin (nisinA/Dha5A, Dha33A) was encoded by a plasmid. In addition, all of the variant nisins that have been tested give a higher yield from cells of the present invention compared with the prior art cells containing the variant nisin gene on a plasmid.

Further advantages over the prior art methods and cells are obtained using the cells of the most preferred embodiment to produce nisin. For example, because the cells do not contain a plasmid there is no requirement for antibiotic selection during their culture and plasmid loss during culture is not a problem.

Thus, for stability there is an advantage in that the variant nisin gene is integrated within the bacterial chromosome albeit as part of the nisin transposon Tn5301. The latter is extremely stable and we have in fact found it difficult to eliminate deliberately. In the laboratory selection for a plasmid marker prevents this being a practical problem, but for industrial use this would be a disadvantage. It may be undesirable to add antibiotics to the fermentation.

In a less preferred embodiment, cells carrying the variant nisA gene and the genes for nisin modification and immunity are carried on an autonomously replicating DNA element, such as a plasmid. Clearly, in this embodiment, plasmid selection is required during the culture of the cell.

A particularly preferred embodiment of the third aspect of the invention is wherein the cells are cultured in the presence of nisA nisin or a variant nisin which can induce nisin expression. Nisin A wherein Ile30 is replaced by Trp (I30W) is an example of a variant that, as a result of its mutation, does not function well as an inducer of its own biosynthesis. By adding sub-inhibitory concentrations of nisin to the growth medium, during fermentation, higher levels of the variant nisin are produced. Any variants that are less efficient as inducing agents benefit from the inclusion of nisin in the growth medium (ie a nisin induction step in the purification procedure). The amount of induction varies depending on the initial induction capacity of any particular variant (with I30W nisin A production more than doubled as a result of induction). Induction may be routinely included in the method as a means of maximising production levels. Any concerns about contamination with the wild type molecule are minimal as the nisin concentration required for induction is negligible compared to the amount of nisin variant being purified. Conveniently, the nisA nisin is a minimum amount that provides maximal induction of nisin production. This amount can be determined empirically by a person skilled in the art. Suitable nisA nisin concentrations for induction in this embodiment are from 1 nM to 500 nM, preferably 10 nM to 250 nM, more preferably 50 nM to 150 nM, most preferably 100 nM.

A reverse-phase HPLC step in any purification would ensure separation of any residual nisA nisin from variant nisins.

A fourth aspect of the invention provides a nisin produced by the process of the invention.

The presence of unsaturated amino acids in lantibiotics including nisin and the role they play in the biological properties of these complex molecules is of particular interest in structure/function analyses. It has been proposed that the reactive unsaturated bonds that characterise dehydro-amino acids play a functional role in the antimicrobial activity that subtilin, a lantibiotic, exerts against bacterial spore outgrowth. These residues have also attracted attention as a possible source of molecular instability. It has long been known that the antimicrobial activity of commercial samples of natural nisA nisin deteriorate on storage and that a number of chemical components are found within such samples (Berridge et al, 1952) and Chan et al (1989) have demonstrated that specific cleavage occurs at the dehydroalanine residues in the mature molecule. Cleavage at Dha5 results in the opening of the first lanthionine ring of nisin and is accompanied by a loss of antimicrobial activity. In contrast, the degradation product arising as a result of cleavage at Dha33 retains essentially wild type activity (Chan et al, 1989).

In WO 93/20213 we described the construction of L. lactis derivatives expressing nisinA/Dha5A, nisinA/Dha33A and nisinA/Dha5A,Dha33A. We also demonstrated in that work that these engineered nisins retained their antimicrobial activity against sensitive indicator strains. Clearly, as described in detail in the Examples, these nisins can be produced more efficiently by the present process. However, the present process can also be used to produce any further variant nisins which have other, improved properties so long as they are encoded by a variant nisA gene.

A fifth aspect of the invention provides the use of a nisin produced according to the process of the invention as an antimicrobial agent. The ability of nisin to inhibit growth of spoilage bacteria and food pathogens has resulted in the extensive use of as a natural preservative in certain food products, particularly dairy products such as soft cheeses. Variant nisins are also used.

EXAMPLES

The invention will now be described in more detail with reference to the figures and following examples.

Example 1

Construction of Lactococcal Cells in which the Natural, Chromosomal nisA Gene is Replaced by a Variant nisA Gene Methods
Microbiological Techniques and Strains Used.

The Lactococcal strains used in this study and their derivation are given in Table 1.

TABLE 1

Lactococcal strains used in this study:

| Strain | nisA mutation | Activity | Immunity (U/ml × $10^3$) | Reference |
|---|---|---|---|---|
| MG1614 | — | − | 0.01 | Gasson (1983) J. Bacteriol. 154, 1–9 |
| FI5876 | wild type | + | >1 | Dodd et al (1990) J. Gen. Microbiol. 136, 555–566; Horn et al (1991) Mol. Gen. Genet. 228, 129–135 |
| FI7847 | nisA-(fs) | − | 0.5–0.75 | This work |
| FI7990 | ΔnisA | − | 0.25–0.5 | This work |
| FI8070 | nisA/S5A | + | >1 | This work |
| FI8198 | nisA/S33A | + | >1 | This work |
| FI8199 | nisA/S5A, S33A | + | >1 | This work |
| FI7893 | nisA | + | >1 | This work |
| FI8003 | nisA | − | 0.25–0.5 | This work |

Unless stated otherwise, cultures were grown at 30° C. in M17 medium (Terzaghi & Sandine (1975) Appl. Environ. Microbiol. 29, 807–813) supplemented with 0.5% (wt/vol) glucose (GM17 medium). Screening strains for resistance to antibiotics was carried out at the following levels: erythromycin, ($Em^r$ 5 μg/ml; streptomycin, ($Sm^r$) 200 μg/ml.

Escherichia coli MC1022 (Casadaban & Cohen (1980) J. Mol. Biol. 138, 179–207 was the host strain for construction and molecular analysis of recombinant plasmids derived from the vectors pMTL23p (Chambers et al (1988) Gene 68, 139–149), pGEM-3Z (Promega), pCR™II (Invitrogen) and pG+host6 (Appligene). Recombinant plasmids used, and constructed during the course of this study, are shown in FIG. 2. E. coli cultures were propagated at 37° C. in L broth (Lennox (1955) Virology 9, 190–206. Selection for ampicillin resistance ($Ap^r$) was carried out at 100 μg/ml, chloramphenicol ($Cm^r$) at 15 μg/ml and erythromycin, ($Em^r$) at 400 μg/ml.

Nisin activity in Lactococcal strains was assayed by both deferred and direct means. Plate diffusion bioassays were performed as previously described (Dodd et al (1992) Appl. Environ. Microbiol. 58, 3683–3693. Colonies growing on the surface of a GM17 plate were directly assayed by inverting over chloroform for 12 minutes and overlaying with agar seeded with the nisin sensitive L. lactis strain MG1614. Plates were incubated overnight and zone sizes around colonies compared with those of controls. Nisin immunity was determined by streaking cultures on a series of GM17 agar plates containing an increasing concentration of nisin and assessing the degree of growth at the different nisin levels. Control cultures (FI5876, positive) and MG1614 (negative) were included on each plate.

Molecular Techniques

Total DNA, plasmid DNA was carried out as described by Dodd et al (1990) J. Gen. Microbiol. 136, 555–566 and Horn et al (1991) Mol. Gen. Genet. 228, 129–135. Restriction enzyme and other DNA modifying enzymes from various sources were used according to the suppliers recommendations. Recombinant plasmids were recovered by transformation of E. coli as described previously (Dodd et al (1992) supra or electroporation of L. lactis according to Holo and Nes (1989) Appl. Environ. Microbiol. 55, 3119–2123 with the modifications of Dodd et al (1992) supra. Conditions used for polymerase chain reaction (PCR) were as described in Horn et al (1991) *Mol. Gen. Genet.* 228, 129–135. Primers were synthesised on an Applied Biosystems DNA synthesizer (model 381A) and are listed in Table 2. Fragments generated for the construction of gene-replacement vectors were amplified using Dynozyme (Flowgen) and cloned into pCR™II prior to nucleotide sequence confirmation. For routine PCR screening of recombinant clones AmpliTaq-DNA polymerase (Perkin Elmer) was used. Direct nucleotide sequence determination of purified PCR-generated templates was carried out on an Applied Biosystems DNA Sequencer (model 373A) using the manufacturers' Taq "Dyedeoxy" terminator cycle sequencing kit.

TABLE 2

Primers used in this study:

P13 (SEQ ID No 1) 5'-AACGGATCCGATTFAAATTCTGAAGTTTG-3'
         BamHI

P17 (SEQ ID No 2)
5'-TCAGAGCTCCTGTTTTACAACCGGGTGTACATAGTGCAAT-3'
P18 (SEQ ID No 3) 5'-TAGTATTCACGTAGCTAAATAACC-3'
P19 (SEQ ID No 4) 5'-TTGGTTATTTAGCTACGTGAATAC-3'
P25 (SEQ ID No 5) 5'-AATCGGATCCGTTTATTATGCTCGC-3'
         BamHI

P26 (SEQ ID No 6) 5'-ATAGTTGACGAATATTTAATAATTTT-3'
         HincII

P27 (SEQ ID No 7) 5'-CTTGGTCGACACCCATATTTT-3'
         SalI

F28 (SEQ ID No 8) 5'-GTTAGATCTGACATGGATAC-3'
         BglII

P32 (SEQ ID No 9) 5'-CCATGTCAGATCTAACAAAATAC-3'
         BglII

P39 (SEQ ID No 10) 5'-GACTTTCCATTATGCTTGGATTTTT-3'
P40 (SEQ ID No 11) 5'-GCTCCTATGCCAAATGTAGAATC-3'

Construction of nisA Gene Replacement Vectors

Figure 3:
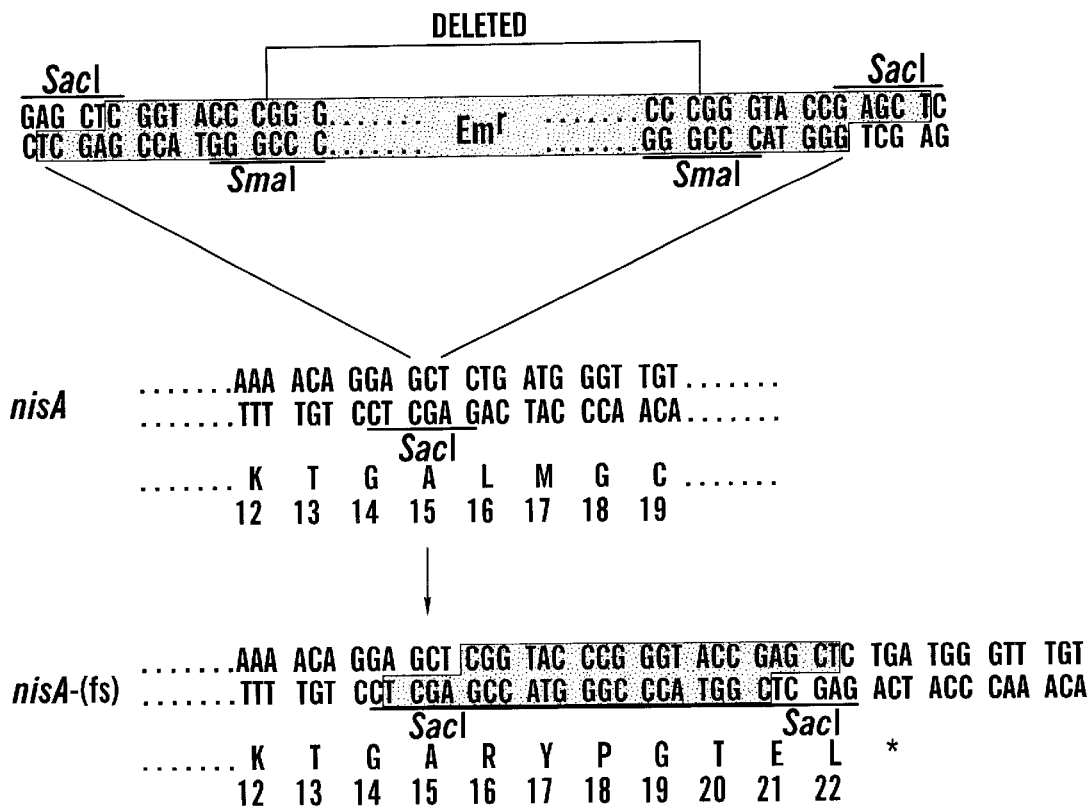
FIG. 3 shows diagramatically counter-selectable nisA genes wherein either an erythromycin resistance gene is inserted in a nisA gene or a frame-shift deletion has been made (nisA-fs). The sequences shown are in the sequence listing as SEQ. ID. Nos. 12 to 17.

The thermosensitive shuttle vector pG+host6 was employed for carrying out gene replacement. Homologous plasmid DNA originated from pFI172 (Dodd et al (1990) supra) which contains a 2.1 kb region of the FI5876 chromosome (FIG. 2a) including the nisA gene. The entire fragment was subcloned into pG+host6 to generate the nisA gene-replacement vector pFI690 (FIG. 2b). Subsequent manipulation of this region, resulting in inactivation or mutagenesis of the nisA gene (see below), was carried out in either vector pGEM-3Z or pMTL23P. The final step in the construction of each gene-replacement vector was cloning the modified 2.1 kb fragment into pG+host6. The derivatives of pG+host6 were established in *E. coli* and plasmid DNA, from this host, used to transform *L. lactis* FI7990 (Table 1).

nisA Frame Shift Mutation—nisA-(fs):

Insertional inactivation of the nisA gene, by cloning an Em$^r$ gene into the internal SacI site, has been described previously (Dodd et al (1992) supra). In this plasmid the Em$^r$ gene is flanked by a short multiple cloning site (FIG. 3) (SEQ ID Nos. 12, 13). Digestion with the restriction enzyme SmaI, followed by ligation to recircularise the vector sequences, resulted in deletion of the Em$^r$ gene. Residual sequences from the multiple cloning site leave a 20 bp insertion within the SacI site and cause a frameshift mutation to occur in codon 16 of the nisA gene (SEQ. ID. Nos. 14, 15). The first 38 amino acids encoded by this mutated gene [designated nisA-(fs), SEQ. ID. No. 16] are unaffected. However, the predicted translation product would be a truncated prenisin (45 residues) (SEQ. ID. No. 17) including the on-nisin amino acid sequence RYPGTEL (SEQ. ID. No. 18) at its COOH-terminus (FIG. 3). The nisA-(fs) mutation was subcloned into pG+host6 to generate the gene replacement vector pFI674 (FIG. 2c).

nisA Deletion—ΔnisA:

Inactivation of the nisA gene was also achieved by deletion of the coding region. In order to confine the deletion to just nisA it was necessary to engineer additional restriction enzyme sites on either side of the gene. Primers were designed, for PCR amplification of this region of the chromosome, that incorporated a BamHI site (P13, Table 2) 80 bp upstream of the start of nisA and a BglII site (P32, Table 2) 25 bp beyond the stop codon, as a result of 2 bp changes in each case (FIG. 3). The flanking fragments (shown in FIG. 2d) were also generated using PCR amplification. Primers P26 and P25 were employed for amplification of the upstream 211 bp HincII/BamHI fragment and primers P28 and P27 employed for the downstream 1.1 kb BglII/SalI fragment (Table 2). The template used for these PCR reactions was pFI172 DNA. The resulting plasmid (pFI740) contained an intact nisA gene flanked by an engineered BamHI and BglII sites, all contained within 2.1 kb of sequences homologous to the chromosome (FIG. 2d). Digestion of pFI740 with these two enzymes, followed by ligation of their compatible ends, resulted in the generation of plasmid pFI751 in which the nisA gene has been deleted, designated as ΔnisA (FIG. 2e). PCR amplification of this part of the plasmid and nucleotide sequence analysis of the region spanning the deletion in the amplified fragment confirmed that fusion of the BamHI and BglII sites had occurred.

nisA Site-specific Mutations:

The construction of the plasmid pFI877 (FIG. 2f) allowed a cassette mutagenesis strategy to be employed for the introduction of site-specific mutations into the nisA gene. This pGEM-3Z derivative contains the equivalent sequences to those in pFI690 (FIG. 2b), but includes the engineered BglII site downstream of nisA in pFI740 (FIG. 2d). In pFI877 a HincII/SacI fragment encoding the amino-terminal region of nisA and upstream expression signals, replaced the PCR-generated fragment of pFI740 that contains the engineered BamHI site. Thus, the only difference between sequences in pFI877 and the equivalent chromosomal wild-type sequences is the presence of an additional BglII site downstream of the nisA gene. The construction of this nisA cassette is such that site-specific mutations could be readily incorporated into the gene. PCR-mediated mutagenesis was used to amplify either the HincII/SacI or SacI/BglII fragments containing the amino- or COOH-terminal regions of the nisA gene respectively (FIG. 2f). These fragments, containing a specific mutation, were then substituted for the wild-type fragment of pFI877. Mutations were incorporated in either the primers used to amplify the cassette fragments or, if the desired site of mutation was internal, the technique of spliced overlap extension was used (Ho et al (1989) *Gene* 77, 51–59) with the specific mutations incorporated on two complementary primers spanning the mutation site (Dodd et al (1992) supra).

Gene Replacement Protocol

Figure 9:
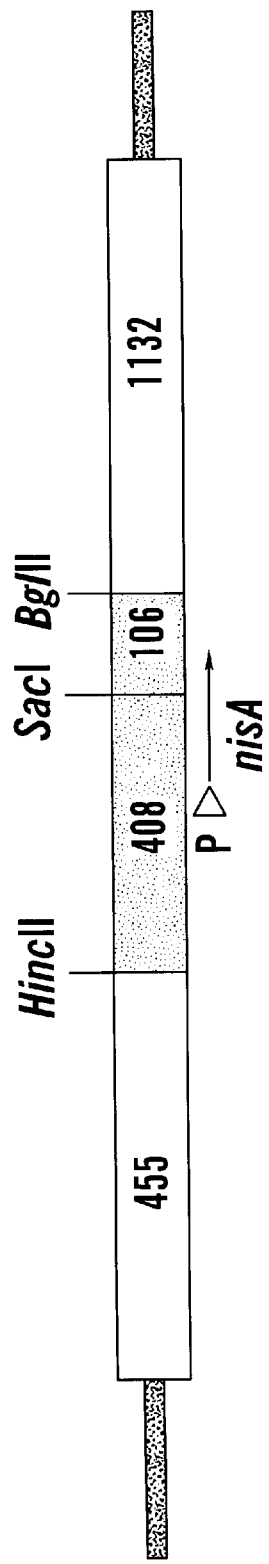
FIG. 9 illustrates a gene replacement vector. Sizes of the cloned fragments that make up the nisA cassette and flanking sequences are given in base pairs.

*L. lactis* FI7990 transformants containing derivatives of pG+host6 were established at 28° C. and grown overnight at this temperature in GM17 containing Em at 5 μg/ml (GM17-Em). Approximately $10^5$ cells were used to inoculate 100 ml of fresh, prewarmed GM17-Em and the cultures were incubated at 28° C. for 4 hours. Incubation was continued overnight at the elevated temperature of 37° C. This temperature is non-permissive for pG+host 6 replication (Biswas et al (1993) *J. Bacteriol.* 175, 3628–3635) and the presence of Em in the growth media ensures selection for those cell lines in which a single cross-over results in the integration of the derivative in the chromosome at the site of plasmid/chromosome homology (Leenhouts et al (1989) *Appl. Environ. Microbiol.* 55, 394400; Leenhouts et al (1990) *Appl. Environ. Microbiol.* 56, 2726–2735; Chopin et al (1989) *Appl. Environ. Microbiol.* 55, 1769–1774). Prewarmed GM17 (with no Em) was inoculated with approximately $10^5$ cells from the overnight culture and incubated overnight at 28° C. At this temperature plasmid replication is possible and recombination between homologous sequences flanking the integrated plasmid results in its excision from the chromosome. Depending on where the second cross-over occurs either sequences originating from the integrated plasmid, or the original sequences will be retained in the chromosome. The lengths of DNA homology are shown in FIG. 9. These sequences originated as an AccI/SalI fragment making up part of a SalI fragment that is cloned and sequenced in the plasmid pFI 172 (Dodd et al (1990) *J. Gen. Microbiol.* 136, 555–566).

Cultures were diluted and spread, for single colonies, on GM17 agar plates. In order to cure the cells of plasmid, the plates were incubated at 37° C. Colonies (approximately 50) were screened for loss of the pG+host6 derivative by patching onto GM17 plates containing Em (5 µg/ml). When using this technique to disrupt the nisA gene colonies were also screened for loss of nisin activity and PCR analysis of the relevant region of the chromosome used to confirm any changes at the molecular level.

The gene replacement protocol is illustrated diagrammatically in FIG. 10.

RESULTS

Inactivation of Chromosomally Encoded FI5876 nisA Gene

In order to identify cell lines that have acquired variant nisA genes it was convenient to first construct a Nis⁻ host strain, by inactivating the resident nisA gene. The well characterised nisin-producing strain *L. lactis* FI5876 was selected for this purpose (Dodd et al (1990) supra; Horn et al (1991) supra). The nisin biosynthesis genes from this strain have been cloned and sequenced (Dodd et al (1992) supra).

Gene-replacement was used to substitute the wild-type nisA gene of FI5876 with the plasmid pFI674-encoded nisA-(fs) gene (FIG. 2c, FIG. 3). Of fifty colonies screened five were both Em$^s$ and Nis⁻ suggesting that in these FI5876 derivatives gene replacement had occurred. Furthermore, this result indicated that the modified nisA gene, was defective and did not express a precursor molecule that could be matured to an active form. One of the Nis⁻ strains, designated FI7847, was analysed further. To test the system it was demonstrated that the nisA-(fs) mutation in FI7847 could be reverted back to wild-type by carrying out the equivalent experiment using the nisA gene replacement vector pFI690 (FIG. 2b). Recovery of nisin production by the resulting gene-replaced strain, FI7898, indicated that the Nis⁻ phenotype exhibited by FI7847 was due solely to disruption of the nisA gene. The other nisin biosynthesis determinants appeared to have been unaffected by the switching of nisA genes.

Figure 5:
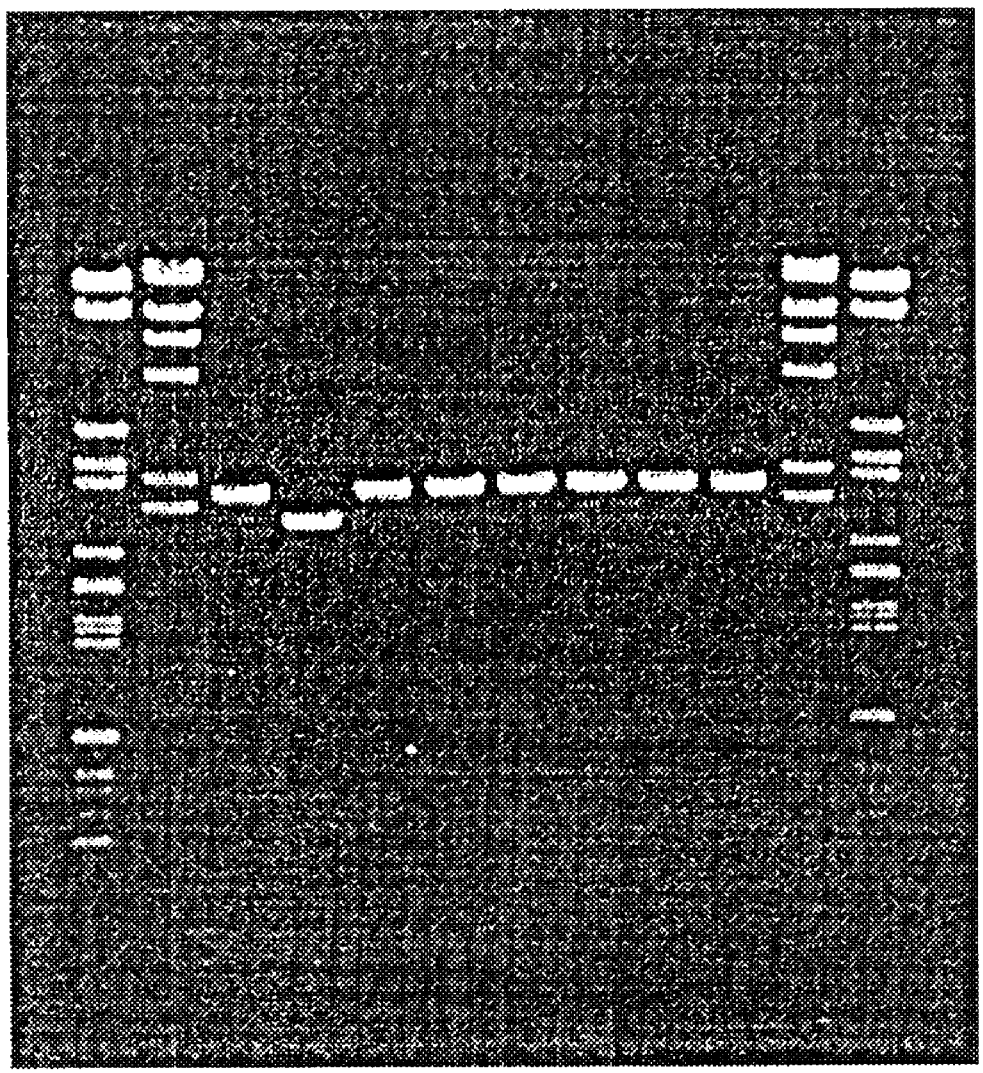
FIG. 5 shows an agarose gel electrophoresis of PCR fragment generated with primers P39 (SEQ. ID. No. 10) and P40 (SEQ. ID. No. 11). PCR reactions were carried out on colonies of: track 3, FI5876; 4, FI7990; 5–10, FI7990 (pG host6 derivative) after gene replacement procedure. Size standards: tracks 1 and 12, λDNA digested with BglI; 2 and 11, λDNA digested with HindIII.

An alternative approach was to generate a Nis⁻ host by deletion of the entire chromosomal nisA gene in FI5876. Plasmid pFI751 (FIG. 2e) was constructed for this purpose and gene replacement used to incorporate the approximate 300 bp deletion ΔnisA (FIG. 4) in place of nisA. Nis⁻ strains were recovered at about the same frequency as was found with the nisA-(fs) gene-replacement. In this case the ΔnisA containing strains could be readily distinguished from the parent strain by PCR analysis. Primers P39 and P40 (Table 2, FIG. 2a) amplified a 1.8 kb fragment in the gene-replaced strains (FIG. 5, track 4) compared to a 2.1 kb fragment generated from the equivalent region of FI5876, encoding wild-type nisA (FIG. 5, track 3). In one of the Nis⁻ strains, designated FI7990, nucleotide sequence analysis of the PCR-generated 1.8 kb fragment confirmed that ΔnisA was incorporated in the correct region of the chromosome. Again the system was tested and it was shown that nisin production could be restored in a FI7990 derived strain by gene replacement with pFI690 (FIG. 2b). PCR analysis of these Nis⁺ colonies demonstrated that the ΔnisA mutation (1.8 kb fragment) had been replaced by the wild-type nisA gene (2.1 kb fragment). As this system has the advantage of being able to readily identify gene-replacement on the basis of PCR analysis (see FIG. 5) further characterisation and mutant construction was carried out using FI7990 as the host strain.

Nisin Immunity

The effect of disruption of the nisA gene on immunity of the host strain to nisin has been described previously (Dodd et al (1992) supra). As would be expected both FI7847 [nisA-(fs)] and FI7990 (ΔnisA) displayed reduced immunity to nisin (Table 1). The nisA deleted strain FI7990 was sensitive to nisin at a concentration of between 250 and 500 U/ml compared to the parent strain, FI5876, which will continue growing in the presence of nisin to over 1000 U/ml. Interestingly, FI7847, encoding a truncated nisA gene, exhibited intermediate levels of immunity to nisin (an upper limit of between 500 and 750 U/ml with poor growth continuing to 1000 U/ml, Table 1).

A possible explanation for the difference in nisin sensitivity of these two Nis⁻ strains came from gene replacement studies involving the vector pFI740 (FIG. 2d). Strain FI8003, generated by substitution of the defective nisA gene with the intact plasmid pFI740-encoded nisA, had a Nis⁻ phenotype. This result contrasts with that of the equivalent gene replacement experiment, involving pFI690 (FIG. 2b), in which a Nis⁺ phenotype was recovered (see above). The only difference between the two sequences involved is that pFI740 has an additional BamHI site incorporated 80 bp upstream of the ATG start codon of nisA, and a BglII site immediately downstream of the coding region (FIG. 4). Examination of these sequences revealed that the BamHI site overlaps with the proposed -35 region of the promoter identified by Kuipers et al (1993) *Eur. J. Biochem.* 216, 281–291. A single base pair change introduced as a result of engineering the BamHI site has the effect of converting the -35 sequence from CTGATT to CCGATT (FIG. 4).

These results suggest that in pFI740 the natural nisA promoter has been disrupted and hence, those strains, such as FI8003, which have incorporated the BamHI site by gene replacement will also have acquired the defective promoter. The increased nisin sensitivity of these strains (approximately 50% that of wild-type), despite an intact nisA gene, suggest that these potentially promoter active sequences play a role in nisin immunity.

The preferred protocol uses nisin immunity as a means of directly selecting Nis⁺ strains that have undergone gene replacement and relies on the fact that inactivation of the nisA promoter in FI7990 results in a sufficiently high sensitivity to nisin that the parent strain will not grow on the selective plates. Nis⁻ strains that retained the upstream promoter sequences (eg FI7847) were unsuitable for this procedure as they grew well at the levels of nisin that were found to be optimal for selection of Nis$^+$ recovery, ie 500 U/ml (Table 1).

Gene Replacement—Identification of Variant nisA-encoding Strains

From the preliminary gene-replacement experiments carried out in the construction and testing of the Nis$^-$ strains FI7847 and FI7990 it was known that substitution of chromosomal sequences for the equivalent homologous region carried by the pG+host6 derivative, occurred at low frequency. The subsequent restoration of an intact nisA gene in these hosts, by gene replacement, would be expected to lead to the recovery of nisin activity. Any Nis$^+$ strains within the population would then be at a selective advantage over the original Nis$^-$ parent. However, initial attempts to recover an activate nisA gene again resulted in the majority of colonies screened retaining the defective nisA parental sequences.

The restoration of a Nis$^+$ phenotype necessitates a functional nisin immunity mechanism and this requires the expression of the nisA gene. The gene-replacement protocol, employed for the construction of FI7847 and FI7990, was modified to facilitate the identification of derivatives that had acquired nisA or variant nisA genes that resulted in nisin production. The recovery of a Nis$^+$ colonies hinged on our interpretation that these cells must necessarily also be immune to nisin at the level at which they were producing this antimicrobial peptide. In the modified gene replacement protocol the final step included the addition of nisin to the GM17 agar plates, at a level of 500 U/ml. Nisin immune colonies that grew on this media were screened for Em$^r$ and assayed for nisin production. PCR analysis was also used to determine the organisation of genomic sequences. FIG. 5 shows the fragments generated by PCR (using primers P39 and P40, FIG. 2*a*) from six colonies that had been through the gene replacement procedure. All were found to have acquired a functional copy of a nisA gene (in this case nisA/S5A) as shown by the 300 bp increase in size of the PCR fragment. This procedure was found to be a very reliable means of identifying Nis$^+$ derivatives of FI7990 as this host strain was itself sensitive to the levels of nisin employed in the selection plates. The majority of colonies (approximately 90%) screened in this way were found to have undergone gene-replacement and to be expressing a functional nisA gene or variant in place of the chromosomal lesion ΔnisA. This strategy has been successfully employed to select for several derivatives of FI7990 that are now exclusively expressing engineered nisins in place of nisin A.

As described above, the protocol involves the integration of the thermo-sensitive plasmid, p+Ghost6 in the chromosome, followed by its excision. Assuming that crossovers occur with equal frequency between homologous sequences on either side of the mutation, it would be predicted that the number of cells now carrying the mutation would be the same as those cells identical to the parent strain. This did not prove to be the case and the majority of colonies screened retained the genetic organisation of the parent strain FI7990. The reason for this is not clear, but it suggests that the immediate effect of integration of a functional nisA gene is detrimental to the host cell. It has been reported that expression of the nisA gene precedes that of the adjacent nisB gene by 30 minutes (Engelke et al (1994) supra) and transcription of other determinants in the nisin gene cluster may be similarly delayed, with respect to prenisin production. Those strains that acquire a nisA gene by gene-replacement may not have recovered full immunity before the nisin molecule exerts its antimicrobial action. Such strains would not be viable. However, we have been able to restore a Nis$^+$ phenotype by gene replacement when nisin production has been delayed allowing full nisin immunity to be established.

Conversion of Dha to Ala Residues

The dehydroalanine (Dha) residues at positions 5 and 33 (FIG. 1) were initially targeted for engineering changes in the nisin molecule. The aim was to substitute the serine residues, from which the Dhas are derived, for alanines which lack a potentially unstable unsaturated side chain. The mutation in nisA,S5A was generated by PCR using primers P26 and P17 (Table 2). Amplification resulted in a 404 bp HincII/SacI fragment containing the amino-terminal end of nisA and including the substitution of a Ser codon (coordinate 173, FIG. 4) for CGT which specifies alanine. The 90 bp SacI/BglII fragment containing the COOH-terminal end of nisA was generated by PCR using primers P10 and P32 (Table 2) and included a spliced overlap extension step with primers 18 and 19 (Table 2). This latter pair of complementary primers contain an alanine codon, CGT, in place of the serine codon at coordinate 257 (FIG. 4). Subcloning these PCR generated fragments, either separately or together, into the appropriate gene-replacement vector resulted in an uninterrupted coding region specifying either a nisA/S5A, nisA/S33A or nisA/S5A,S33A gene. Transformation of FI7990 with plasmid DNA followed by the gene-replacement procedure generated a number of colonies the majority of which were found to be Em$^s$ and Nis$^+$. The relevant region of the chromosome was investigated by PCR using the primer combination P39 and P40 (FIG. 2*a*) and in each case a 300 bp increase in fragment size, compared to FI7990 (see FIG. 5), indicated that gene replacement had occurred. Nucleotide sequence analysis of these PCR generated fragments confirmed that, in each case, the three variant nisA genes were incorporated in the chromosome, in place of the ΔnisA lesion. A representative of each gene-replaced strain, FI8070 (nisA/S5A), FI8198 (nisA/S33A) and FI8199 (nisA/S5A,S33A) was characterised further.

Figure 6:
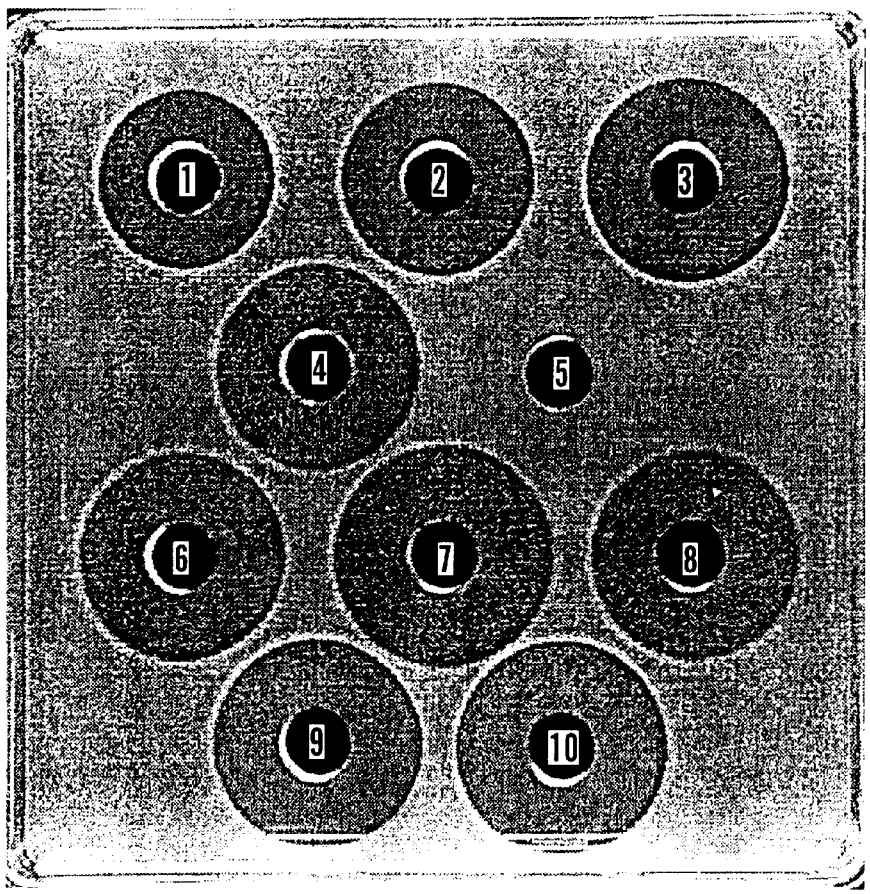
FIG. 6 shows a plate diffusion bioassay. 150 µl samples of cell free extracts from strains: 4, FI5876; 5, FI7990; 6, FI8070; 7, FI8198; 8, FI8199 were loaded into wells bored in MRS agar seeded with the indicator strains *Lactobacillus helveticus* CH-1. Plates were incubated overnight at 42° C. Standards included on the assay plate are: 1,50; 2,100; 3,200; 9,300; 10,400 U/ml.

Expression of all three mutated nisA genes resulted in the production of an active molecule as determined directly by colony overlays. Plate diffusion bioassays on cell extracts demonstrated that the levels of antimicrobial activity against *Lactobacillus helveticus* were comparable to that of the parent strain FI5876 (FIG. 6). FI8070, encoding nisA/S5A, generated a zone of inhibition similar in size to that of the parent strain FI5876. This suggests that the mutation in the nisin variant (nisinA/Dha5A) does not significantly affect its antimicrobial properties against this indicator organism. A cell extract from FI8198 (producing the variant nisin A/Dha33A) was consistently found to generate a zone of inhibition larger than that of the parent strain (FIG. 6). This corresponds to an increase of approximately 50% of nisin A levels, under the conditions used here (Table 1). This higher level of production was not found in the extracts of FI8199, producing the double mutant nisin A/Dha5A,Dha33A. The inhibitory effect of this nisin variant was equivalent that of nisin A containing the single mutation and also the wild type molecule (Table 1). In all cases the yield for a particular nisin variant was higher when using this gene replacement strategy than when the equivalent plasmid-encoded gene was employed in a plasmid complementation system (Table 3, Dodd et al (1992) (1993) supra).

TABLE 3

Comparison of nisin activity from Lactococcal expression systems.

| | nisin activity[a] (% of wild type) | |
|---|---|---|
| nisin variant | complementation[b] | gene replacement[c] |
| nisin A (wild-type) | 50 | 100 |
| nisin A (Dha5A) | 25 | 100 |
| nisin A (Dha33A) | 10 | 150 |
| nisin A (Dha5A, Dha33A) | <1[d] | 100 |

[a]determined from plate diffusion bioassays
[b]antimicrobial activity achieved by plasmid-encoded nisA genes complementing nisA deficiency in host strain FI7332
[c]antimicrobial activity achieved by gene replacement. Functional nisA gene incorporated in the chromosome of FI7990 in place of nisA deletion.
[d]activity was below the level of detection of the bioassay The system developed here is producing variant nisins at yields equivalent to that of the nisin A-producing parental strain FI5876 (Table 1). In the case of the wild-type nisA gene, this is about 50% higher than nisin levels previously achieved using an analogous plasmid complementation approach (Dodd et al (1992) (1993) supra). A further comparison of these two systems reveals that the difference between the levels of production is surprisingly more pronounced for the nisin variants (Table 3). The gene replacement approach increases nisin A/Dha5A yields approximately 4 fold and for nisin A/Dha33A the yield is over ten times higher. The increased efficiency of production of the double mutant nisin A/Dha5A,Dha33A is particularly striking (Table 3). When the gene that specifies this variant nisin is plasmid encoded and used to complement the host strains nisA deficiency antimicrobial activity was only detected in the more sensitive colony overlay assay. Cell extracts from this strain did not display any activity in plate diffusion bioassays (Table 3). However, when the gene is incorporated into the chromosome using the gene replacement strategy the activity levels were equivalent to that of nisin A representing an increase in production of over 100%. This unexpected finding is of relevance to the subsequent chemical and biochemical analysis of the engineered molecules. Considerable amounts of purified peptides are required to fully characterise the novel nisins and to produce amount on a scale suitable for satisfying the market of a food preservative and the system described here appears to ensure that relatively high yields are achieved.

We have produced a variety of variant nisin-producing strains using the methodology described in this example. These are described in Table 4. Suitable oligonucleotide primers for effecting the specific mutations were designed from the sequence given in FIG. 4 and as shown in FIG. 11.

Figure 11:
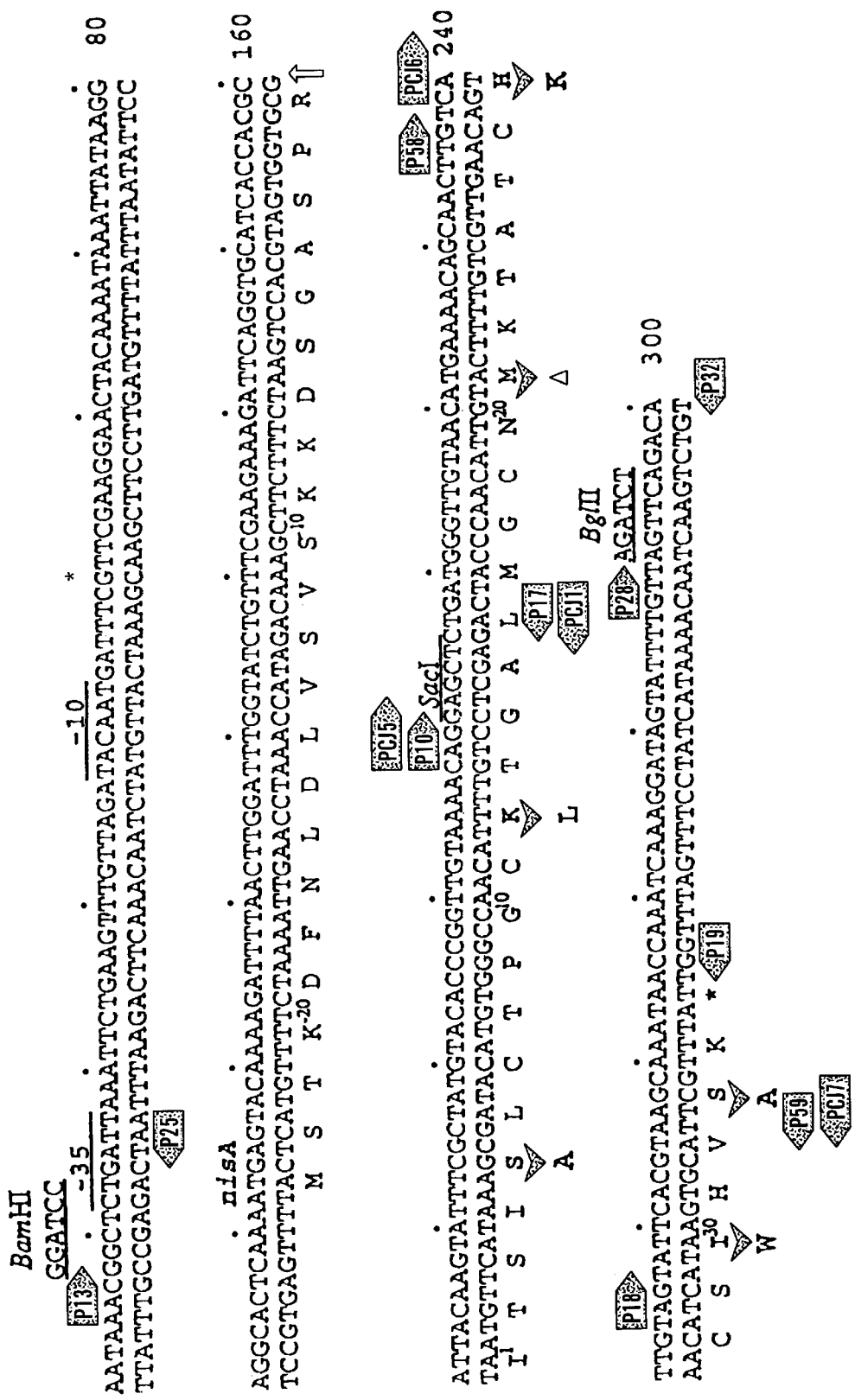
FIG. 11 shows the double-stranded nucleotide sequence of nisA gene (SEQ. ID. NO. 19) and pre-nisin amino acid sequence (SEQ. ID. NO. 20). The -35 and -10 regions and the transcription initiation site are indicated together with restriction enzyme sites used in the nisA gene cassette (see FIG. 2) above the DNA sequence. The location of primers (5'-end) employed in amplification of the cassette fragments and PCR-mediated mutagenesis are shown, above and below the sequence, as horizontal black arrows indicating the direction of DNA synthesis. Specific amino acid substitutions, as a result of the mutagenesis, are shown below the pre-nisin sequence: nisA/S5A (SEQ. ID. NO. 23); nisA/K12L (SEQ. ID. NO. 40); nisA/M21 deletion (SEQ. ID. NO. 41); nisA/H27K (SEQ. ID. NO. 42); nisA/I30W (SEQ. ID. NO. 43); nisA/S33A (SEQ. ID. NO. 26).
Figure 12:
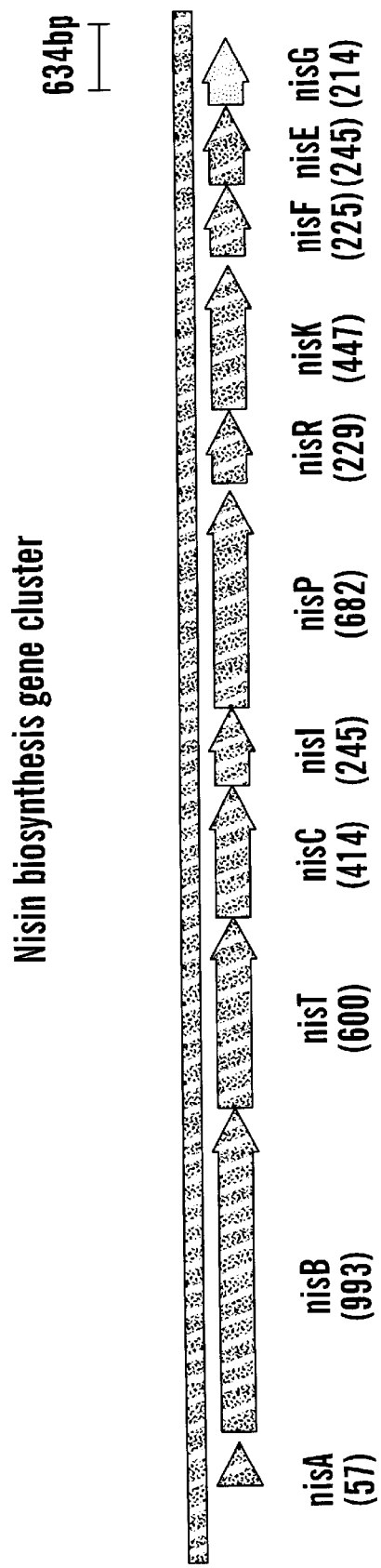
FIG. 12 is a representation of the organization of the nis genes.

Suitable oligonucleotide primers for effecting the specific mutations were designed from the sequence given in FIG. 4 and as shown in FIG. 11.

TABLE 4

Nisin producing strains generated by gene replacement.

| Strain Number | nisA mutation | | Activity[a] (% of wt) | MICH[b] ($\mu$g ml$^{-1}$) |
|---|---|---|---|---|
| MG1614 | — | | — | — |
| FI5876 | wt | | 100 | 0.13 |
| FI7990 | ΔnisA | (SEQ. ID. No. 20) | — | — |
| FI8070 | S5A | (SEQ. ID. No. 24) | 100 | 0.25 |
| FI8198 | S33A | (SEQ. ID. No. 26) | 150 | 0.25 |
| FI8199 | S5A, S33A | (SEQ. ID. No. 28) | 100 | 1.00 |
| FI8157 | H27W | (SEQ. ID. No. 44) | <1 | nd[c] |

TABLE 4-continued

Nisin producing strains generated by gene replacement.

| Strain Number | nisA mutation | | Activity[a] (% of wt) | MICH[b] ($\mu$g ml$^{-1}$) |
|---|---|---|---|---|
| FI8122 | S5A, H27W | (SEQ. ID. No. 45) | 10 | nd |
| FI8307 | H27K | (SEQ. ID. No. 42) | 100 | 0.13 |
| FI8328 | H31K | (SEQ. ID. No. 46) | 25 | nd |
| FI8330 | H27K, H31K | (SEQ. ID. No. 47) | 10 | nd |
| FI8256 | K12L | (SEQ. ID. No. 40) | 10 | 0.13 |
| FI8290 | ΔM21 | (SEQ. ID. No. 41) | <1 | nd |
| FI8289 | I30W | (SEQ. ID. No. 43) | <1 | 0.16 |

[a]Antimicrobial activity in culture supernatants determined in plate diffusion bioassays.
[b]Minimum inhibitory concentrations (MICs) were determined against the sensitive L. Lactis strain MG1614, nd, not determined.

In some circumstances it is desirable to add nisA nisin as an inducer. Table 5 shows the results of using various inducing agents.

TABLE 5

| | Inducing agent | Induction[a] | | MIC[b] |
|---|---|---|---|---|
| Strain | (nisin variant) | 100 ng ml$^{-1}$ | 1 mg ml$^{-1}$ | (mg ml$^{-1}$) |
| MG1614 | — | 2 | 4 | — |
| FI5876 | — | 94 | 100 | — |
| FI7847 | — | 3 | 3 | — |
| FI7847 | A (wild type) | 104 | 104 | 0.13 |
| FI7847 | Dha5A | 114 | 107 | 0.25 |
| FI7847 | Dha33A | 17 | 101 | 0.25 |
| FI7847 | Dha5, 33A | 34 | 106 | 1.00 |
| FI7847 | H27K | 86 | nt | 0.13 |
| FI7847 | K12L | 81 | nt | 0.13 |
| FI7847 | I30W | 41 | nt | 0.16 |

Example 2

Purification of a Variant Nisin

Strains FI8070 (nisA/S5A) is cultured and the variant nisin (in which Dha5 is replaced with alanine) is secreted into the culture medium.

The variant nisin is purified using a method based on that described by Mulders et al (1991) *Eur. J. Biochem.* 201, 581–584. 1 liter cultures were incubated at 30° C. for 16 hours. The pH of cultures was reduced to 2–3 with HCl before centrifugation at 10,000 rpm for 10 minutes. The cell-free supernatants were retained and the pH increased to 5–6 with 10 mM NaOH. To each 10 ml of supernatant 0.99 g of $(NH_4)_2SO_4$ was added. This solution was then filtered (Millipore, 0.45 $\mu$m) prior to running on a Fractogel TSK Butyl 650S (Merk) column, bed volume 5×20 cm, previously equilibrated with 0.8 M $(NH_4)_2SO_4$. The column was washed with ~1 litre of 0.8 M $(NH_4)_2SO_4$ until the absorbance at 220 dropped to below 0.5. The bound nisin was eluted with 5 mM HCl and 10 ml fractions were assayed for nisin activity. Active fractions were pooled and freeze dried. Reverse phase HPLC was carried out on the resuspended samples using $\mu$Bondapak $C_{18}$ column 3.9×300 mm run at room temperature. Solvents used were 0.06% (v/v) trifluoroacetic acid and 0.06% (v/v) trifluoroacetic acid in 90% (v/v) aqueous acetonitrile. Absorbance was measured at 220 nm.

Example 3

Addition of Variant Nisin to Cheese

The variant nisin produced by strain FI8070 (in which Dha5 is replaced with alanine) is added at a concentration of 12.5 mg per kg to soft cheese spread in order to prevent the growth of food-spoilage or pathogenic bacteria.

What is claimed is:

1. A method for making a cell which does not contain a natural nisA gene but expresses a variant nisA gene comprising the steps of
   providing a cell that contains a natural, chromosomal nisA gene and
   substituting the natural nisA gene or part thereof with a non-naturally occurring variant nisA gene at the chromosomal location of the natural nisA gene or part thereof, wherein the variant nisA gene encodes a variant nisin.

2. A method according to claim 1 wherein the variant nisA gene comprises a regulatory region other than the natural nisA gene regulatory region and a variant nisin coding region.

3. A method according to claim 1 wherein the cell is a Lactococcus.

4. A method according to claim 1 comprising the steps of (1) substituting a natural, chromosomal nisA gene with a counter-selectable nisA gene at the chromosomal location of the said natural nisA gene and (2) substituting a counter-selectable nisA gene with a variant nisA gene at the chromosomal location of the said natural nisA gene.

5. A method according to claim 1 comprising a subsequent step of selecting a cell that is immune to nisin.

6. A method according to claim 4 wherein the counter-selectable nisA gene comprises an antibiotic resistance gene.

7. A method according to claim 6 further comprising the step of selecting a cell that is sensitive to the said antibiotic.

8. A method according to claim 1 wherein the variant nisA gene contains a modification to the transcriptional or translational control sequences of the natural nisA gene and, as a consequence, the cell expresses an elevated level of the variant nisin compared to the expression level by the natural nisA gene.

9. A recombinant cell derived from a cell which contains and expresses a natural, chromosomal nisA gene, said recombinant cell no longer containing the natural nisA gene but expressing a variant nisA gene, wherein the natural nisA gene or part thereof is substituted with the variant nisA gene at the chromosomal location of the natural nisA gene or part thereof, and wherein the variant nisA gene encodes a variant nisin.

10. A cell according to claim 9 wherein the variant nisA gene comprises a regulatory region other than the natural nisA gene regulatory region and a variant nisin coding region.

11. A cell according claim 9 wherein the cell is a Lactococcus.

12. A cell according to claim 9 that is immune to nisin.

13. A cell according to claim 9 wherein the variant nisA gene contains a modification to the transcriptional or translational control sequences of the natural nisA gene and, as a consequence, the cell expresses an elevated level of the variant nisin compared to the expression level by the natural nisA gene.

14. A process for producing a variant nisin comprising culturing a cell according to claim 9 and obtaining the variant nisin produced thereby.

15. A process according to claim 14 wherein the cell is cultured in the presence of nisA nisin or a variant nisin which can induce nisin expression.

16. A process according to claim 15 wherein the amount of nisA nisin is a minimum amount that provides maximal induction of nisin production.

* * * * *

SEQUENCE LISTING

<160> NUMBER OF SEQ ID NOS: 51

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 1
aacggatccg attaaattct gaagtttg                                           28

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 2
tcagagctcc tgttttacaa ccgggtgtac atagtgcaat                              40

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 3
tagtattcac gtagctaaat aacc                                               24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 4
ttggttattt agctacgtga atac                                               24

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 5
aatcggatcc gtttattatg ctcgc                                              25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 6
atagttgacg aatatttaat aatttt                                             26

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence:  PCR primer

<400> SEQUENCE: 7
cttggtcgac accatatttt                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  PCR primer

<400> SEQUENCE: 8
gttagatctg acatggatac                                             20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:  PCR primer

<400> SEQUENCE: 9
ccatgtcaga tctaacaaaa tac                                         23

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:  PCR primer

<400> SEQUENCE: 10
gactttccat tatgcttgga ttttt                                       25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:  PCR primer

<400> SEQUENCE: 11
gctcctatgc caaatgtaga atc                                         23

<210> SEQ ID NO 12
<211> LENGTH: 16
<212> TYPE: DNA
<213> ORGANISM: Lactococcus sp.

<400> SEQUENCE: 12
gagctcggta cccggg                                                 16

<210> SEQ ID NO 13
<211> LENGTH: 16
<212> TYPE: DNA
<213> ORGANISM: Lactococcus sp.

<400> SEQUENCE: 13
cccgggtacc gagctc                                                 16

<210> SEQ ID NO 14
```

```
<211> LENGTH: 24
<212> TYPE: DNA
<213> ORGANISM: Lactococcus sp.

<400> SEQUENCE: 14
aaaacaggag ctctgatggg ttgt                                              24

<210> SEQ ID NO 15
<211> LENGTH: 8
<212> TYPE: PRT
<213> ORGANISM: Lactococcus sp.

<400> SEQUENCE: 15

Lys Thr Gly Ala Leu Met Gly Cys
        1               5

<210> SEQ ID NO 16
<211> LENGTH: 45
<212> TYPE: DNA
<213> ORGANISM: Lactococcus sp.

<400> SEQUENCE: 16
aaaacaggag ctcggtaccc gggtaccgag ctctgatggg tttgt                 45

<210> SEQ ID NO 17
<211> LENGTH: 11
<212> TYPE: PRT
<213> ORGANISM: Lactococcus sp.

<400> SEQUENCE: 17

Lys Thr Gly Ala Arg Tyr Pro Gly Thr Glu Leu
  1               5                  10

<210> SEQ ID NO 18
<211> LENGTH: 7
<212> TYPE: PRT
<213> ORGANISM: Lactococcus sp.

<400> SEQUENCE: 18

Arg Tyr Pro Gly Thr Glu Leu
  1               5

<210> SEQ ID NO 19
<211> LENGTH: 300
<212> TYPE: DNA
<213> ORGANISM: Lactococcus sp.

<400> SEQUENCE: 19
aataaacggc tctgattaaa ttctgaagtt tgttagatac aatgatttcg ttcgaaggaa       60
ctacaaaata aattataagg aggcactcaa aatgagtaca aaagatttta acttggattt      120
ggtatctgtt tcgaagaaag attcaggtgc atcaccacgc attacaagta tttcgctatg      180
tacacccggt tgtaaaacag gagctctgat gggttgtaac atgaaaacag caacttgtca      240
ttgtagtatt cacgtaagca aataaccaaa tcaaaggata gtattttgtt agttcagaca      300

<210> SEQ ID NO 20
<211> LENGTH: 57
<212> TYPE: PRT
<213> ORGANISM: Lactococcus sp.

<400> SEQUENCE: 20

Met Ser Thr Lys Asp Phe Asn Leu Asp Leu Val Ser Val Ser Lys Lys
  1               5                  10                  15
```

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 21
<211> LENGTH: 300
<212> TYPE: DNA
<213> ORGANISM: Lactococcus sp.

<400> SEQUENCE: 21
aataaacgga tccgattaaa ttctgaagtt tgttagatac aatgatttcg ttcgaaggaa    60
ctacaaaata aattataagg aggcactcaa aatgagtaca aaagatttta acttggattt   120
ggtatctgtt tcgaagaaag attcaggtgc atcaccacgc attacaagta tttcgctatg   180 tacaccggt tgtaaaacag gagctctgat gggttgtaac atgaaaacag caacttgtca   240
ttgtagtatt cacgtaagca ataaccaaa tcaaggata gtattttgtt agatctgaca    300

<210> SEQ ID NO 22
<211> LENGTH: 300
<212> TYPE: DNA
<213> ORGANISM: Lactococcus sp.

<400> SEQUENCE: 22
aataaacggc tctgattaaa ttctgaagtt tgttagatac aatgatttcg ttcgaaggaa    60
ctacaaaata aattataagg aggcactcaa aatgagtaca aaagatttta acttggattt   120
ggtatctgtt tcgaagaaag attcaggtgc atcaccacgc attacaagta tttcgctatg   180 tacaccggt tgtaaaacag gagctctgat gggttgtaac atgaaaacag caacttgtca   240
ttgtagtatt cacgtaagca ataaccaaa tcaaggata gtattttgtt agatctgaca    300

<210> SEQ ID NO 23
<211> LENGTH: 300
<212> TYPE: DNA
<213> ORGANISM: Lactococcus sp.

<400> SEQUENCE: 23
aataaacgga tccgattaaa ttctgaagtt tgttagatac aatgatttcg ttcgaaggaa    60
ctacaaaata aattataagg aggcactcaa aatgagtaca aaagatttta acttggattt   120
ggtatctgtt tcgaagaaag attcaggtgc atcaccacgc attacaagta tctggctatg   180 tacaccggt tgtaaaacag gagctctgat gggttgtaac atgaaaacag caacttgtca   240
ttgtagtatt cacgtaagca ataaccaaa tcaaggata gtattttgtt agttcagaca    300

<210> SEQ ID NO 24
<211> LENGTH: 57
<212> TYPE: PRT
<213> ORGANISM: Lactococcus sp.

<400> SEQUENCE: 24

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ala Leu Cys Thr Pro
            20                  25                  30

Gly Cys Lys Thr Gly Ala Leu Met Gly Cys Asn Met Lys Thr Ala Thr

```
                    35                 40                 45

Cys His Cys Ser Ile His Val Ser Lys
         50                 55

<210> SEQ ID NO 25
<211> LENGTH: 300
<212> TYPE: DNA
<213> ORGANISM: Lactococcus sp.

<400> SEQUENCE: 25
aataaacgga tccgattaaa ttctgaagtt tgttagatac aatgatttcg ttcgaaggaa      60
ctacaaaata aattataagg aggcactcaa aatgagtaca aaagatttta acttggattt    120
ggtatctgtt tcgaagaaag attcaggtgc atcaccacgc attacaagta tttcgctatg    180
tacacccggt tgtaaaacag gagctctgat gggttgtaac atgaaaacag caacttgtca    240
ttgtagtatt cacgtctgca aataaccaaa tcaaaggata gtattttgtt agttcagaca    300

<210> SEQ ID NO 26
<211> LENGTH: 57
<212> TYPE: PRT
<213> ORGANISM: Lactococcus sp.

<400> SEQUENCE: 26

Met Ser Thr Lys Asp Phe Asn Leu Asp Leu Val Ser Val Ser Lys Lys
  1               5                  10                  15

Asp Ser Gly Ala Ser Pro Arg Ile Thr Ser Ile Ser Leu Cys Thr Pro
             20                  25                  30

Gly Cys Lys Thr Gly Ala Leu Met Gly Cys Asn Met Lys Thr Ala Thr
         35                  40                  45

Cys His Cys Ser Ile His Val Ala Lys
         50                  55

<210> SEQ ID NO 27
<211> LENGTH: 300
<212> TYPE: DNA
<213> ORGANISM: Lactococcus sp.

<400> SEQUENCE: 27
aataaacgga tccgattaaa ttctgaagtt tgttagatac aatgatttcg ttcgaaggaa      60
ctacaaaata aattataagg aggcactcaa aatgagtaca aaagatttta acttggattt    120
ggtatctgtt tcgaagaaag attcaggtgc atcaccacgc attacaagta tctggctatg    180
tacacccggt tgtaaaacag gagctctgat gggttgtaac atgaaaacag caacttgtca    240
ttgtagtatt cacgtctgca aataaccaaa tcaaaggata gtattttgtt agttcagaca    300

<210> SEQ ID NO 28
<211> LENGTH: 57
<212> TYPE: PRT
<213> ORGANISM: Lactococcus sp.

<400> SEQUENCE: 28

Met Ser Thr Lys Asp Phe Asn Leu Asp Leu Val Ser Val Ser Lys Lys
  1               5                  10                  15

Asp Ser Gly Ala Ser Pro Arg Ile Thr Ser Ile Ala Leu Cys Thr Pro
             20                  25                  30

Gly Cys Lys Thr Gly Ala Leu Met Gly Cys Asn Met Lys Thr Ala Thr
         35                  40                  45

Cys His Cys Ser Ile His Val Ala Lys
```

<210> SEQ ID NO 29
<211> LENGTH: 7454
<212> TYPE: DNA
<213> ORGANISM: Lactococcus sp.

<400> SEQUENCE: 29

```
aatgacctag tcttataact atactgacaa tagaaacatt aacaaatcta aaacagtctt      60
aattctatct tgagaaagta ttggtaataa tattattgtc gataacgcga gcataataaa     120
cggctctgat taaattctga gtttgttag atacaatgat ttcgttcgaa ggaactacaa      180
aataaattat aaggaggcac tcaaaatgag tacaaaagat tttaacttgg atttggtatc     240
tgtttcgaag aaagattcag gtgcatcacc acgcattaca agtatttcgc tatgtacacc     300
cggttgtaaa acaggagctc tgatgggttg taacatgaaa acagcaactt gtcattgtag     360
tattcacgta agcaaataac caaatcaaag gatagtattt tgttagttca gacatggata     420
ctatcctatt tttataagtt atttaggggt gctaaatagc ttataaaaat aaagagagga     480
aaaaacatga taaaaagttc atttaaagct caaccgtttt tagtaagaaa tacaatttta     540
tctccaaacg ataaacggag ttttactgaa tatactcaag tcattgagac tgtaagtaaa     600
aataaagttt ttttggaaca gttactacta gctaatccta aactctatga tgttatgcag     660
aaatataatg ctggtctgtt aaagaagaaa agggttaaaa aattatttga atctatttac     720
aagtattata agagaagtta tttacgatca actccatttg gattatttag tgaaacttca     780
attggtgttt tttcgaaaag ttcacagtac aagttaatgg aaagactac aaagggtata      840
agattggata ctcagtggtt gattcgccta gttcataaaa tggaagtaga tttctcaaaa     900
aagttatcat ttactagaaa taatgcaaat tataagtttg gagatcgagt ttttcaagtt     960
tataccataa atagtagtga gcttgaagaa gtaaatatta aatatacgaa tgtttatcaa    1020
attatttctg aattttgtga gaatgactat caaaaatatg aagatatttg tgaaactgta    1080
acgctttgct atggagacga atatagagaa ctatcggaac aatatcttgg cagtctgata    1140
gttaatcatt atttgatctc taatttacaa aaagatttgt tgtcagattt ttcttggaac    1200
acttttttga ctaaagttga agcaatagat gaagataaaa aatatataat tcctctgaaa    1260
aaagttcaaa agtttattca agaatactca gaaatagaaa ttggtgaagg tattgagaaa    1320
ctgaaagaaa tatatcagga aatgtcacaa attcttgaga atgataatta tattcaaatt    1380
gatttaatta gtgatagtga aataaatttt gatgttaaac aaaagcaaca attagaacat    1440
ttagctgagt ttttaggaaa tacgacaaaa tctgtaagaa gaacatattt ggatgactat    1500
aaggataaat ttatcgaaaa atatggtgta gatcaagaag tacaaataac agaattattt    1560
gattctacat ttggcatagg agctccatat aattataatc atcctcgaaa tgactttttat   1620
gagtccgaac cgagtactct atactattca gaagaggaga gagaaaagta cctcagcatg    1680
tatgtagaag ccgttaaaaa tcataatgta attaatcttg acgacttaga gtctcattat    1740
caaaaaatgg acttagaaaa gaaaagtgaa cttcaagggt tagaattatt tttgaatttg    1800
gcaaaggagt atgaaaaaga tatttttatt ttaggggata tcgttggaaa taataatttg    1860
ggagggcat caggtagatt ttctgcactc tctccggagt taacaagtta tcatagaacg     1920
atagtagatt ctgtcgaaag agaaaatgag aataaagaaa ttcatcgtg tgaaatagta     1980
tttcttccag aaaatatcag acatgctaac gttatgcata catcaattat gaggaggaaa    2040
gtacttccat tttttacaag tacaagtcac aatgaagttc tgttaactaa tatctatatt    2100
```

```
ggaatagacg aaaaagaaaa attttatgca cgagacattt caactcaaga ggtattgaaa   2160
ttctacatta caagcatgta caataaaacg ttattcagta atgagctaag atttctttac   2220
gaaatttcat tagatgacaa gtttggtaat ttaccttggg aacttattta cagagacttt   2280
gattatattc cacgtttagt atttgacgaa atagtaatat ctcctgctaa atggaaaatt   2340
tggggaaggg atgtaaatag taagatgaca ataagagaac ttattcaaag caagaaatt    2400 cccaaagagt tttatattgt caatggagat aataaagttt atttatcaca ggaaaaccca   2460
ttggatatgg aaattttaga gtcggcgata agaagagct caaaaagaaa agattttata    2520
gagctacaag aatattttga agatgaaaat atcataaata aggagaaaa ggggagagtt    2580 gccgatgttg tagtgccttt tattagaacg agagcattag gtaatgaagg gagagcattt   2640
ataagagaga aaagagtttc ggttgaacgg cgtgaaaaat tgccctttaa cgagtggctt   2700
tatctaaagt tgtacatttc tataaatcgt caaaatgaat ttttactgtc gtatcttcca   2760
gatattcaga aatagtagc aaacctgggt ggaaatctat tcttcctaag atatactgat    2820
cctaaaccac atattagatt gcgtataaaa tgttcagatt tattttagc ttacggatct    2880 attcttgaaa tcttaaaaag gagtcggaaa ataggataa tgtcaacttt tgatatttct    2940
atttatgatc aagaagtaga aagatatggt ggatttgata ctttagagtt atccgaagca   3000
atattttgtg ccgattctaa aattattcca aatttgctta cattgataaa agatactaat   3060
aatgattgga aagtcgatga tgtatcaatc ttggtgaatt atttatatct gaaatgcttc   3120
tttcagaatg ataacaaaaa gattcttaat tttttgaatt tagttagtcc taaaaaggtt   3180
aaagaaaatg tcaatgaaaa gattgaacat tatcttaagc ttctgaaagt taataatcta   3240
ggtgaccaaa tttttatga caagaatttt aaagaattaa agcatgccat aaaaaattta    3300
tttttaaaaa tgatagctca agattttgaa cttcagaaag tttattcaat tattgacagt   3360
atcattcatg tccataataa ccgactaatt ggtattgaac gagataaaga gaaattaatt   3420
tattacacac ttcaaaggtt gtttgtttcg gaagaataca tgaaatgagg actaatagat   3480
ggatgaagtg aaagaattca catcaaaaca attttttaat actttactta ctcttccaag   3540
caccttgaag ttaattttc agttggaaaa acgttatgca atttatttaa ttgtgctaaa    3600
tgctatcaca gcttttgttc cgttggctag tctttttatt tatcaagatt taataaactc   3660
tgtgctaggt tcagggagac atcttatcaa tattattatc atctatttta ttgttcaagt   3720
gataacaaca gttctgggac agctggaaag ttatgttagt ggaaaatttg atatgcgact   3780
ttcttacagt atcaatatgc gcctcatgag gactacctca tctcttgaat taagtgatta   3840
tgagcaggct gatatgtata atatcataga aaaagttact caagacagca cttacaagcc   3900
ttttcagcta tttaatgcta tcattgttgt gctttcatcg tttatctcat tgttatctag   3960 tctattttt attggaacat ggaacattgg ggtagcaatt ttactcctta ttgttccagt    4020
attatctttg gtacttttc tcagagtggg acaattagag tttttaatcc agtggcagag    4080
agcaagttct gaaagagaaa catggtatat tgtatattta ttgactcatg atttttcatt   4140
taaagaaatc aagttaaata atattagcaa ttacttcatt cataaatttg gaaaattaaa   4200 gaaggattt atcaaccaag atttagctat tgctcgtaag aagacatatt tcaatatttt    4260
tcttgatttc attttgaatt tgataaatat tcttacgata tttgctatga tcctttcggt   4320
aagagcagga aaacttctta taggtaattt ggtaagtctc atacaagcta tttctaaaat   4380
caatacttat tctcaaacaa tgattcaaaa tatttacatc atttataata ctagtttgtt   4440
```

```
tatggaacaa cttttttgagt ttttaaagag agaaagtgta gttcacaaaa aaatagaaga  4500
tactgaaata tgcaatcaac ataiaggaac tgttaaagta attaatttat catatgttta  4560
ccctaattcg aatgcctttg cactaaagaa tatcaattta tcctttgaaa aaggagaatt  4620
aactgctatt gtaggaaaaa atggttcagg gaaaagtaca ctagtaaaga taatttcagg  4680
attatatcaa ccaactatgg gaataatcca atacgacaaa atgagaagta gtttgatgcc  4740
tgaggagttt tatcagaaaa acatatcggt gctgttccaa gattttgtga agtatgagtt  4800
aacgataaga gagaatatag gattgagtga tttgtcttct caatgggaag atgagaaaat  4860
tattaaagta ctagataatt taggactcga ttttttgaaa actaataatc aatatgtact  4920
tgatacgcag ttaggaaatt ggtttcaaga agggcatcaa ctttcaggag gtcagtggca  4980
aaaaattgca ttagcaagga cattctttaa gaaagcttca atttatattt tagatgaacc  5040
aagtgctgca ctcgatcctg tagctgaaaa agaaatattt gattattttg ttgctctttc  5100
ggaaaataat atttcaattt tcatttctca tagtttgaat gctgccagaa aagcaaataa  5160
aatcgtggtt atgaaagatg gacaggtcga agatgttgga agtcatgatg tccttctgag  5220
aagatgtcaa tactatcaag aactttatta ttcagagcaa tatgaggata atgatgaata  5280
aaaaaaatat aaaagaaat gttgaaaaaa ttattgctca atgggatgag agaactagaa  5340
aaaataaaga aaacttcgat ttcggagagt tgactctctc tacaggattg cctggtataa  5400
ttttaatgtt agcggagtta aaaaataaag ataactcaaa gatatatcag aaaaagatag  5460
acaattatat tgaatatatt gttagcaaac tttcaacata tgggctttta acaggatcac  5520
tttattcggg agcagctggc attgcattaa gtatcctaca tttacagaaa gatgacgaaa  5580
aatataagaa tcttcttgat agcctaaata gatatatcga atatttcgtc agagaaaaaa  5640
ttgaaggatt taatttggaa acattactc ctcctgatta tgacgtgatt gaaggtttat  5700
ctgggatact ttcctatcta ttattaatca acgacgagca atatgatgat ttgaaaatac  5760
tcattatcaa ttttttatca aatctgacta agaaaacaa tggactaata tcgctttaca  5820
tcaaatcgga gaatcagatg tctcaatcag aaagtgagat gtatccacta ggctgtttga  5880
atatgggatt agcacatgga cttgctggag tgggctgtat cttagcttat gcccacataa  5940
aaggatatag taatgaagcc tcgttgtcag ctttgcaaaa aattatttt atttatgaaa  6000
agtttgaact tgaaaggaaa aaacagtttc tatggaaaga tggacttgta gcagatgaat  6060
taaaaaaaga gaaagtaatt agggaagcaa gtttcattag agatgcatgg tgctatggag  6120
gtccaggtat tagtctgcta tacttatacg gaggattagc actggataat gactattttg  6180
tagataaagc agaaaaaata ttagagtcag ctatgcaaag gaaacttggt attgattcat  6240
atatgatttg ccatggctat tctggtttaa tagaaatttg ttctttattt aagcggctat  6300
taaatacaaa aaagtttgat tcatacatgg aagaatttaa tgttaatagt gagcaaattc  6360
ttgaagaata cggagatgaa agtggcacgg gtttttcttga aggaataagt ggctgtatac  6420
tggtattatc gaaatttgaa tattcaatca attttactta ttggagacaa gcactgttac  6480
tttttgacga ttttttgaaa ggagggaaga ggaaatgaga agatattaa tacttattgt  6540
ggccttaata gggataacag gtttatcagg gtgttatcaa acaagtcata aaaaggtgag  6600
gtttgacgaa ggaagttata ctaattttat ttatgataat aaatcgtatt tcgtaactga  6660
taaggagatt cctcaggaga acgttaacaa ttccaaagta aatttttata agctgttgat  6720
tgttgacatg aaaagtgaga aacttttatc aagtagcaac aaaaatagtg tgactttggt  6780
cttaaataat atttatgagg cttctgacaa gtcgctatgt atgggtatta acgacagata  6840
```

```
ctataagata cttccagaaa gtgataaggg ggcggtcaaa gctttgagat tacaaaactt    6900
tgatgtgaca agcgatattt ctgatgataa ttttgttatt gataaaaatg attcacgaaa    6960
aattgactat atgggaaata tttacagtat atcggacacc accgtatctg atgaagaatt    7020
gggagaatat caggatgttt tagctgaagt acgtgtgttt gattcagtta gtggcaaaag    7080
tatcccgagg tctgaatggg ggagaattga taaggatggt tcaaattcca aacagagtag    7140
gacggaatgg gattatggcg aaatccattc tattagagga aaatctctta ctgaagcatt    7200
tgccgttgag ataaatgatg attttaagct tgcaacgaag gtaggaaact agagtgaaaa    7260
aaatactagg tttcctttt atcgtttgtt cgttgggttt atcagcaact gtgcatgggg     7320
agacaacaaa ttcacaacag ttactctcaa ataatattaa tacggaatta attaatcata    7380
attctaatgc aattttatct tcaacagagg gatcaacgac tgattcgatt aatctagggg    7440
cgcagtcacc tgca                                                      7454
```

<210> SEQ ID NO 30
<211> LENGTH: 993
<212> TYPE: PRT
<213> ORGANISM: Lactococcus sp.

<400> SEQUENCE: 30

```
Met Ile Lys Ser Ser Phe Lys Ala Gln Pro Phe Leu Val Arg Asn Thr
  1               5                  10                  15

Ile Leu Ser Pro Asn Asp Lys Arg Ser Phe Thr Glu Tyr Thr Gln Val
             20                  25                  30

Ile Glu Thr Val Ser Lys Asn Lys Val Phe Leu Glu Gln Leu Leu Leu
         35                  40                  45

Ala Asn Pro Lys Leu Tyr Asp Val Met Gln Lys Tyr Asn Ala Gly Leu
     50                  55                  60

Leu Lys Lys Lys Arg Val Lys Lys Leu Phe Glu Ser Ile Tyr Lys Tyr
 65                  70                  75                  80

Tyr Lys Arg Ser Tyr Leu Arg Ser Thr Pro Phe Gly Leu Phe Ser Glu
                 85                  90                  95

Thr Ser Ile Gly Val Phe Ser Lys Ser Ser Gln Tyr Lys Leu Met Gly
            100                 105                 110

Lys Thr Thr Lys Gly Ile Arg Leu Asp Thr Gln Trp Leu Ile Arg Leu
        115                 120                 125

Val His Lys Met Glu Val Asp Phe Ser Lys Leu Ser Phe Thr Arg
    130                 135                 140

Asn Asn Ala Asn Tyr Lys Phe Gly Asp Arg Val Phe Gln Val Tyr Thr
145                 150                 155                 160

Ile Asn Ser Ser Glu Leu Glu Glu Val Asn Ile Lys Tyr Thr Asn Val
                165                 170                 175

Tyr Gln Ile Ile Ser Glu Phe Cys Glu Asn Asp Tyr Gln Lys Tyr Glu
            180                 185                 190

Asp Ile Cys Glu Thr Val Thr Leu Cys Tyr Gly Asp Tyr Arg Glu
        195                 200                 205

Leu Ser Glu Gln Tyr Leu Gly Ser Leu Ile Val Asn His Tyr Leu Ile
    210                 215                 220

Ser Asn Leu Gln Lys Asp Leu Leu Ser Asp Phe Ser Trp Asn Thr Phe
225                 230                 235                 240

Leu Thr Lys Val Glu Ala Ile Asp Glu Asp Lys Lys Tyr Ile Ile Pro
                245                 250                 255
```

-continued

```
Leu Lys Lys Val Gln Lys Phe Ile Gln Glu Tyr Ser Glu Ile Glu Ile
            260                 265                 270
Gly Glu Gly Ile Glu Lys Leu Lys Glu Ile Tyr Gln Glu Met Ser Gln
            275                 280                 285
Ile Leu Glu Asn Asp Asn Tyr Ile Gln Ile Asp Leu Ile Ser Asp Ser
            290                 295                 300
Glu Ile Asn Phe Asp Val Lys Gln Lys Gln Leu Glu His Leu Ala
305                 310                 315                 320
Glu Phe Leu Gly Asn Thr Thr Lys Ser Val Arg Arg Thr Tyr Leu Asp
                    325                 330                 335
Asp Tyr Lys Asp Lys Phe Ile Glu Lys Tyr Gly Val Asp Gln Glu Val
            340                 345                 350
Gln Ile Thr Glu Leu Phe Asp Ser Thr Phe Gly Ile Gly Ala Pro Tyr
            355                 360                 365
Asn Tyr Asn His Pro Arg Asn Asp Phe Tyr Glu Ser Glu Pro Ser Thr
            370                 375                 380
Leu Tyr Tyr Ser Glu Glu Arg Glu Lys Tyr Leu Ser Met Tyr Val
385                 390                 395                 400
Glu Ala Val Lys Asn His Asn Val Ile Asn Leu Asp Asp Leu Glu Ser
                    405                 410                 415
His Tyr Gln Lys Met Asp Leu Glu Lys Lys Ser Glu Leu Gln Gly Leu
            420                 425                 430
Glu Leu Phe Leu Asn Leu Ala Lys Glu Tyr Glu Lys Asp Ile Phe Ile
            435                 440                 445
Leu Gly Asp Ile Val Gly Asn Asn Leu Gly Gly Ala Ser Gly Arg
450                 455                 460
Phe Ser Ala Leu Ser Pro Glu Leu Thr Ser Tyr His Arg Thr Ile Val
465                 470                 475                 480
Asp Ser Val Glu Arg Glu Asn Glu Asn Lys Glu Ile Thr Ser Cys Glu
                    485                 490                 495
Ile Val Phe Leu Pro Glu Asn Ile Arg His Ala Asn Val Met His Thr
            500                 505                 510
Ser Ile Met Arg Arg Lys Val Leu Pro Phe Phe Thr Ser Thr Ser His
            515                 520                 525
Asn Glu Val Leu Leu Thr Asn Ile Tyr Ile Gly Ile Asp Glu Lys Glu
            530                 535                 540
Lys Phe Tyr Ala Arg Asp Ile Ser Thr Gln Glu Val Leu Lys Phe Tyr
545                 550                 555                 560
Ile Thr Ser Met Tyr Asn Lys Thr Leu Phe Ser Asn Glu Leu Arg Phe
                    565                 570                 575
Leu Tyr Glu Ile Ser Leu Asp Asp Lys Phe Gly Asn Leu Pro Trp Glu
            580                 585                 590
Leu Ile Tyr Arg Asp Phe Asp Tyr Ile Pro Arg Leu Val Phe Asp Glu
            595                 600                 605
Ile Val Ile Ser Pro Ala Lys Trp Lys Ile Trp Gly Arg Asp Val Asn
            610                 615                 620
Ser Lys Met Thr Ile Arg Glu Leu Ile Gln Ser Lys Glu Ile Pro Lys
625                 630                 635                 640
Glu Phe Tyr Ile Val Asn Gly Asp Asn Lys Val Tyr Leu Ser Gln Glu
                    645                 650                 655
Asn Pro Leu Asp Met Glu Ile Leu Glu Ser Ala Ile Lys Lys Ser Ser
            660                 665                 670
Lys Arg Lys Asp Phe Ile Glu Leu Gln Glu Tyr Phe Glu Asp Glu Asn
```

-continued

```
            675                 680                 685
Ile Ile Asn Lys Gly Glu Lys Gly Arg Val Ala Asp Val Val Pro
690                 695                 700

Phe Ile Arg Thr Arg Ala Leu Gly Asn Glu Gly Arg Ala Phe Ile Arg
705                 710                 715                 720

Glu Lys Arg Val Ser Val Glu Arg Arg Glu Lys Leu Pro Phe Asn Glu
                725                 730                 735

Trp Leu Tyr Leu Lys Leu Tyr Ile Ser Ile Asn Arg Gln Asn Glu Phe
                740                 745                 750

Leu Leu Ser Tyr Leu Pro Asp Ile Gln Lys Ile Val Ala Asn Leu Gly
                755                 760                 765

Gly Asn Leu Phe Phe Leu Arg Tyr Thr Asp Pro Lys Pro His Ile Arg
770                 775                 780

Leu Arg Ile Lys Cys Ser Asp Leu Phe Leu Ala Tyr Gly Ser Ile Leu
785                 790                 795                 800

Glu Ile Leu Lys Arg Ser Arg Lys Asn Arg Ile Met Ser Thr Phe Asp
                805                 810                 815

Ile Ser Ile Tyr Asp Gln Glu Val Glu Arg Tyr Gly Gly Phe Asp Thr
                820                 825                 830

Leu Glu Leu Ser Glu Ala Ile Phe Cys Ala Asp Ser Lys Ile Ile Pro
835                 840                 845

Asn Leu Leu Thr Leu Ile Lys Asp Thr Asn Asn Asp Trp Lys Val Asp
850                 855                 860

Asp Val Ser Ile Leu Val Asn Tyr Leu Tyr Leu Lys Cys Phe Phe Gln
865                 870                 875                 880

Asn Asp Asn Lys Lys Ile Leu Asn Phe Leu Asn Leu Val Ser Pro Lys
                885                 890                 895

Lys Val Lys Glu Asn Val Asn Glu Lys Ile Glu His Tyr Leu Lys Leu
                900                 905                 910

Leu Lys Val Asn Asn Leu Gly Asp Gln Ile Phe Tyr Asp Lys Asn Phe
                915                 920                 925

Lys Glu Leu Lys His Ala Ile Lys Asn Leu Phe Leu Lys Met Ile Ala
930                 935                 940

Gln Asp Phe Glu Leu Gln Lys Val Tyr Ser Ile Ile Asp Ser Ile Ile
945                 950                 955                 960

His Val His Asn Asn Arg Leu Ile Gly Ile Glu Arg Asp Lys Glu Lys
                965                 970                 975

Leu Ile Tyr Tyr Thr Leu Gln Arg Leu Phe Val Ser Glu Glu Tyr Met
                980                 985                 990
Lys

<210> SEQ ID NO 31
<211> LENGTH: 600
<212> TYPE: PRT
<213> ORGANISM: Lactococcus sp.

<400> SEQUENCE: 31

Met Asp Glu Val Lys Glu Phe Thr Ser Lys Gln Phe Phe Asn Thr Leu
1               5                   10                  15

Leu Thr Leu Pro Ser Thr Leu Lys Leu Ile Phe Gln Leu Glu Lys Arg
                20                  25                  30

Tyr Ala Ile Tyr Leu Ile Val Leu Asn Ala Ile Thr Ala Phe Val Pro
                35                  40                  45

Leu Ala Ser Leu Phe Ile Tyr Gln Asp Leu Ile Asn Ser Val Leu Gly
            50                  55                  60
```

-continued

```
Ser Gly Arg His Leu Ile Asn Ile Ile Ile Tyr Phe Ile Val Gln
 65                  70                  75                  80

Val Ile Thr Thr Val Leu Gly Gln Leu Glu Ser Tyr Val Ser Gly Lys
             85                  90                  95

Phe Asp Met Arg Leu Ser Tyr Ser Ile Asn Met Arg Leu Met Arg Thr
            100                 105                 110

Thr Ser Ser Leu Glu Leu Ser Asp Tyr Glu Gln Ala Asp Met Tyr Asn
            115                 120                 125

Ile Ile Glu Lys Val Thr Gln Asp Ser Thr Tyr Lys Pro Phe Gln Leu
            130                 135                 140

Phe Asn Ala Ile Ile Val Val Leu Ser Ser Phe Ile Ser Leu Leu Ser
145                 150                 155                 160

Ser Leu Phe Phe Ile Gly Thr Trp Asn Ile Gly Val Ala Ile Leu Leu
                165                 170                 175

Leu Ile Val Pro Val Leu Ser Leu Val Leu Phe Leu Arg Val Gly Gln
                180                 185                 190

Leu Glu Phe Leu Ile Gln Trp Gln Arg Ala Ser Ser Glu Arg Glu Thr
            195                 200                 205

Trp Tyr Ile Val Tyr Leu Leu Thr His Asp Phe Ser Phe Lys Glu Ile
210                 215                 220

Lys Leu Asn Asn Ile Ser Asn Tyr Phe Ile His Lys Phe Gly Lys Leu
225                 230                 235                 240

Lys Lys Gly Phe Ile Asn Gln Asp Leu Ala Ile Ala Arg Lys Lys Thr
                245                 250                 255

Tyr Phe Asn Ile Phe Leu Asp Phe Ile Leu Asn Leu Ile Asn Ile Leu
                260                 265                 270

Thr Ile Phe Ala Met Ile Leu Ser Val Arg Ala Gly Lys Leu Leu Ile
            275                 280                 285

Gly Asn Leu Val Ser Leu Ile Gln Ala Ile Ser Lys Ile Asn Thr Tyr
    290                 295                 300

Ser Gln Thr Met Ile Gln Asn Ile Tyr Ile Ile Tyr Asn Thr Ser Leu
305                 310                 315                 320

Phe Met Glu Gln Leu Phe Glu Phe Leu Lys Arg Glu Ser Val Val His
                325                 330                 335

Lys Lys Ile Glu Asp Thr Glu Ile Cys Asn Gln His Ile Gly Thr Val
                340                 345                 350

Lys Val Ile Asn Leu Ser Tyr Val Tyr Pro Asn Ser Asn Ala Phe Ala
            355                 360                 365

Leu Lys Asn Ile Asn Leu Ser Phe Glu Lys Gly Glu Leu Thr Ala Ile
    370                 375                 380

Val Gly Lys Asn Gly Ser Gly Lys Ser Thr Leu Val Lys Ile Ile Ser
385                 390                 395                 400

Gly Leu Tyr Gln Pro Thr Met Gly Ile Ile Gln Tyr Asp Lys Met Arg
                405                 410                 415

Ser Ser Leu Met Pro Glu Glu Tyr Gln Lys Asn Ile Ser Val Leu
                420                 425                 430

Phe Gln Asp Phe Val Lys Tyr Glu Leu Thr Ile Arg Glu Asn Ile Gly
        435                 440                 445

Leu Ser Asp Leu Ser Ser Gln Trp Glu Asp Glu Lys Ile Ile Lys Val
    450                 455                 460

Leu Asp Asn Leu Gly Leu Asp Phe Leu Lys Thr Asn Asn Gln Tyr Val
465                 470                 475                 480
```

```
Leu Asp Thr Gln Leu Gly Asn Trp Phe Gln Glu Gly His Gln Leu Ser
            485                 490                 495

Gly Gly Gln Trp Gln Lys Ile Ala Leu Ala Arg Thr Phe Phe Lys Lys
            500                 505                 510

Ala Ser Ile Tyr Ile Leu Asp Glu Pro Ser Ala Ala Leu Asp Pro Val
            515                 520                 525

Ala Glu Lys Glu Ile Phe Asp Tyr Phe Val Ala Leu Ser Glu Asn Asn
            530                 535                 540

Ile Ser Ile Phe Ile Ser His Ser Leu Asn Ala Arg Lys Ala Asn
545                 550                 555                 560

Lys Ile Val Val Met Lys Asp Gly Gln Val Glu Asp Val Gly Ser His
                    565                 570                 575

Asp Val Leu Leu Arg Arg Cys Gln Tyr Tyr Gln Glu Leu Tyr Tyr Ser
            580                 585                 590

Glu Gln Tyr Glu Asp Asn Asp Glu
            595                 600

<210> SEQ ID NO 32
<211> LENGTH: 414
<212> TYPE: PRT
<213> ORGANISM: Lactococcus sp.

<400> SEQUENCE: 32

Met Asn Lys Lys Asn Ile Lys Arg Asn Val Glu Lys Ile Ile Ala Gln
1               5                   10                  15

Trp Asp Glu Arg Thr Arg Lys Asn Lys Glu Asn Phe Asp Phe Gly Glu
            20                  25                  30

Leu Thr Leu Ser Thr Gly Leu Pro Gly Ile Ile Leu Met Leu Ala Glu
            35                  40                  45

Leu Lys Asn Lys Asp Asn Ser Lys Ile Tyr Gln Lys Lys Ile Asp Asn
        50                  55                  60

Tyr Ile Glu Tyr Ile Val Ser Lys Leu Ser Thr Tyr Gly Leu Leu Thr
65              70                  75                  80

Gly Ser Leu Tyr Ser Gly Ala Ala Gly Ile Ala Leu Ser Ile Leu His
                85                  90                  95

Leu Arg Glu Asp Asp Glu Lys Tyr Lys Asn Leu Leu Asp Ser Leu Asn
            100                 105                 110

Arg Tyr Ile Glu Tyr Phe Val Arg Glu Lys Ile Glu Gly Phe Asn Leu
        115                 120                 125

Glu Asn Ile Thr Pro Pro Asp Tyr Asp Val Ile Glu Gly Leu Ser Gly
    130                 135                 140

Ile Leu Ser Tyr Leu Leu Leu Ile Asn Asp Glu Gln Tyr Asp Asp Leu
145                 150                 155                 160

Lys Ile Leu Ile Ile Asn Phe Leu Ser Asn Leu Thr Lys Glu Asn Asn
                165                 170                 175

Gly Leu Ile Ser Leu Tyr Ile Lys Ser Glu Asn Gln Met Ser Gln Ser
            180                 185                 190

Glu Ser Glu Met Tyr Pro Leu Gly Cys Leu Asn Met Gly Leu Ala His
        195                 200                 205

Gly Leu Ala Gly Val Gly Cys Ile Leu Ala Tyr Ala His Ile Lys Gly
    210                 215                 220

Tyr Ser Asn Glu Ala Ser Leu Ser Ala Leu Gln Lys Ile Ile Phe Ile
225                 230                 235                 240

Tyr Glu Lys Phe Glu Leu Glu Arg Lys Lys Gln Phe Leu Trp Lys Asp
                245                 250                 255
```

-continued

Gly Leu Val Ala Asp Glu Leu Lys Lys Glu Lys Val Ile Arg Glu Ala
                260                 265                 270

Ser Phe Ile Arg Asp Ala Trp Cys Tyr Gly Pro Gly Ile Ser Leu
    275                 280                 285

Leu Tyr Leu Tyr Gly Gly Leu Ala Leu Asp Asn Asp Tyr Phe Val Asp
    290                 295                 300

Lys Ala Glu Lys Ile Leu Glu Ser Ala Met Gln Arg Lys Leu Gly Ile
305                 310                 315                 320

Asp Ser Tyr Met Ile Cys His Gly Tyr Ser Gly Leu Ile Glu Ile Cys
                325                 330                 335

Ser Leu Phe Lys Arg Leu Leu Asn Thr Lys Lys Phe Asp Ser Tyr Met
                340                 345                 350

Glu Glu Phe Asn Val Asn Ser Glu Gln Ile Leu Glu Glu Tyr Gly Asp
                355                 360                 365

Glu Ser Gly Thr Gly Phe Leu Gly Gly Ile Ser Gly Cys Ile Leu Val
                370                 375                 380

Leu Ser Lys Phe Glu Tyr Ser Ile Asn Phe Thr Tyr Trp Arg Gln Ala
385                 390                 395                 400

Leu Leu Leu Phe Asp Asp Phe Leu Lys Gly Gly Lys Arg Lys
                405                 410

<210> SEQ ID NO 33
<211> LENGTH: 245
<212> TYPE: PRT
<213> ORGANISM: Lactococcus sp.

<400> SEQUENCE: 33

Met Arg Arg Tyr Leu Ile Leu Ile Val Ala Leu Ile Gly Ile Thr Gly
  1               5                  10                  15

Leu Ser Gly Cys Tyr Gln Thr Ser His Lys Lys Val Arg Phe Asp Glu
                20                  25                  30

Gly Ser Tyr Thr Asn Phe Ile Tyr Asp Asn Lys Ser Tyr Phe Val Thr
            35                  40                  45

Asp Lys Glu Ile Pro Gln Glu Asn Val Asn Asn Ser Lys Val Lys Phe
     50                  55                  60

Tyr Lys Leu Leu Ile Val Asp Met Lys Ser Glu Lys Leu Leu Ser Ser
 65                  70                  75                  80

Ser Asn Lys Asn Ser Val Thr Leu Val Leu Asn Asn Ile Tyr Glu Ala
                 85                  90                  95

Ser Asp Lys Ser Leu Cys Met Gly Ile Asn Asp Arg Tyr Tyr Lys Ile
            100                 105                 110

Leu Pro Glu Ser Asp Lys Gly Ala Val Lys Ala Leu Arg Leu Gln Asn
        115                 120                 125

Phe Asp Val Thr Ser Asp Ile Ser Asp Asp Asn Phe Val Ile Asp Lys
    130                 135                 140

Asn Asp Ser Arg Lys Ile Asp Tyr Met Gly Asn Ile Tyr Ser Ile Ser
145                 150                 155                 160

Asp Thr Thr Val Ser Asp Glu Glu Leu Gly Glu Tyr Gln Asp Val Leu
                165                 170                 175

Ala Glu Val Arg Val Phe Asp Ser Val Ser Gly Lys Ser Ile Pro Arg
            180                 185                 190

Ser Glu Trp Gly Arg Ile Asp Lys Asp Gly Ser Asn Ser Lys Gln Ser
        195                 200                 205

Arg Thr Glu Trp Asp Tyr Gly Glu Ile His Ser Ile Arg Gly Lys Ser

| | 210 | | | 215 | | | 220 | | | | |
|---|---|---|---|---|---|---|---|---|---|---|---|

Leu Thr Glu Ala Phe Ala Val Glu Ile Asn Asp Asp Phe Lys Leu Ala
225                 230                 235                 240

Thr Lys Val Gly Asn
            245

<210> SEQ ID NO 34
<211> LENGTH: 67
<212> TYPE: PRT
<213> ORGANISM: Lactococcus sp.

<400> SEQUENCE: 34

Val Lys Lys Ile Leu Gly Phe Leu Phe Ile Val Cys Ser Leu Gly Leu
 1               5                  10                  15

Ser Ala Thr Val His Gly Glu Thr Thr Asn Ser Gln Gln Leu Leu Ser
            20                  25                  30

Asn Asn Ile Asn Thr Glu Leu Ile Asn His Asn Ser Asn Ala Ile Leu
        35                  40                  45

Ser Ser Thr Glu Gly Ser Thr Thr Asp Ser Ile Asn Leu Gly Ala Gln
    50                  55                  60

Ser Pro Ala
 65

<210> SEQ ID NO 35
<211> LENGTH: 5000
<212> TYPE: DNA
<213> ORGANISM: Lactococcus sp.

<400> SEQUENCE: 35

```
caattttact tattggagac aagcactgtt acttttttgac gatttttttga aaggagggaa      60
gaggaaatga aagatatttt aatacttatt gtggccttaa tagggataac aggttttatca     120
gggtgttatc aaacaagtca taaaaaggtg aggtttgacg aaggaagtta tactaatttt     180
atttatgata taaatcgta tttcgtaact gataaggaga ttcctcagga gaacgttaac      240
aattccaaag taaaatttta taagctgttg attgttgaca tgaaaagtga gaaactttta     300
tcaagtagca acaaaaatag tgtgactttg gtcttaaata atattttatga ggcttctgac     360
aagtcgctat gtatgggtat taacgacaga tactataaga tacttccaga aagtgataag     420
ggggcggtca aagctttgag attacaaaac tttgatgtga caagcgatat ttctgatgat     480
aattttgtta ttgataaaaa tgattcacga aaaattgact atatgggaaa tatttacagt     540
atatcggaca ccaccgtatc tgatgaagaa ttgggagaat atcaggatgt tttagctgaa     600
gtacgtgtgt ttgattcagt tagtggcaaa agtatcccga ggtctgaatg ggggagaatt     660
gataaggatg gttcaaattc caaacagagt aggacggaat gggattatgg cgaaatccat     720
tctattagag gaaaatctct tactgaagca tttgccgttg agataaatga tgattttaag     780
cttgcaacga aggtaggaaa ctagagtgaa aaaaatacta ggtttccttt ttatcgtttg     840
ttcgttgggt ttatcagcaa ctgtgcatgg ggagacaaca aattcacaac agttactctc     900
aaataatatt aatacggaat taattaatca taattctaat gcaattttat cttcaacaga     960
gggatcaacg actgattcga ttaatctagg ggcgcagtca cctgcagtaa aatcgacaac    1020
aaggactgaa ttggatgtaa ctggtgctgc taaaacttta ttacagacat cagctgttca    1080
aaaagaaatg aaagtttcgt tgcaagaaac tcaagttagt tctgaattca gtaagagaga    1140
tagcgttaca aataaagaag cagttccagt atctaaggat gagctacttg agcaaagtga    1200
```

```
agtagtcgtt tcaacatcat cgattcaaaa aaataaaatc ctcgataata agaagaaaag    1260
agctaacttc gttacttcct ctccgcttat taaggaaaaa ccatcaaatt ctaaagatgc    1320
atctggtgta attgataatt ctgcttctcc tctatcttat cgtaaagcta aggaagtggt    1380
atctcttaga caacctttaa aaaatcaaaa agtagaggca caacctctat tgataagtaa    1440
ttcttctgaa aagaaagcaa gtgttttatac aaattcacat gattttttggg attatcagtg    1500 ggatatgaaa tatgtgacaa ataatggaga aagctatgcg ctctaccagc cctcaaagaa    1560
aatttctgtt ggaattattg attcaggaat catggaagaa catcctgatt tgtcaaatag    1620
tttaggaaat tattttaaaa atcttgttcc taagggaggg tttgataatg aagaacctga    1680
tgaaactgga atccaagtg atattgtcga caaatggga cacggacgg aagtcgcagg    1740 tcagattaca gcaaatggta atattttagg agtagcacca gggattactg taaatatata    1800
cagagtattt ggtgaaaatc tttcgaaatc ggaatgggta gctagagcaa taagaagagc    1860
tgcggatgat gggaacaagg tcatcaatat aagtgctgga cagtatctta tgatttcagg    1920
atcgtatgat gatggaacaa atgattatca agagtatctt aattataagt cagcaataaa    1980
ttatgcaaca gcaaaggaa gtattgttgt cgcagctctt ggtaatgata gtttaaacat    2040
acaagataac caaacaatga taaactttct taagcgtttc agaagtataa aggttcctgg    2100
aaaagttgta gatgcaccga gtgtatttga ggatgtaata gccgtaggtg aatagatgg    2160 ttatggtaat atttctgatt ttagtaatat tggagcggat gcaatttatg ctcctgctgg    2220
cacaacggcc aattttaaaa aatatgggca agataaattt gtcagtcagg gttattattt    2280
gaaagattgg cttttttacaa ctgctaatac tggctggtac caatatgttt atggcaactc    2340
atttgctact cctaaagtat ctggggcact ggcattagta gttgataaat atggaataaa    2400
gaatcctaac caactaaaaa ggtttcttct aatgaattct ccagaagtta atgggaatag    2460
agtattgaat attgttgatt tattgaatgg gaaaaataaa gcttttagct tagatacaga    2520
taaaggtcag gatgatgcta ttaaccataa atcgatggag aatcttaaag agtctaggga    2580
tacaatgaaa caggaacaag ataaagaaat tcaaagaaat acaaataaca atttttctat    2640
caaaaatgat tttcataaca tttcaaaaga agtaatttca gttgattata atattaatca    2700
aaaaatggct aataatcgaa attcgagagg tgctgtttct gtacgaagtc aagaaatttt    2760
acctgttact ggagatggag aagatttttt accggcttta ggtatagtgt gtatctcaat    2820
ccttggtata ttgaaaagaa agactaaaaa ttgatagatt atatttcttc agaatgaatg    2880
gtataatgaa gtaatgagta ctaaacaatc ggaggtaaag tggtgtataa aattttaata    2940
gttgatgatg atcaggaaat tttaaaatta atgaagacag cattagaaat gagaaactat    3000
gaagttgcga cgcatcaaaa catttcactt cccttggata ttactgattt tcagggattt    3060
gatttgattt tgttagatat catgatgtca aatattgaag gacagaaat ttgtaaaagg    3120 attcgcagag aaatatcaac tccaattatc tttgttagtg cgaaagatac agaagaggat    3180
attataaacg gctaggtat tggtgggat gactatatta ctaagccttt tagccttaaa    3240
cagttggttg caaaagtgga agcaaatata aagcgagagg aacgcaataa acatgcagtt    3300
catgtttttt cagagattcg tagagattta ggaccaatta catttttatt agaagaaagg    3360
cgagtctgtg tcaatggtca aacaattcca ctgacttgtc gtgaatacga tattcttgaa    3420
ttactatcac aacgaacttc taaagtttat acgagagagg atatttatga tgacgtatat    3480
gatgaatatt ctaatgcact ttttcggtca atctcggagt atatttatca gattaggagt    3540
aagtttgcac catacgatat taatccgata aaaacggttc ggggacttgg gtatcagtgg    3600
```

-continued

```
catgggtaaa aaatattcaa tgcgtcgacg gatatggcaa gctgtcattg aaattatcat    3660
aggtacttgt ctactatcc tgttgttact gggcttgact ttctttctac gacaaattgg    3720
acaaatcagt ggttcagaaa ctattcgttt atctttagat tcagataatt taactatttc    3780
tgatatcgaa cgtgatatga aacactaccc atatgattat attattttg acaatgatac    3840 aagtaaaatt ttgggaggac attatgtcaa gtcggatgta cctagttttg tagcttcaaa    3900
acagtcttca cataatatta cagaaggaga aattacttat acttattcaa gcaataagca    3960
tttttcagtt gttttaagac aaaacagtat gcctgaattt acaaatcata cgcttcgttc    4020
aatttcttat aatcaattta cttacctttt cttttttctt ggtgaaataa tactcattat    4080
tttttctgtc tatcatctca ttagagaatt ttctaagaat tttcaagccg ttcaaaagat    4140
tgcattgaag atgggggaaa taactacttt tcctgaacaa gaggaatcaa aaattattga    4200
atttgatcag gttctgaata acttatattc gaaagtaag gagttagctt tccttattga    4260
agcggagcgt catgaaaaac atgatttatc cttccaggtt gctgcacttt cacatgatgt    4320
taagacacct ttaacagtat taaaggaaa tattgaactg ctagagatga ctgaagtaaa    4380
tgaacaacaa gctgatttta ttgagtcaat gaaaaatagt ttgactgttt tgacaagta    4440 tttttaacaca atgattagtt atacaaaact tttgaatgat gaaaatgatt acaaagcgac    4500
aatctccctg gaggattttt tgatagattt atcagttgag ttggaagagt tgtcaacaac    4560
ttatcaagtg gattatcagc tagttaaaaa aacagattta accactttt acggaaatac    4620 attagcttta agtcgagcac ttatcaatat ctttgttaat gcctgtcagt atgctaaaga    4680
gggtgaaaaa atagtcagtt tgagtattta tgatgatgaa aaatatctct attttgaaat    4740
ctggaataat ggtcatcctt tttctgaaca agcaaaaaaa aatgctggaa aactatttt    4800 cacagaagat actggacgta gtgggaaaca ctatgggatt ggactatctt ttgctcaagg    4860
tgtagcttta aaacatcaag gaaacttaat tctcagtaat cctcaaaaag gtggggcaga    4920
agttatccta aaaataaaaa agtaatttag taatctctaa ggattacttt ttttgtttct    4980
gaatagattc tgaaaattgt                                               5000
```

<210> SEQ ID NO 36
<211> LENGTH: 22
<212> TYPE: PRT
<213> ORGANISM: Lactococcus sp.

<400> SEQUENCE: 36

Asn Phe Thr Tyr Trp Arg Gln Ala Leu Leu Leu Phe Asp Asp Phe Leu
 1               5                  10                  15

Lys Gly Gly Lys Arg Lys
            20

<210> SEQ ID NO 37
<211> LENGTH: 682
<212> TYPE: PRT
<213> ORGANISM: Lactococcus sp.

<400> SEQUENCE: 37

Val Lys Lys Ile Leu Gly Phe Leu Phe Ile Val Cys Ser Leu Gly Leu
 1               5                  10                  15

Ser Ala Thr Val His Gly Glu Thr Thr Asn Ser Gln Gln Leu Leu Ser
            20                  25                  30

Asn Asn Ile Asn Thr Glu Leu Ile Asn His Asn Ser Asn Ala Ile Leu
        35                  40                  45

-continued

```
Ser Ser Thr Glu Gly Ser Thr Thr Asp Ser Ile Asn Leu Gly Ala Gln
     50                  55                  60
Ser Pro Ala Val Lys Ser Thr Thr Arg Thr Glu Leu Asp Val Thr Gly
 65                  70                  75                  80
Ala Ala Lys Thr Leu Leu Gln Thr Ser Ala Val Gln Lys Glu Met Lys
                 85                  90                  95
Val Ser Leu Gln Glu Thr Gln Val Ser Ser Glu Phe Ser Lys Arg Asp
                100                 105                 110
Ser Val Thr Asn Lys Glu Ala Val Pro Val Ser Lys Asp Glu Leu Leu
            115                 120                 125
Glu Gln Ser Glu Val Val Ser Thr Ser Ser Ile Gln Lys Asn Lys
        130                 135                 140
Ile Leu Asp Asn Lys Lys Lys Arg Ala Asn Phe Val Thr Ser Ser Pro
145                 150                 155                 160
Leu Ile Lys Glu Lys Pro Ser Asn Ser Lys Asp Ala Ser Gly Val Ile
                165                 170                 175
Asp Asn Ser Ala Ser Pro Leu Ser Tyr Arg Lys Ala Lys Glu Val Val
            180                 185                 190
Ser Leu Arg Gln Pro Leu Lys Asn Gln Lys Val Glu Ala Gln Pro Leu
        195                 200                 205
Leu Ile Ser Asn Ser Ser Glu Lys Lys Ala Ser Val Tyr Thr Asn Ser
    210                 215                 220
His Asp Phe Trp Asp Tyr Gln Trp Asp Met Lys Tyr Val Thr Asn Asn
225                 230                 235                 240
Gly Glu Ser Tyr Ala Leu Tyr Gln Pro Ser Lys Lys Ile Ser Val Gly
                245                 250                 255
Ile Ile Asp Ser Gly Ile Met Glu Glu His Pro Asp Leu Ser Asn Ser
            260                 265                 270
Leu Gly Asn Tyr Phe Lys Asn Leu Val Pro Lys Gly Phe Asp Asn
        275                 280                 285
Glu Glu Pro Asp Glu Thr Gly Asn Pro Ser Asp Ile Val Asp Lys Met
    290                 295                 300
Gly His Gly Thr Glu Val Ala Gly Gln Ile Thr Ala Asn Gly Asn Ile
305                 310                 315                 320
Leu Gly Val Ala Pro Gly Ile Thr Val Asn Ile Tyr Arg Val Phe Gly
                325                 330                 335
Glu Asn Leu Ser Lys Ser Glu Trp Val Ala Arg Ala Ile Arg Arg Ala
            340                 345                 350
Ala Asp Asp Gly Asn Lys Val Ile Asn Ile Ser Ala Gly Gln Tyr Leu
        355                 360                 365
Met Ile Ser Gly Ser Tyr Asp Asp Gly Thr Asn Asp Tyr Gln Glu Tyr
    370                 375                 380
Leu Asn Tyr Lys Ser Ala Ile Asn Tyr Ala Thr Ala Lys Gly Ser Ile
385                 390                 395                 400
Val Val Ala Ala Leu Gly Asn Asp Ser Leu Asn Ile Gln Asp Asn Gln
                405                 410                 415
Thr Met Ile Asn Phe Leu Lys Arg Phe Arg Ser Ile Lys Val Pro Gly
            420                 425                 430
Lys Val Val Asp Ala Pro Ser Val Phe Glu Asp Val Ile Ala Val Gly
        435                 440                 445
Gly Ile Asp Gly Tyr Gly Asn Ile Ser Asp Phe Ser Asn Ile Gly Ala
    450                 455                 460
```

```
Asp Ala Ile Tyr Ala Pro Ala Gly Thr Thr Ala Asn Phe Lys Lys Tyr
465                 470                 475                 480

Gly Gln Asp Lys Phe Val Ser Gln Gly Tyr Tyr Leu Lys Asp Trp Leu
            485                 490                 495

Phe Thr Thr Ala Asn Thr Gly Trp Tyr Gln Tyr Val Tyr Gly Asn Ser
                500                 505                 510

Phe Ala Thr Pro Lys Val Ser Gly Ala Leu Ala Leu Val Val Asp Lys
            515                 520                 525

Tyr Gly Ile Lys Asn Pro Asn Gln Leu Lys Arg Phe Leu Leu Met Asn
530                 535                 540

Ser Pro Glu Val Asn Gly Asn Arg Val Leu Asn Ile Val Asp Leu Leu
545                 550                 555                 560

Asn Gly Lys Asn Lys Ala Phe Ser Leu Asp Thr Asp Lys Gly Gln Asp
                565                 570                 575

Asp Ala Ile Asn His Lys Ser Met Glu Asn Leu Lys Glu Ser Arg Asp
                580                 585                 590

Thr Met Lys Gln Glu Gln Asp Lys Glu Ile Gln Arg Asn Thr Asn Asn
                595                 600                 605

Asn Phe Ser Ile Lys Asn Asp Phe His Asn Ile Ser Lys Glu Val Ile
610                 615                 620

Ser Val Asp Tyr Asn Ile Asn Gln Lys Met Ala Asn Asn Arg Asn Ser
625                 630                 635                 640

Arg Gly Ala Val Ser Val Arg Ser Gln Glu Ile Leu Pro Val Thr Gly
                645                 650                 655

Asp Gly Glu Asp Phe Leu Pro Ala Leu Gly Ile Val Cys Ile Ser Ile
                660                 665                 670

Leu Gly Ile Leu Lys Arg Lys Thr Lys Asn
                675                 680

<210> SEQ ID NO 38
<211> LENGTH: 229
<212> TYPE: PRT
<213> ORGANISM: Lactococcus sp.

<400> SEQUENCE: 38

Val Val Tyr Lys Ile Leu Ile Val Asp Asp Gln Glu Ile Leu Lys
1               5                   10                  15

Leu Met Lys Thr Ala Leu Glu Met Arg Asn Tyr Glu Val Ala Thr His
                20                  25                  30

Gln Asn Ile Ser Leu Pro Leu Asp Ile Thr Asp Phe Gln Gly Phe Asp
            35                  40                  45

Leu Ile Leu Leu Asp Ile Met Met Ser Asn Ile Glu Gly Thr Glu Ile
50                  55                  60

Cys Lys Arg Ile Arg Arg Glu Ile Ser Thr Pro Ile Ile Phe Val Ser
65                  70                  75                  80

Ala Lys Asp Thr Glu Glu Asp Ile Ile Asn Gly Leu Gly Ile Gly Gly
                85                  90                  95

Asp Asp Tyr Ile Thr Lys Pro Phe Ser Leu Lys Gln Leu Val Ala Lys
            100                 105                 110

Val Glu Ala Asn Ile Lys Arg Glu Glu Arg Asn Lys His Ala Val His
            115                 120                 125

Val Phe Ser Glu Ile Arg Arg Asp Leu Gly Pro Ile Thr Phe Tyr Leu
130                 135                 140

Glu Glu Arg Arg Val Cys Val Asn Gly Gln Thr Ile Pro Leu Thr Cys
145                 150                 155                 160
```

```
Arg Glu Tyr Asp Ile Leu Glu Leu Leu Ser Gln Arg Thr Ser Lys Val
                165                 170                 175

Tyr Thr Arg Glu Asp Ile Tyr Asp Val Tyr Asp Glu Tyr Ser Asn
            180                 185                 190

Ala Leu Phe Arg Ser Ile Ser Glu Tyr Ile Tyr Gln Ile Arg Ser Lys
                195                 200                 205

Phe Ala Pro Tyr Asp Ile Asn Pro Ile Lys Thr Val Arg Gly Leu Gly
            210                 215                 220

Tyr Gln Trp His Gly
225
```

<210> SEQ ID NO 39
<211> LENGTH: 447
<212> TYPE: PRT
<213> ORGANISM: Lactococcus sp.

<400> SEQUENCE: 39

```
Met Gly Lys Lys Tyr Ser Met Arg Arg Ile Trp Gln Ala Val Ile
 1               5                  10                  15

Glu Ile Ile Ile Gly Thr Cys Leu Leu Ile Leu Leu Leu Gly Leu
                20                  25                  30

Thr Phe Phe Leu Arg Gln Ile Gly Gln Ile Ser Gly Ser Glu Thr Ile
                35                  40                  45

Arg Leu Ser Leu Asp Ser Asp Asn Leu Thr Ile Ser Asp Ile Glu Arg
    50                  55                  60

Asp Met Lys His Tyr Pro Tyr Asp Tyr Ile Ile Phe Asp Asn Asp Thr
65                  70                  75                  80

Ser Lys Ile Leu Gly Gly His Tyr Val Lys Ser Asp Val Pro Ser Phe
                85                  90                  95

Val Ala Ser Lys Gln Ser Ser His Asn Ile Thr Glu Gly Glu Ile Thr
                100                 105                 110

Tyr Thr Tyr Ser Ser Asn Lys His Phe Ser Val Val Leu Arg Gln Asn
                115                 120                 125

Ser Met Pro Glu Phe Thr Asn His Thr Leu Arg Ser Ile Ser Tyr Asn
130                 135                 140

Gln Phe Thr Tyr Leu Phe Phe Leu Gly Ile Ile Leu Ile Ile
145                 150                 155                 160

Phe Ser Val Tyr His Leu Ile Arg Glu Phe Ser Lys Asn Phe Gln Ala
                165                 170                 175

Val Gln Lys Ile Ala Leu Lys Met Gly Glu Ile Thr Thr Phe Pro Glu
                180                 185                 190

Gln Glu Glu Ser Lys Ile Ile Glu Phe Asp Gln Val Leu Asn Asn Leu
                195                 200                 205

Tyr Ser Lys Ser Lys Glu Leu Ala Phe Leu Ile Glu Ala Glu Arg His
                210                 215                 220

Glu Lys His Asp Leu Ser Phe Gln Val Ala Ala Leu Ser His Asp Val
225                 230                 235                 240

Lys Thr Pro Leu Thr Val Leu Lys Gly Asn Ile Glu Leu Leu Glu Met
                245                 250                 255

Thr Glu Val Asn Glu Gln Gln Ala Asp Phe Ile Glu Ser Met Lys Asn
                260                 265                 270

Ser Leu Thr Val Phe Asp Lys Tyr Phe Asn Thr Met Ile Ser Tyr Thr
                275                 280                 285

Lys Leu Leu Asn Asp Glu Asn Asp Tyr Lys Ala Thr Ile Ser Leu Glu
```

```
              290                 295                 300
Asp Phe Leu Ile Asp Leu Ser Val Glu Leu Glu Glu Leu Ser Thr Thr
305                 310                 315                 320

Tyr Gln Val Asp Tyr Gln Leu Val Lys Lys Thr Asp Leu Thr Thr Phe
                325                 330                 335

Tyr Gly Asn Thr Leu Ala Leu Ser Arg Ala Leu Ile Asn Ile Phe Val
            340                 345                 350

Asn Ala Cys Gln Tyr Ala Lys Glu Gly Glu Lys Ile Val Ser Leu Ser
            355                 360                 365

Ile Tyr Asp Asp Glu Lys Tyr Leu Tyr Phe Glu Ile Trp Asn Asn Gly
        370                 375                 380

His Pro Phe Ser Glu Gln Ala Lys Lys Asn Ala Gly Lys Leu Phe Phe
385                 390                 395                 400

Thr Glu Asp Thr Gly Arg Ser Gly Lys His Tyr Gly Ile Gly Leu Ser
                405                 410                 415

Phe Ala Gln Gly Val Ala Leu Lys His Gln Gly Asn Leu Ile Leu Ser
            420                 425                 430

Asn Pro Gln Lys Gly Gly Ala Glu Val Ile Leu Lys Ile Lys Lys
            435                 440                 445

<210> SEQ ID NO 40
<211> LENGTH: 57
<212> TYPE: PRT
<213> ORGANISM: Lactococcus sp.

<400> SEQUENCE: 40

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Leu Thr Gly Ala Leu Met Gly Cys Asn Met Lys Thr Ala Thr
        35                  40                  45

Cys His Cys Ser Ile His Val Ser Lys
    50                  55

<210> SEQ ID NO 41
<211> LENGTH: 56
<212> TYPE: PRT
<213> ORGANISM: Lactococcus sp.

<400> SEQUENCE: 41

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Lys Thr Ala Thr Cys
        35                  40                  45

His Cys Ser Ile His Val Ser Lys
    50                  55

<210> SEQ ID NO 42
<211> LENGTH: 57
<212> TYPE: PRT
<213> ORGANISM: Lactococcus sp.

<400> SEQUENCE: 42

Met Ser Thr Lys Asp Phe Asn Leu Asp Leu Val Ser Val Ser Lys Lys
1               5                   10                  15
```

```
Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
            35                  40                  45

Cys Lys Cys Ser Ile His Val Ser Lys
            50                  55
```

<210> SEQ ID NO 43
<211> LENGTH: 57
<212> TYPE: PRT
<213> ORGANISM: Lactococcus sp.

<400> SEQUENCE: 43

```
Met Ser Thr Lys Asp Phe Asn Leu Asp Leu Val Ser Val Ser Lys Lys
  1               5                  10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
            35                  40                  45

Cys His Cys Ser Trp His Val Ser Lys
            50                  55
```

<210> SEQ ID NO 44
<211> LENGTH: 57
<212> TYPE: PRT
<213> ORGANISM: Lactococcus sp.

<400> SEQUENCE: 44

```
Met Ser Thr Lys Asp Phe Asn Leu Asp Leu Val Ser Val Ser Lys Lys
  1               5                  10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
            35                  40                  45

Cys Trp Cys Ser Ile His Val Ser Lys
            50                  55
```

<210> SEQ ID NO 45
<211> LENGTH: 57
<212> TYPE: PRT
<213> ORGANISM: Lactococcus sp.

<400> SEQUENCE: 45

```
Met Ser Thr Lys Asp Phe Asn Leu Asp Leu Val Ser Val Ser Lys Lys
  1               5                  10                  15

Asp Ser Gly Ala Ser Pro Arg Ile Thr Ser Ile Ala Leu Cys Thr Pro
            20                  25                  30

Gly Cys Lys Thr Gly Ala Leu Met Gly Cys Asn Met Lys Thr Ala Thr
            35                  40                  45

Cys Trp Cys Ser Ile His Val Ser Lys
            50                  55
```

<210> SEQ ID NO 46
<211> LENGTH: 57
<212> TYPE: PRT
<213> ORGANISM: Lactococcus sp.

<400> SEQUENCE: 46

```
Met Ser Thr Lys Asp Phe Asn Leu Asp Leu Val Ser Val Ser Lys Lys
```

```
                1               5              10              15
Asp Ser Gly Ala Ser Pro Arg Ile Thr Ser Ile Ser Leu Cys Thr Pro
                        20                  25                  30

Gly Cys Lys Thr Gly Ala Leu Met Gly Cys Asn Met Lys Thr Ala Thr
            35                  40                  45

Cys His Cys Ser Ile Lys Val Ser Lys
        50                  55
```

<210> SEQ ID NO 47
<211> LENGTH: 57
<212> TYPE: PRT
<213> ORGANISM: Lactococcus sp.

<400> SEQUENCE: 47

```
Met Ser Thr Lys Asp Phe Asn Leu Asp Leu Val Ser Val Ser Lys Lys
 1               5                  10                  15

Asp Ser Gly Ala Ser Pro Arg Ile Thr Ser Ile Ser Leu Cys Thr Pro
                        20                  25                  30

Gly Cys Lys Thr Gly Ala Leu Met Gly Cys Asn Met Lys Thr Ala Thr
            35                  40                  45

Cys Lys Cys Ser Ile Lys Val Ser Lys
        50                  55
```

<210> SEQ ID NO 48
<211> LENGTH: 34
<212> TYPE: PRT
<213> ORGANISM: Lactococcus sp.
<220> FEATURE:
<221> NAME/KEY: UNSURE
<222> LOCATION: (2)
<223> OTHER INFORMATION: Xaa at position 2 is  dihydroxybenzoic acid
<221> NAME/KEY: UNSURE
<222> LOCATION: (5)
<223> OTHER INFORMATION: Xaa at position 5 is dehydroalanine
<221> NAME/KEY: UNSURE
<222> LOCATION: (8)..(25)
<223> OTHER INFORMATION: Xaa at positions 8, 13, 23, and 25 are
      2-aminobutyric acid
<221> NAME/KEY: UNSURE
<222> LOCATION: (33)
<223> OTHER INFORMATION: Xaa at position 33 is dehydroalanine

<400> SEQUENCE: 48

```
Ile Xaa Ala Ile Xaa Leu Ala Xaa Pro Gly Ala Lys Xaa Gly Ala Leu
 1               5                  10                  15

Met Gly Ala Asn Met Lys Xaa Ala Xaa Ala His Ala Ser Ile His Val
                20                  25                  30

Xaa Lys
```

<210> SEQ ID NO 49
<211> LENGTH: 34
<212> TYPE: PRT
<213> ORGANISM: Lactococcus sp.
<220> FEATURE:
<221> NAME/KEY: UNSURE
<222> LOCATION: (2)
<223> OTHER INFORMATION: Xaa at position 2 is dihydroxybenzoic acid
<221> NAME/KEY: UNSURE
<222> LOCATION: (8)..(25)
<223> OTHER INFORMATION: Xaa at positions 8, 13, 23, and 25 are
      2-aminobutyric acid

<400> SEQUENCE: 49

```
Ile Xaa Ala Ile Ala Leu Ala Xaa Pro Gly Ala Lys Xaa Gly Ala Leu
 1               5                  10                  15
```

-continued

```
Met Gly Ala Asn Met Lys Xaa Ala Xaa Ala His Ala Ser Ile His Val
            20                  25                  30

Ala Lys

<210> SEQ ID NO 50
<211> LENGTH: 34
<212> TYPE: PRT
<213> ORGANISM: Lactococcus sp.
<220> FEATURE:
<221> NAME/KEY: UNSURE
<222> LOCATION: (2)
<223> OTHER INFORMATION: Xaa at position 2 is dihydroxybenzoic acid
<221> NAME/KEY: UNSURE
<222> LOCATION: (8)..(25)
<223> OTHER INFORMATION: Xaa at positions 8, 13, 23, and 25 are
      2-aminobutyric acid
<221> NAME/KEY: UNSURE
<222> LOCATION: (33)
<223> OTHER INFORMATION: Xaa at position 33 is dehydroalanine

<400> SEQUENCE: 50

Ile Xaa Ala Ile Ala Leu Ala Xaa Pro Gly Ala Lys Xaa Gly Ala Leu
 1               5                  10                  15

Met Gly Ala Asn Met Lys Xaa Ala Xaa Ala His Ala Ser Ile His Val
            20                  25                  30

Xaa Lys

<210> SEQ ID NO 51
<211> LENGTH: 34
<212> TYPE: PRT
<213> ORGANISM: Lactococcus sp.
<220> FEATURE:
<221> NAME/KEY: UNSURE
<222> LOCATION: (2)
<223> OTHER INFORMATION: Xaa at position 2 is dihydroxybenzoic acid
<221> NAME/KEY: UNSURE
<222> LOCATION: (5)
<223> OTHER INFORMATION: Xaa at position 5 is dehydroalanine
<221> NAME/KEY: UNSURE
<222> LOCATION: (8)..(25)
<223> OTHER INFORMATION: Xaa at positions 8, 13, 23, and 25 are
      2-aminobutyric acid

<400> SEQUENCE: 51

Ile Xaa Ala Ile Xaa Leu Ala Xaa Pro Gly Ala Lys Xaa Gly Ala Leu
 1               5                  10                  15

Met Gly Ala Asn Met Lys Xaa Ala Xaa Ala His Ala Ser Ile His Val
            20                  25                  30

Ala Lys
```